United States Patent
Hareyama et al.

(10) Patent No.: US 8,642,625 B2
(45) Date of Patent: Feb. 4, 2014

(54) THERAPEUTIC AGENT OR PREVENTIVE AGENT FOR URINE COLLECTION DISORDER

(75) Inventors: Nana Hareyama, Kamakura (JP); Satoru Yoshikawa, Kamakura (JP); Kaoru Nakao, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/637,064

(22) PCT Filed: Mar. 31, 2011

(86) PCT No.: PCT/JP2011/058220
§ 371 (c)(1),
(2), (4) Date: Oct. 11, 2012

(87) PCT Pub. No.: WO2011/125838
PCT Pub. Date: Oct. 13, 2011

(65) Prior Publication Data
US 2013/0041157 A1    Feb. 14, 2013

(30) Foreign Application Priority Data
Mar. 31, 2010  (JP) .................................. 2010-083723

(51) Int. Cl.
*A61K 31/4427* (2006.01)
*A61K 31/426* (2006.01)
*A61K 31/421* (2006.01)
*A61K 31/415* (2006.01)
*C07D 401/02* (2006.01)
*C07D 277/20* (2006.01)
*C07D 263/30* (2006.01)
*C07D 231/10* (2006.01)

(52) U.S. Cl.
USPC ........... 514/341; 514/365; 514/374; 514/406; 546/275.4; 548/202; 548/235; 548/377.1

(58) Field of Classification Search
USPC ............... 514/341, 365, 374, 406; 546/275.4; 548/202, 235, 377.1
See application file for complete search history.

(56) References Cited

U.S. PATENT DOCUMENTS 8,247,569 B2 *  8/2012  Morita et al. ............... 546/275.4
8,349,874 B2 *  1/2013  Morita et al. ................. 514/341

FOREIGN PATENT DOCUMENTS

| WO | 98/46216 A1 | 10/1998 |
| WO | 00/66562 A1 | 11/2000 |
| WO | 2008/105383 A1 | 9/2008 |

OTHER PUBLICATIONS

Saito, M. et al., "Effectiveness of an Anti-Inflammatory Drug, Loxoprofen, for Patients with Nocturia," *International Journal of Urology*, 2006, vol. 12, pp. 779-782.

* cited by examiner

*Primary Examiner* — Samantha Shterengarts
(74) *Attorney, Agent, or Firm* — DLA Piper LLP (US)

(57) ABSTRACT

A therapeutic agent or prophylactic agent is effective for therapy of urine storage disorders, by which agent improvement of side effects due to an anticholinergic action is attained as well as which agent also has an analgesic effect. The agent includes as an effective ingredient a cyclohexane derivative exemplified by the formula below, a pharmaceutically acceptable salt thereof, or a prodrug thereof.

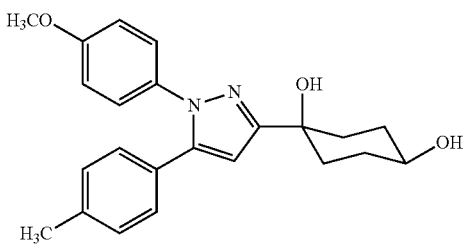

16 Claims, 1 Drawing Sheet

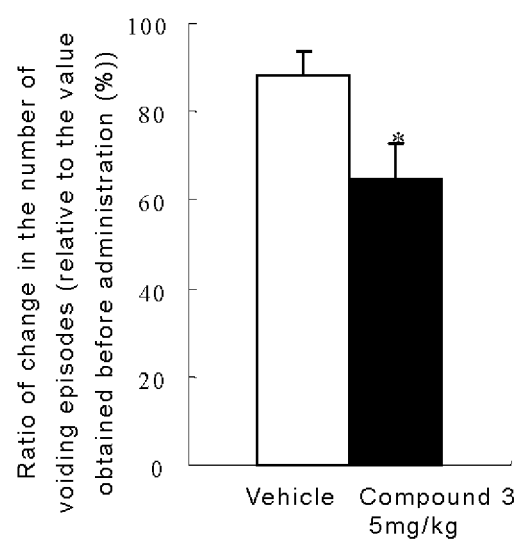

THERAPEUTIC AGENT OR PREVENTIVE AGENT FOR URINE COLLECTION DISORDER

RELATED APPLICATIONS

This is a §371 of International Application No. PCT/JP2011/058220, with an international filing date of Mar. 31, 2011, which is based on Japanese Patent Application No. 2010-083723, filed Mar. 31, 2010, the subject matter of which is incorporated by reference.

TECHNICAL FIELD

This disclosure relates to a therapeutic agent or prophylactic agent for a urine storage disorder(s).

BACKGROUND

Urine storage disorder is a state in which the urinary bladder is not able to store a sufficient amount of urine on urine storage, and the main symptoms thereof include pollakiuria, urinary incontinence and urinary urgency. Pollakiuria is a state in which the number of voiding episodes is more than normal; urinary incontinence is a state in which involuntary or unconscious leakage of urine occurs and it becomes a hygienic and social problem; and urinary urgency is a state in which a person feels a strong, compelling need to urinate which suddenly occurs. At present, as a therapeutic agent for a urine storage disorder(s) such as pollakiuria, urinary incontinence, urinary urgency and/or the like, anticholinergic agents have been mainly used. The anticholinergic agents are agents that bind to muscarinic receptors and exert a receptor antagonistic action (an anticholinergic action).

Patients experiencing a urine storage disorder(s) such as pollakiuria, urinary incontinence and/or urinary urgency may also complain of pain. For example, in cases where the cause is interstitial cystitis, it has been known that the patients also have lower abdominal pain during urine storage, and/or pain and/or discomfort in the vesico-urethral portion on urination in addition to a urine storage disorder(s) such as pollakiuria, urinary incontinence and/or urinary urgency.

Some of pharmaceuticals that have been used as an analgesic so far have been demonstrated to be effective against urine storage disorders including pollakiuria and urinary incontinence. For example, it has been reported that loxoprofen, which is a nonsteroidal anti-inflammatory drug, improves nocturia (Saito M et al., Int J. Urol., 2005, vol. 12, p. 779); and that tramadol, which is an opioid non-narcotic analgesic, is effective against pollakiuria or urinary incontinence (WO 98/046216).

On the other hand, in regard to pyrazole derivatives (WO 08/105,383) or cyclohexane derivatives of the following Formula which has a sulfonyl group on the aromatic ring bound to the pyrazole ring (WO 00/066562), a compound having an analgesic effect has been reported, but there is no report which suggests that such a derivative is effective against a urine storage disorder(s).

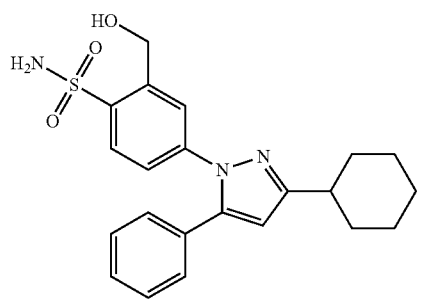 [SMILES: NS(=O)(=O)c1ccc(-n2nc(C3CCCCC3)cc2-c2ccccc2)cc1CO]

However, anticholinergic agents which have been used for urine storage disorders such as pollakiuria, urinary incontinence and/or urinary urgency have side effects due to their pharmacological action such as dry mouth; gastrointestinal system symptoms such as constipation; cardiovascular symptoms such as orthostatic hypotension; and urinary dysfunction such as urinary retention and residual urine, and therefore the use of anticholinergic agents are limited. In addition, loxoprofen has gastrointestinal adverse effects, and tramadol has gastrointestinal and central nervous system adverse effects that opioid drugs specifically have such as nausea, vomiting, dizziness and light-headedness. Therefore, the use of these drugs is also limited.

Accordingly, it could be helpful to provide a therapeutic agent or prophylactic agent effective for therapy of urine storage disorders, by which agent improvement of side effects due to an anticholinergic action is attained as well as which agent also has an analgesic effect.

SUMMARY

We discovered that novel cyclohexane derivatives having an excellent analgesic effect also have excellent therapeutic and prophylactic effects against urine storage disorders and are very unlikely to cause side effects due to an anticholinergic action.

That is, we provide a therapeutic agent or prophylactic agent for a urine storage disorder(s), said agent comprising as an effective ingredient a cyclohexane derivative represented by the Formula (I):

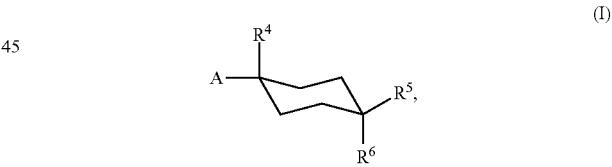

a pharmaceutically acceptable salt thereof, or a prodrug thereof, wherein A is a substituent represented by the Formula (IIa) or (IIb):

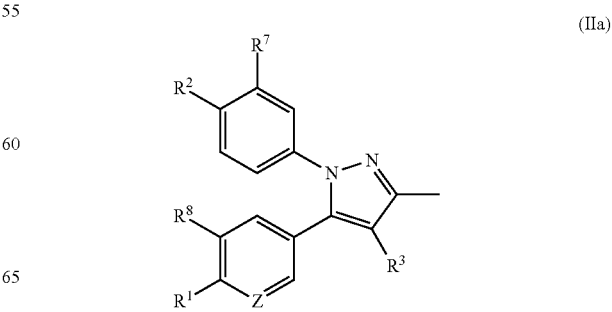

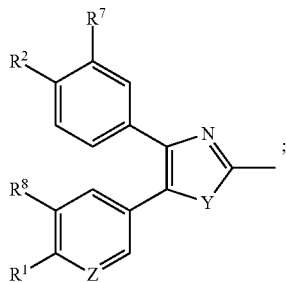
(IIb)

$R^1$ and $R^2$ are each independently a hydrogen atom, a chlorine atom, a $C_1$-$C_3$ haloalkyl group, a $C_1$-$C_4$ alkyl group or a $C_1$-$C_4$ alkoxy group; $R^3$ is a hydrogen atom or a chlorine atom; $R^4$ is a fluorine atom, a hydroxymethyl group or a hydroxyl group; $R^5$ and $R^6$ are each independently a hydrogen atom, a fluorine atom, a $C_1$-$C_3$ haloalkyl group, a carboxyl group, a methoxycarbonyl group, an ethoxycarbonyl group, a $C_1$-$C_4$ alkoxy group, a hydroxyl group or a $C_2$-$C_5$ alkylcarbonyloxy group, or optionally together form an oxo group; $R^7$ and $R^8$ are each independently a hydrogen atom or a fluorine atom; Y is an oxygen atom or a sulfur atom; Z is a nitrogen atom or a methine group.

In the above-described cyclohexane derivative, it is preferred that $R^1$ and $R^2$ be each independently a trifluoromethyl group, a methyl group or a methoxy group, and it is more preferred that $R^3$ be a hydrogen atom; $R^4$ be a hydroxymethyl group or a hydroxyl group; $R^5$ and $R^6$ be each independently a hydrogen atom, a fluorine atom, a trifluoromethyl group, a carboxyl group, a methoxy group, a hydroxyl group or an acetyloxy group (or may optionally together form an oxo group).

In addition, it is more preferred that the above-described therapeutic agent or prophylactic agent for a urine storage disorder(s) be a therapeutic agent or prophylactic agent for pollakiuria, urinary incontinence and/or urinary urgency.

The therapeutic agent or prophylactic agent for a urine storage disorder(s) has a remarkable therapeutic effect on a urine storage disorder(s) while ensuring the safety thanks to the fact that the agent is unlikely to cause side effects due to an anticholinergic action. Furthermore, since the agent also has an analgesic effect, pain is expected to be treated if the urine storage disorder(s) is(are) accompanied by pain.

BRIEF DESCRIPTION OF THE DRAWINGS

FIG. 1 shows the effect of intravenous administration of a cyclohexane derivative on the cyclophosphamide monohydrate (hereinafter "cyclophosphamide")-induced pollakiuria model rats.

DETAILED DESCRIPTION

The therapeutic agent or prophylactic agent for a urine storage disorder(s) comprises as an effective ingredient a cyclohexane derivative represented by Formula (I):

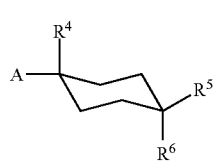
(I)

wherein A is a substituent represented by the following Formula (IIa) or (IIb):

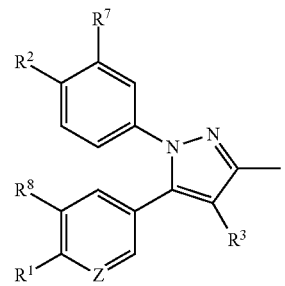
(IIa)

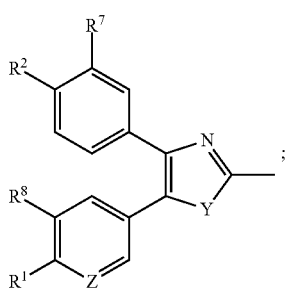
(IIb)

$R^1$ and $R^2$ are each independently a hydrogen atom, a chlorine atom, a $C_1$-$C_3$ haloalkyl group, a $C_1$-$C_4$ alkyl group or a $C_1$-$C_4$ alkoxy group; $R^3$ is a hydrogen atom or a chlorine atom; $R^4$ is a fluorine atom, a hydroxymethyl group or a hydroxyl group; $R^5$ and $R^6$ are each independently a hydrogen atom, a fluorine atom, a $C_1$-$C_3$ haloalkyl group, a carboxyl group, a methoxycarbonyl group, an ethoxycarbonyl group, a $C_1$-$C_4$ alkoxy group, a hydroxyl group or a $C_2$-$C_5$ alkylcarbonyloxy group, or $R^5$ and $R^6$ may optionally together form an oxo group; $R^7$ and $R^8$ are each independently a hydrogen atom or a fluorine atom; Y is an oxygen atom or a sulfur atom; and Z is a nitrogen atom or a methine group,
a pharmaceutically acceptable salt thereof or a prodrug thereof.

The term "$C_1$-$C_4$ alkyl group" means a linear, branched or cyclic alkyl group having 1 to 4 carbon atoms, and examples thereof include a methyl group, an ethyl group, an n-propyl group, an isopropyl group, a cyclopropyl group, a cyclopropylmethyl group, an n-butyl group, a sec-butyl group and a tert-butyl group.

The term "$C_1$-$C_4$ alkoxy group" means a linear, branched or cyclic alkyl-oxy group having 1 to 4 carbon atoms, and examples thereof include a methoxy group, an ethoxy group, an n-propyloxy group, an isopropyloxy group, a cyclopropyloxy group, an n-butoxy group, a sec-butoxy group and a tert-butoxy group.

The term "$C_1$-$C_3$ haloalkyl group" means a linear alkyl group having 1 to 3 carbon atoms wherein a part or all of the hydrogen atoms on the group are replaced by a halogen atom(s) (the halogen atom means a fluorine atom, a chlorine atom, a bromine atom or an iodine atom), and examples thereof include a monochloromethyl group, a monofluoromethyl group, a difluoromethyl group, a trifluoromethyl group, a trichloromethyl group and a pentafluoroethyl group.

Examples of the "$C_2$-$C_5$ alkylcarbonyloxy group" include an acetyloxy group, an ethanoyloxy group, a propanoyloxy group, an isopropanoyloxy group, a butanoyloxy group and an isobutanoyloxy group and a pivaloyloxy group.

In Formula (I), A is preferably Formula (IIa); Y is preferably an oxygen atom; and Z is preferably a methine group.

$R^1$ is preferably a hydrogen atom, a chlorine atom, a trifluoromethyl group, a methyl group, an ethyl group, an n-propyl group, an isopropyl group, a methoxy group, an ethoxy group, an n-propyloxy group or an isopropyloxy group, more preferably a trifluoromethyl group, a methyl group or a methoxy group, and still more preferably a methyl group.

$R^2$ is preferably a hydrogen atom, a chlorine atom, a trifluoromethyl group, a methyl group, an ethyl group, an n-propyl group, an isopropyl group, a methoxy group, an ethoxy group, an n-propyloxy group or an isopropyloxy group, and more preferably a methoxy group.

$R^3$ is preferably a hydrogen atom; and $R^4$ is preferably a hydroxymethyl group or a hydroxyl group, and more preferably a hydroxyl group.

$R^5$ is preferably a hydrogen atom, a fluorine atom, a trifluoromethyl group, a carboxyl group, a methoxy group, an ethoxy group, an n-propyloxy group, an isopropyloxy group, a hydroxyl group, an acetyloxy group, a propanoyloxy group, a butanoyloxy group or an isobutanoyloxy group, more preferably a hydrogen atom, a hydroxyl group or a carboxyl group, and still more preferably a hydroxyl group.

$R^6$ is preferably a hydrogen atom, a fluorine atom, a trifluoromethyl group, a carboxyl group, a methoxy group, an ethoxy group, an n-propyloxy group, an isopropyloxy group, a hydroxyl group, an acetyloxy group, a propanoyloxy group, a butanoyloxy group or an isobutanoyloxy group, more preferably a hydrogen atom or a hydroxyl group, and still more preferably a hydrogen atom. $R^5$ and $R^6$ may optionally together form an oxo group.

$R^7$ and $R^8$ are each preferably a hydrogen atom.

Among the compounds represented by Formula (I) or the pharmaceutically acceptable salts thereof (hereinafter referred to as "Compound (I)"), preferred specific examples are shown in Table 1, but our therapeutic agents are not limited by these.

TABLE 1

| Compound | Structural Formula |
| --- | --- |
| 1 | |
| 2 | |
| 3 | |
| 4 | |
| 5 | |
| 6 | |
| 7 | |
| 8 | |

TABLE 1-continued

| Compound | Structural Formula |
|---|---|
| 9 | 1-(4-methoxyphenyl)-5-(4-methylphenyl)-4-chloro-pyrazol-3-yl substituted 4-hydroxycyclohexan-1-ol |
| 10 | 1-(4-methoxyphenyl)-5-(4-methylphenyl)pyrazol-3-yl substituted 4-hydroxy-4-trifluoromethylcyclohexan-1-ol |
| 11 | 1-(4-methoxyphenyl)-5-(4-methylphenyl)pyrazol-3-yl substituted 1-fluoro-4-hydroxycyclohexane |
| 12 | 1-(4-methoxyphenyl)-5-(4-methylphenyl)pyrazol-3-yl substituted 4-hydroxycyclohexyl acetate |
| 13 | 1-(4-methoxyphenyl)-5-(4-methylphenyl)pyrazol-3-yl substituted 4-hydroxy-4-methoxycyclohexane |
| 14 | 1-(4-methoxyphenyl)-5-(4-methylphenyl)pyrazol-3-yl substituted 4-hydroxymethylcyclohexan-1-ol |
| 15 | 1-(4-methoxyphenyl)-5-(6-methylpyridin-3-yl)pyrazol-3-yl substituted 4-hydroxycyclohexan-1-ol |
| 16 | 1-(4-methoxyphenyl)-5-(4-methylphenyl)pyrazol-3-yl substituted 4-hydroxycyclohexane-1-carboxylic acid |
| 17 | 1-(4-methoxyphenyl)-5-(4-methylphenyl)pyrazol-3-yl substituted 4,4-difluoro-1-hydroxycyclohexane |
| 18 | 1-(4-methoxyphenyl)-5-(4-trifluoromethylphenyl)pyrazol-3-yl substituted 4-hydroxycyclohexan-1-ol |
| 19 | 1-(4-methoxyphenyl)-5-(4-trifluoromethylphenyl)pyrazol-3-yl substituted 4-hydroxycyclohexan-1-ol |
| 20 | 1-(4-methoxyphenyl)-5-(4-methylphenyl)pyrazol-3-yl substituted 4-hydroxy-4-hydroxymethylcyclohexane |

TABLE 1-continued

| Compound | Structural Formula |
|---|---|
| 21 | (4-methoxyphenyl, 4-chlorophenyl pyrazole, cyclohexane-1,4-diol) |
| 22 | (4-chlorophenyl, 4-methylphenyl pyrazole, cyclohexane-1,4-diol) |
| 23 | (4-chlorophenyl, 4-chlorophenyl pyrazole, cyclohexane-1,4-diol) |
| 24 | (4-chlorophenyl, 4-chlorophenyl pyrazole, cyclohexane-1,4-diol) |
| 25 | (phenyl, 4-chlorophenyl pyrazole, cyclohexane-1,4-diol) |
| 26 | (phenyl, 4-chlorophenyl pyrazole, cyclohexane-1,4-diol) |
| 27 | (4-methylphenyl, 4-methylphenyl pyrazole, cyclohexane-1,4-diol) |
| 28 | (4-methylphenyl, 4-methylphenyl pyrazole, cyclohexane-1,4-diol) |
| 29 | (phenyl, 4-methylphenyl pyrazole, cyclohexane-1,4-diol) |
| 30 | (phenyl, 4-methylphenyl pyrazole, cyclohexane-1,4-diol) |
| 31 | (4-methoxyphenyl, phenyl pyrazole, cyclohexane-1,4-diol) |
| 32 | (4-methoxyphenyl, phenyl pyrazole, cyclohexane-1,4-diol) |

TABLE 1-continued
| Compound | Structural Formula |
|---|---|
| 33 | 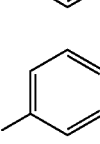 |
| 34 | 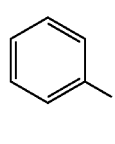 |
| 35 | 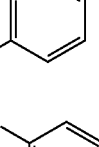 |
| 36 | 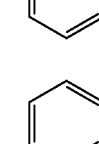 |
| 37 | 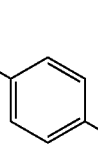 |
| 38 | 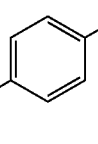 |
| 39 | 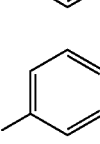 |
| 40 | 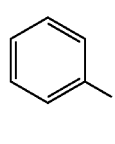 |
| 41 | 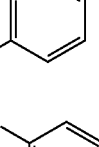 |
| 42 | 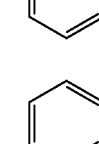 |
| 43 | 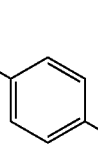 |
| 44 | 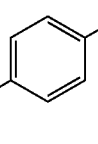 |

TABLE 1-continued

| Compound | Structural Formula |
|---|---|
| 45 | (structure) |
| 46 | (structure) |
| 47 | (structure) |
| 48 | (structure) |
| 49 | (structure) |
| 50 | (structure) |
| 51 | (structure) |
| 52 | (structure) |
| 53 | (structure) |
| 54 | (structure) |
| 55 | (structure) |

TABLE 1-continued

| Compound | Structural Formula |
|---|---|
| 56 | ![structure with H3CO-phenyl, pyrazole, H3C-phenyl-F, cyclohexane-diol (OH, OH)] |
| 57 | ![structure with H3CO-phenyl, pyrazole, H3C-phenyl, cyclohexane with OH and CO2CH3] |
| 58 | ![structure with H3CO-phenyl, pyrazole, H3C-phenyl, cyclohexane with OH and CO2Et] |

In cases where Compound (I) has an asymmetric carbon(s), all the enantiomers and mixtures thereof are within the scope of our therapeutic agents.

In cases where Compound (I) has a stereoisomer(s), all the stereoisomers and mixtures thereof are also within the scope of our therapeutic agents.

Examples of the "pharmaceutically acceptable salt" include inorganic acid salts such as hydrochloric acid salt, sulfuric acid salt, phosphoric acid salt and hydrobromic acid salt; organic acid salts such as oxalic acid salt, malonic acid salt, citric acid salt, fumaric acid salt, lactic acid salt, malic acid salt, succinic acid salt, tartaric acid salt, acetic acid salt, trifluoroacetic acid salt, maleic acid salt, gluconic acid salt, benzoic acid salt, ascorbic acid salt, methanesulfonic acid salt, p-toluenesulfonic acid salt and cinnamic acid salt; inorganic base salts such as sodium salt, potassium salt, calcium salt, magnesium salt and ammonium salt; and organic base salts such as methylamine salt, diethylamine salt, trimethylamine salt, triethylamine salt, pyridinium salt, triethanolamine salt, ethylenediamine salt and guanidine salt. Further, Compound (I) may form a hydrate or a solvate, and crystalline polymorphs are also included in Compound (I).

Compound (I) can be synthesized, for example, according to the production methods described below. The symbols in each reaction formula have the same meanings as defined above unless otherwise specified.

In cases where a raw material compound has a carboxyl group or a hydroxyl group, a protecting group as commonly used may be introduced thereto, and the protecting group may be removed as required after the reaction. Examples of the protecting group for a hydroxyl group include a $C_1$-$C_4$ alkyl group, a phenyl group, a trityl group, a $C_1$-$C_4$ aralkyl group (e.g., a benzyl group), an acyl group (e.g., a formyl group, an acetyl group or a benzoyl group), a $C_7$-$C_{10}$ aralkyl-carbonyl group (e.g., a benzylcarbonyl group) and a substituted silyl group (e.g., a trimethylsilyl group, a triethylsilyl group or a tert-butyldimethylsilyl group). Examples of the protecting group for a carboxyl group include a $C_1$-$C_4$ alkyl group.

The method to remove the protecting group varies depending on the type of the protecting group, and the removal may be carried out according to a known method as described in "Protective Groups In Organic Synthesis" (Wiley-Interscience) or a method similar thereto.

In the production methods described below, a salt may be used as a raw material compound. Examples of the salt include the same ones as the pharmaceutically acceptable salts described above.

Compound (I) obtained by the production methods described below may be isolated and purified according to known means, and examples of the known means include solvent extraction, recrystallization and chromatography.

In cases where Compound (I) has optical isomers, stereoisomers, regioisomers and/or rotamers, each of these may be obtained as a single compound by a known synthesis method and a known separation method.

(Production Method 1: Production Method of Compound (Ic), Compound (Id), Compound (Ie) and Compound (If))

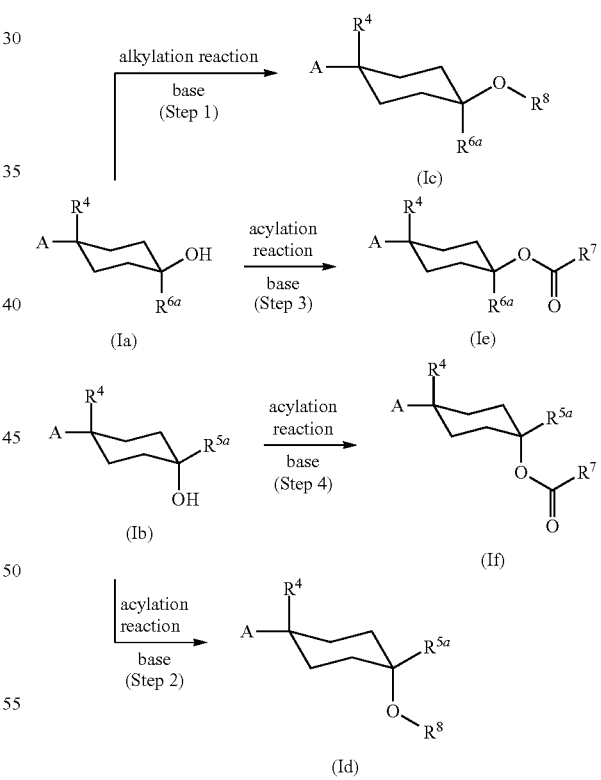

wherein $R^{5a}$ and $R^{6a}$ are each independently a hydrogen atom, a $C_1$-$C_3$ haloalkyl group, a carboxyl group or the like; $R^7$ and $R^8$ are each independently a $C_1$-$C_4$ alkyl group or the like; and the other symbols have the same meanings as defined above.

Compound (Ic) can be obtained by alkylation of Compound (Ia), and Compound (Id) can be obtained by alkylation of Compound (Ib). Compound (Ie) can be obtained by acylation of Compound (Ia), and Compound (If) can be obtained by acylation of Compound (Ib).

(Step 1 and Step 2)

The alkylation reaction of Compound (Ia) or Compound (Ib) is usually performed by reacting Compound (Ia) or Compound (Ib) with an alkyl halide in a solvent in the presence of a base. As the solvent, a solvent that does not inhibit the reaction is appropriately selected. Examples of the solvent that does not inhibit the reaction include ethers such as tetrahydrofuran, 1,4-dioxane and ethylene glycol dimethyl ether; acetone; acetonitrile; and N,N-dimethylformamide. A mixed solvent of these may also be used as the solvent.

Examples of the base include alkali metal hydrogen carbonates such as sodium hydrogen carbonate and potassium hydrogen carbonate; alkali metal carbonates such as potassium carbonate and cesium carbonate; amines such as triethylamine, diisopropylethylamine and pyridine; potassium tert-butoxide; and sodium hydride.

The amount of the base to be used is preferably 0.5 to 6 mol, more preferably 0.8 to 3 mol, with respect to 1 mol of Compound (Ia) or Compound (Ib).

The amount of the alkyl halide to be used is preferably 0.5 to 5 mol, more preferably 0.8 to 2 mol, with respect to 1 mol of Compound (Ia) or Compound (Ib).

The reaction temperature of the alkylation reaction is preferably −78° C. to 200° C., more preferably −20° C. to 100° C.

The reaction time of the alkylation reaction varies depending on the reaction conditions, and is preferably 5 minutes to 78 hours, more preferably 30 minutes to 48 hours.

(Step 3 and Step 4)

The acylation reaction of Compound (Ia) or Compound (Ib) is usually performed by reacting Compound (Ia) or Compound (Ib) with an acylating agent, such as an acid halide or an acid anhydride, in a solvent in the presence of a base. As the solvent, a solvent that does not inhibit the reaction is appropriately selected. Examples of the solvent that does not inhibit the reaction include halogenated hydrocarbons such as dichloromethane, chloroform, carbon tetrachloride and 1,2-dichloroethane; and ethers such as tetrahydrofuran, 1,2-dimethoxyethane and 1,4-dioxane. A mixed solvent of these may also be used as the solvent.

Examples of the base include pyridine, triethylamine, diisopropylethylamine, N,N-dimethylaminopyridine and the like.

The amount of the acid halide or the acid anhydride to be used is preferably 0.5 to 3 mol, more preferably 0.8 to 1.5 mol, with respect to 1 mol of Compound (Ia) or Compound (Ib).

The amount of the base to be used is preferably 0.1 to 6 mol, more preferably 0.8 to 3 mol, with respect to 1 mol of Compound (Ia) or Compound (Ib).

The reaction temperature of the acylation reaction is preferably −20° C. to 150° C., more preferably 0° C. to 100° C.

The reaction time of the acylation reaction varies depending on the reaction conditions, and is preferably 5 minutes to 72 hours, more preferably 30 minutes to 48 hours.

(Production Method 2: Production Method of Compound (Ih))

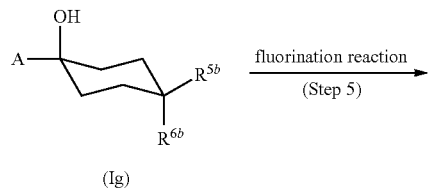

(Ig)

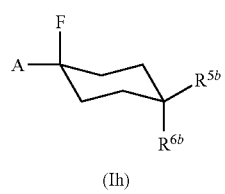

(Ih)

wherein $R^{5b}$ and $R^{6b}$ are each independently a hydrogen atom, a fluorine atom, a $C_1$-$C_3$ haloalkyl group, a $C_1$-$C_4$ alkoxy group, a $C_2$-$C_5$ alkylcarbonyloxy group or the like; and the other symbols have the same meanings as defined above.

Compound (Ih) can be obtained by fluorination of Compound (Ig).

(Step 5)

The fluorination reaction of Compound (Ig) is usually performed by reacting Compound (Ig) with a fluorinating agent in a solvent. As the solvent, a solvent that does not inhibit the reaction is appropriately selected. Examples of the solvent that does not inhibit the reaction include hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile. A mixed solvent of these may also be used as the solvent.

Examples of the fluorinating agent include alkylaminosulfur trifluorides such as (dimethylamino)sulfur trifluoride (DAST) and bis(2-methoxyethyl)aminosulfur trifluoride acid.

The amount of the fluorinating agent to be used is preferably 0.25 to 20 mol, more preferably 0.5 to 4 mol, with respect to 1 mol of Compound (Ig).

The reaction temperature of the fluorination reaction is preferably −20° C. to 150° C., more preferably 0° C. to 100° C.

The reaction time of the fluorination reaction varies depending on the reaction conditions, and is preferably 5 minutes to 72 hours, more preferably 30 minutes to 48 hours.

(Production Method 3: Production Method of Compound (Ij))

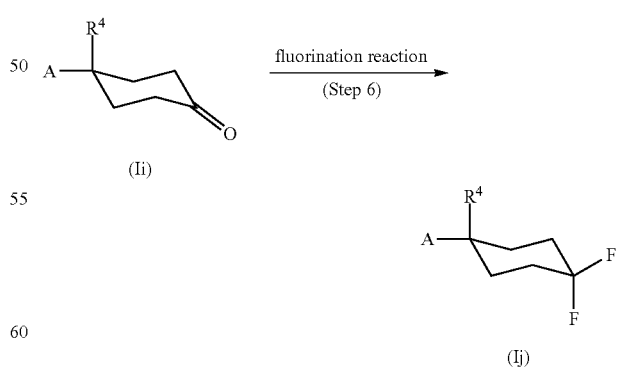

wherein the symbols have the same meanings as defined above.

Compound (Ij) can be obtained by fluorination of Compound (II).

(Step 6)

The fluorination reaction of Compound (II) is usually performed by reacting Compound (II) with a fluorinating agent in a solvent. As the solvent, a solvent that does not inhibit the reaction is appropriately selected. Examples of the solvent that does not inhibit the reaction include hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile. Alternatively, a mixed solvent of these may be used as the solvent.

Examples of the fluorinating agent include alkylaminosulfur trifluorides such as (dimethylamino)sulfur trifluoride (DAST) and bis(2-methoxyethyl)aminosulfur trifluoride acid.

The amount of the fluorinating agent to be used is preferably 0.25 to 20 mol, more preferably 0.5 to 4 mol, with respect to 1 mol of Compound (Ii).

The reaction temperature of the fluorination reaction is preferably −20° C. to 150° C., more preferably 0° C. to 100° C.

The reaction time of the fluorination reaction varies depending on the reaction conditions, and is preferably 5 minutes to 72 hours, more preferably 30 minutes to 48 hours.

(Production Method 4: Production Method of Compound (Ik) and Compound (Il))

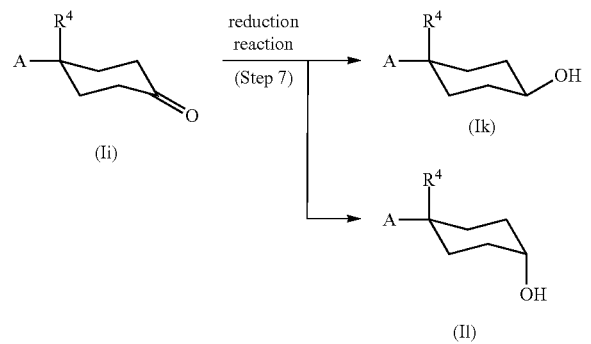

wherein the symbols have the same meanings as defined above.

Compound (Ik) and Compound (Il) can be obtained by reducing Compound (Ii).

(Step 7)

The reduction reaction of Compound (Ii) is usually performed by reacting Compound (Ii) with a reducing agent in a solvent. As the solvent, a solvent that does not inhibit the reaction is appropriately selected. Examples of the solvent that does not inhibit the reaction include hydrocarbons such as octane, hexane, benzene and toluene; ethers such as tetrahydrofuran, 1,4-dioxane, ethylene glycol dimethyl ether and diethyl ether; and alcohols such as methanol, ethanol and isopropyl alcohol. A mixed solvent of these may also be used as the solvent.

Examples of the reducing agent include sodium borohydride, lithium borohydride, diisobutylaluminium hydride, lithium aluminum hydride, lithium triethyl hydride, sodium bis(2-methoxyethoxy)aluminum hydride and borane complexes.

The amount of the reducing agent to be used is preferably 0.25 to 100 mol, more preferably 0.5 to 20 mol, with respect to 1 mol of Compound (Ii).

The reaction temperature of the reduction reaction is preferably −78° C. to 150° C., more preferably −78° C. to 100° C.

The reaction time of the reduction reaction varies depending on the reaction conditions such as the reaction temperature, the amount of the reducing agent and the like, and is preferably 5 minutes to 72 hours, more preferably 30 minutes to 24 hours.

(Production Method 5: Production Method of Compound (Im) and Compound (In))

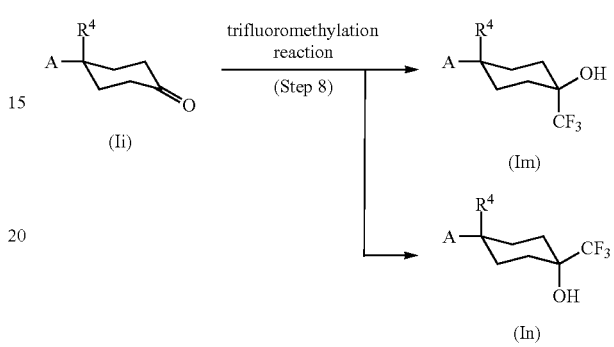

wherein the symbols have the same meanings as defined above.

Compound (Im) and Compound (In) can be obtained by trifluoromethylation of Compound (Ii).

(Step 8)

Examples of the trifluoromethylating agent include organosilicon compounds such as (trifluoromethyl)trimethylsilane. The trifluoromethylation reaction using an organosilicon compound may be carried out according to a method as described in *Journal of the American Chemical Society*, 1989, Vol. 39, pp. 393-395 or a method similar thereto.

(Production Method 6: Production Method of Compound (Io))

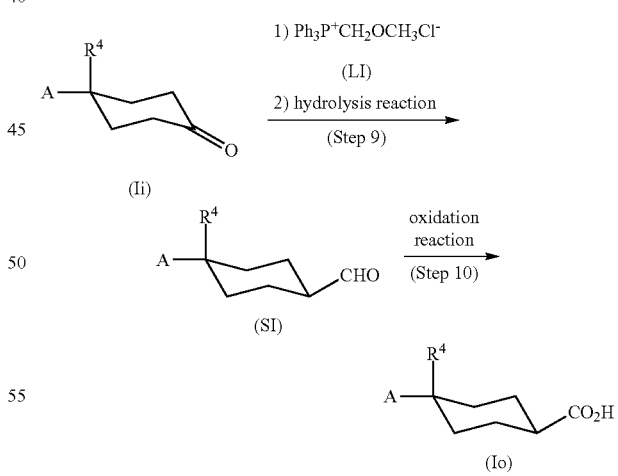

wherein the symbols have the same meanings as defined above.

Compound (SI) can be obtained by allowing a Wittig reagent (LI) to act on Compound (II), and then hydrolyzing the resulting compound. As the Wittig reagent, a commercially available compound may be used, or it may be synthesized according to a method obvious to those skilled in the art. Compound (Io) can be obtained by oxidizing Compound (SI).

(Step 9)

The Wittig reaction of Compound (Ii) is usually performed by reacting Compound (Ii) with a Wittig reagent in a solvent in the presence of a base. As the solvent, a solvent that does not inhibit the reaction is appropriately selected. Examples of the solvent that does not inhibit the reaction include hydrocarbons such as octane, hexane, benzene and toluene; and ethers such as tetrahydrofuran, 1,4-dioxane, ethylene glycol dimethyl ether and diethyl ether. A mixed solvent of these may also be used as the solvent.

Examples of the base include lithium diisopropylamide, potassium tert-butoxide, sodium hydride, phenyllithium and tert-butyllithium.

The amount of the base to be used is preferably 0.5 to 3 mol, more preferably 0.8 to 2 mol, with respect to 1 mol of Compound (Ii).

The amount of Compound (LI) to be used is preferably 0.5 to 3 mol, more preferably 0.8 to 2 mol, with respect to 1 mol of Compound (Ii).

The reaction temperature of the Wittig reaction is preferably −78° C. to 100° C., more preferably −78° C. to 50° C.

The reaction time of the Wittig reaction varies depending on the reaction conditions such as the reaction temperature, and is preferably 5 minutes to 48 hours, more preferably 30 minutes to 24 hours.

The hydrolysis reaction to obtain Compound (SI) is performed in an appropriately selected solvent that does not inhibit the reaction. Examples of the solvent that does not inhibit the reaction include ethers such as tetrahydrofuran, 1,4-dioxane and ethylene glycol dimethyl ether; alcohols such as methanol, ethanol and tert-butanol; acetonitrile; and water. A mixed solvent of these may also be used as the solvent.

The concentration of the acid which is used in the hydrolysis reaction is preferably 0.1 M to 12 M, and the amount of the acid to be used is preferably from 1 mol to an excess amount with respect to 1 mol of Compound (Ii).

Examples of the acid which is used in the hydrolysis reaction include inorganic acids such as hydrochloric acid and sulfuric acid; and organic acids such as acetic acid.

The reaction temperature of the hydrolysis reaction is preferably −20° C. to 200° C., more preferably 0° C. to 100° C.

The reaction time of the hydrolysis reaction varies depending on the reaction conditions, and is preferably 5 minutes to 48 hours, more preferably 30 minutes to 24 hours.

(Step 10)

Examples of the oxidizing agent which is used in oxidation reaction of Compound (SI) include chromium (VI) oxide-acetic acid, Jones reagent, sodium chlorite and the like. The oxidation reaction may be carried out according to a known method.

(Production Method 7: Production Method of Compound (Ii))

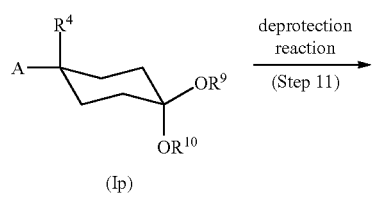

(Ip)

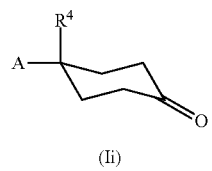

(Ii)

wherein $R^9$ and $R^{10}$ are each independently a methyl group, an ethyl group, an n-propyl group, an isopropyl group, an n-butyl group, a sec-butyl group or a tert-butyl group or the like, or $R^9$ and $R^{10}$ may together form an ethylene group (—CH$_2$CH$_2$—), a propylene group (—CH$_2$CH$_2$CH$_2$—) or the like; and the other symbols have the same meanings as defined above.

Compound (Ii) can be obtained by deprotection of Compound (Ip).

(Step 11)

The deprotection reaction of Compound (Ip) may be carried out according to a method as described in "Protective Groups In Organic Synthesis" (Wiley-Interscience) or a method similar thereto.

(Production Method 8: Production Method of Compound (IIIb))

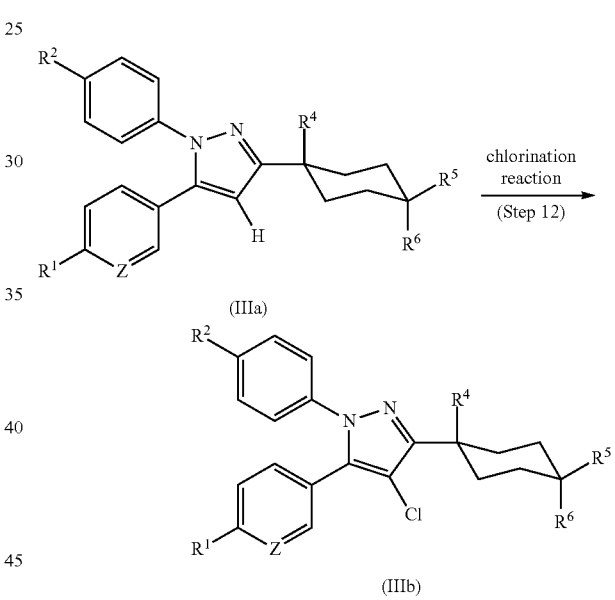

wherein the symbols have the same meanings as defined above.

Compound (IIIb) can be obtained by chlorination of Compound (IIIa).

(Step 12)

The chlorination reaction of Compound (IIIa) is usually performed by reacting Compound (IIIa) with a chlorinating agent in a solvent. As the solvent, a solvent that does not inhibit the reaction is appropriately selected. Examples of the solvent that does not inhibit the reaction include halogenated hydrocarbons such as dichloromethane, chloroform, carbon tetrachloride and 1,2-dichloroethane; acetonitrile; and ethyl acetate. A mixed solvent of these may also be used as the solvent.

Examples of the chlorinating agent include N-chlorosuccinimide (NCS).

The amount of the chlorinating agent to be used is preferably 0.5 to 2 mol, more preferably 0.8 to 1.2 mol, with respect to 1 mol of Compound (Ma).

The reaction temperature of the chlorination reaction is preferably 0° C. to 200° C., more preferably 0° C. to 120° C.

The reaction time of the chlorination reaction varies depending on the reaction conditions such as the reaction temperature, and is preferably 5 minutes to 72 hours, more preferably 30 minutes to 48 hours.

(Production Method 9: Production Method of Compound (IIIa))

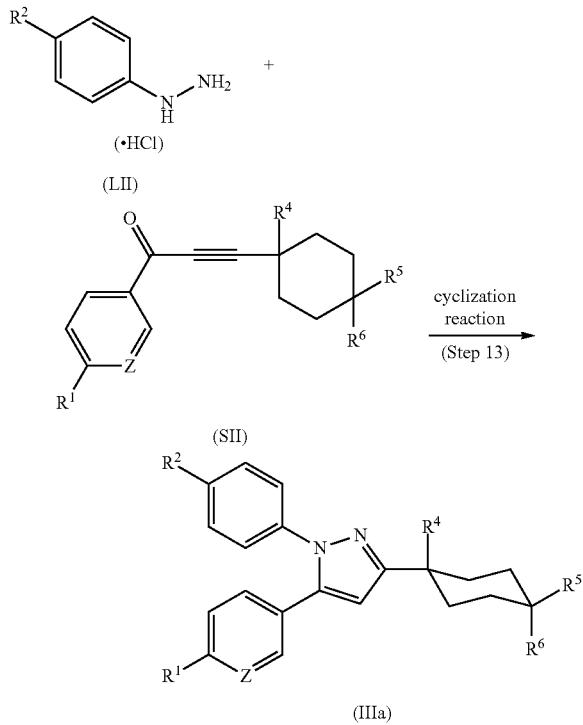

wherein the symbols have the same meanings as defined above.

Compound (IIIa) can be obtained by cyclization of Compound (LII) with Compound (SII). As Compound (LII), a commercially available compound may be used, or it may be synthesized according to a known method.

(Step 13)

The cyclization reaction of Compound (LII) with Compound (SII) is usually performed in an appropriately selected solvent that does not inhibit the reaction. Examples of the solvent that does not inhibit the reaction include alcohols such as methanol, ethanol and isopropyl alcohol; halogenated hydrocarbons such as dichloromethane, chloroform, carbon tetrachloride and 1,2-dichloroethane; ethers such as tetrahydrofuran, 1,2-dimethoxyethane and 1,4-dioxane; benzene; toluene; acetic acid; and water. A mixed solvent of these may also be used as the solvent.

The amount of Compound (LII) to be used is preferably 0.5 to 1.5 mol, more preferably 0.8 to 1.2 mol, with respect to 1 mol of Compound (SII).

In the cyclization reaction, a catalyst may be used, and examples of the catalyst include organic bases such as triethylamine and pyridine; inorganic acids such as hydrochloric acid and sulfuric acid; and organic acids such as acetic acid.

The amount of the catalyst to be used is preferably 0.1 to 3 mol with respect to 1 mol of Compound (SIT).

The reaction temperature of the cyclization reaction is preferably 0° C. to 200° C., more preferably 0° C. to 120° C.

The reaction time of the cyclization reaction varies depending on the reaction conditions such as the reaction temperature, and is preferably 5 minutes to 72 hours, more preferably 30 minutes to 48 hours.

(Production Method 10: Production Method of Compound (IV))

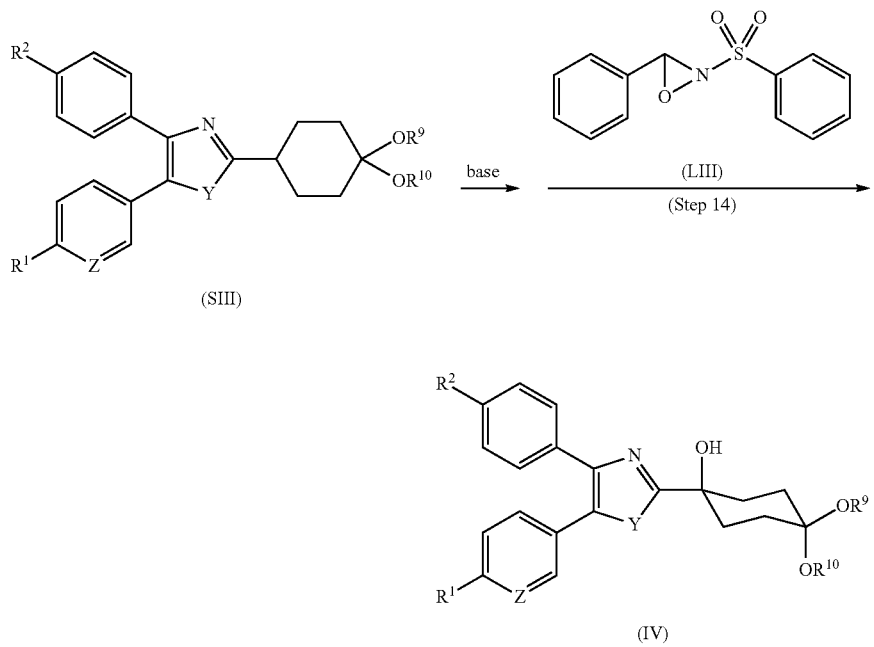

wherein the symbols have the same meanings as defined above.

Compound (IV) can be obtained by deprotonation and oxidization of Compound (SIII. The oxidation reaction may be carried out according to a method as described in *Tetrahedron,* 1989, Vol. 45, pp. 5703-5742 or a method similar thereto.

(Step 14)

The deprotonation reaction and the oxidation reaction of Compound (SIII) are usually performed by reacting Compound (SIII) with a base and an oxidizing agent in an anhydrous solvent. As the solvent, a solvent that does not inhibit the reactions is appropriately selected. Examples of the solvent that does not inhibit the reactions include hydrocarbons such as octane, hexane and heptane; and ethers such as tetrahydrofuran, 1,4-dioxane, ethylene glycol dimethyl ether and diethyl ether. A mixed solvent of these may also be used as the solvent.

Examples of the base include butyllithiums such as n-butyllithium, sec-butyllithium and tert-butyllithium.

The amount of the base to be used is preferably 0.8 to 5 mol, more preferably 0.9 to 3 mol, with respect to 1 mol of Compound (SIII).

The amount of Compound (LIII) to be used is preferably 0.8 to 5 mol, more preferably 0.9 to 3 mol, with respect to 1 mol of Compound (SIII).

Examples of the oxidizing agent which is used in the oxidation reaction include 3-phenyl-2-(phenylsulfonyl)-1,2-oxaziridine.

The reaction temperature of the deprotonation reaction and the oxidation reaction is preferably −78° C. to 150° C., more preferably 0° C. to 50° C.

The reaction time of the deprotonation reaction and the oxidation reaction varies depending on the reaction conditions, and is preferably 5 minutes to 72 hours, more preferably 30 minutes to 48 hours.

(Production Method 11: Production Method of Intermediate Compound (VI))

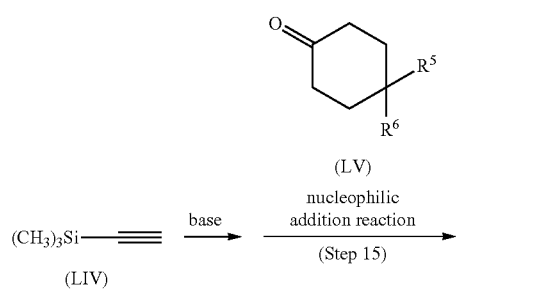

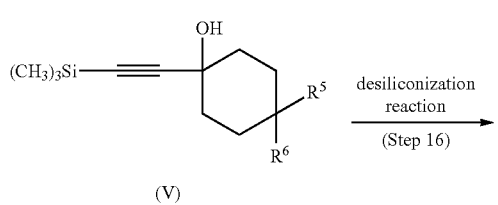

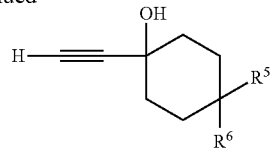

wherein the symbols have the same meanings as defined above.

Compound (VI) can be obtained by solvolysis of Compound (V) which has been obtained by reacting Compound (LIV) and Compound (LV). As Compound (LIV) and Compound (LV), commercially available compounds may be used, or they may be synthesized according to known methods.

(Step 15)

The reaction between Compound (LIV) and Compound (LV) is usually performed in an anhydrous solvent in the presence of a base; and, as the solvent, a solvent that does not inhibit the reaction is appropriately selected. Examples of the solvent that does not inhibit the reaction include hydrocarbons such as octane, hexane, benzene and toluene; and ethers such as tetrahydrofuran, 1,4-dioxane, ethylene glycol dimethyl ether and diethyl ether. A mixed solvent of these may also be used as the solvent.

Examples of the base include alkyllithiums such as methyllithium and n-butyllithium; and salts of dialkylamines such as lithium diisopropylamide, lithium bis(trimethylsilyl) amide and potassium bis(trimethylsilyl)amide.

The amount of the base to be used is preferably 0.8 to 5 mol, more preferably 0.9 to 3 mol, with respect to 1 mol of Compound (LIV).

The amount of Compound (LV) to be used is preferably 0.8 to 5 mol, more preferably 0.9 to 3 mol, with respect to 1 mol of Compound (LIV).

The reaction temperature of the reaction between Compound (LIV) and Compound (LV) is preferably −78° C. to 150° C., more preferably −78° C. to 100° C.

The reaction time of the reaction between Compound (LIV) and Compound (LV) varies depending on the reaction conditions, and is preferably 5 minutes to 72 hours, more preferably 30 minutes to 48 hours.

(Step 16)

The solvolysis reaction is usually performed in a solvent in the presence of a base; and, as the solvent, a solvent that does not inhibit the reaction is appropriately selected. Examples of the solvent that does not inhibit the reaction include alcohols such as methanol and ethanol; and water. A mixed solvent of these may also be used as the solvent.

Examples of the base include potassium carbonate, sodium carbonate, potassium hydroxide and sodium hydroxide.

The amount of the base to be used is preferably 0.5 to 10 mol, more preferably 0.8 to 3 mol, with respect to 1 mol of Compound (V).

The reaction temperature of the solvolysis reaction is preferably −20° C. to 150° C., more preferably 0° C. to 100° C.

The reaction time of the solvolysis reaction varies depending on the reaction conditions, and is preferably 5 minutes to 72 hours, more preferably 30 minutes to 48 hours.

(Production Method 12: Production Method of Intermediate Compound (SIIa))

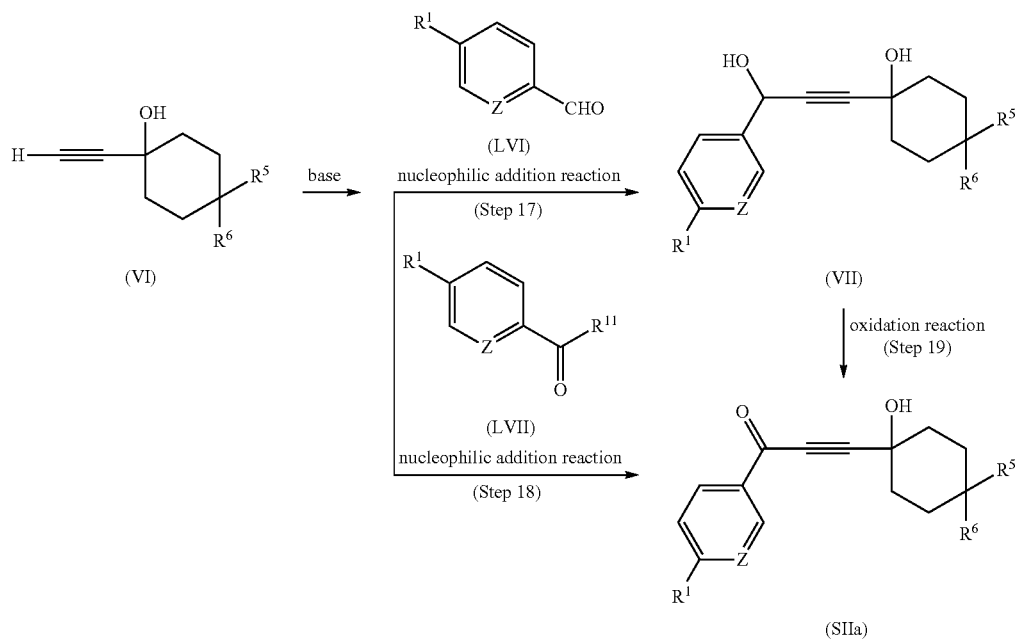

wherein $R^{11}$ represents a chlorine atom, an imidazolyl group, an N-methoxy-N-methylamino group, an alkoxy group such as a methoxy group or an ethoxy group, or the like; and the other symbols have the same meanings as defined above.

Compound (SIIa) can be obtained by oxidizing Compound (VII) which has been obtained by reacting Compound (VI) and Compound (LVI). Compound (SIIa) can also be obtained by reacting Compound (VI) and Compound (LVII). As Compound (LVI) and Compound (LVII), commercially available compounds may be used, or they may be synthesized according to a known method.

(Step 17 or Step 18)

The reaction between Compound (VI) and Compound (LVI) or Compound (LVII) is usually performed in an anhydrous solvent in the presence of a base; and, as the solvent, a solvent that does not inhibit the reaction is appropriately selected. Examples of the solvent that does not inhibit the reaction include hydrocarbons such as octane, hexane, benzene and toluene; and ethers such as tetrahydrofuran, 1,4-dioxane, ethylene glycol dimethyl ether and diethyl ether. A mixed solvent of these may also be used as the solvent.

Examples of the base include alkyllithiums such as methyllithium and n-butyllithium; and salts of dialkylamines such as lithium diisopropylamide, lithium bis(trimethylsilyl)amide and potassium bis(trimethylsilyl)amide.

The amount of the base to be used is preferably 0.8 to 5 mol, more preferably 0.9 to 3 mol, with respect to 1 mol of Compound (VI).

The amount of Compound (LVI) to be used in Step 17 or Compound (LVII) to be used in Step 18 is preferably 0.8 to 5 mol, more preferably 0.9 to 3 mol, with respect to 1 mol of Compound (VI).

The reaction temperature of the reaction between Compound (VI) and Compound (LVI) or Compound (LVII) is preferably −78° C. to 150° C., more preferably 0° C. to 50° C.

The reaction time of the reaction between Compound (VI) and Compound (LVI) or Compound (LVII) varies depending on the reaction conditions, and is preferably 5 minutes to 72 hours, more preferably 30 minutes to 48 hours.

(Step 19)

The oxidation reaction of Compound (VII) is usually performed by reacting Compound (VII) with an oxidizing agent in a solvent. As the solvent, a solvent that does not inhibit the reaction is appropriately selected. Examples of the solvent that does not inhibit the reaction include hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile; trifluoroacetic acid; pyridine; acetone; and the like. A mixed solvent of these may also be used as the solvent.

Examples of the oxidizing agent include commercially available reagents such as manganese dioxide, sulfur trioxide-pyridine, activated dimethyl sulfoxide and Dess-Martin reagent.

The amount of the oxidizing agent to be used is preferably 0.5 to 3 mol, more preferably 0.8 to 2 mol, with respect to 1 mol of Compound (VII).

The reaction temperature of the oxidation reaction varies depending on the type of the oxidizing agent, and is preferably −78° C. to 100° C., more preferably −78° C. to 40° C.

The reaction time of the oxidation reaction varies depending on the reaction conditions such as the type of the oxidizing agent, the reaction temperature and the like, and is preferably 5 minutes to 72 hours, more preferably 1 hour to 24 hours.

(Production Method 13: Production Method of Intermediate Compound (IX))

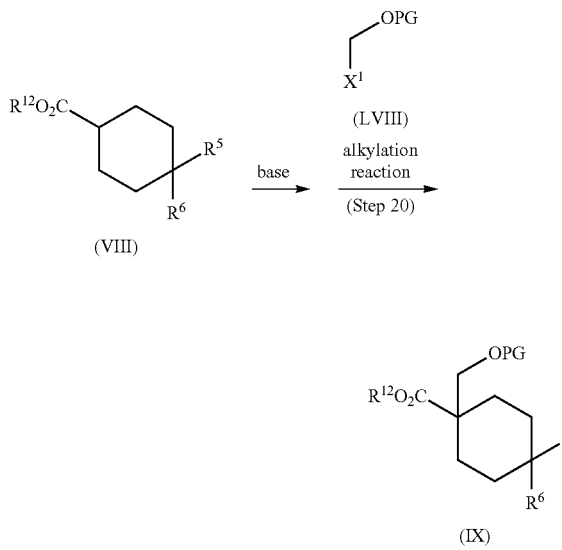

wherein $X^1$ is a halogen atom; PG is a protecting group such as methyl or benzyl; $R^{12}$ is an alkoxy group such as a methoxy group or an ethoxy group, or the like; and the other symbols have the same meanings as defined above.

Compound (IX) can be obtained by reacting Compound (VIII) and Compound (LVIII). As Compound (VIII) and Compound (LVIII), commercially available compounds may be used, or they may be synthesized according to a method obvious to those skilled in the art.

(Step 20)

The reaction between Compound (VIII) and Compound (LVIII) is usually performed in an anhydrous solvent in the presence of a base; and, as the solvent, a solvent that does not inhibit the reaction is appropriately selected. Examples of the solvent that does not inhibit the reaction include hydrocarbons such as octane, hexane, benzene and toluene; and ethers such as tetrahydrofuran, 1,4-dioxane, ethylene glycol dimethyl ether and diethyl ether. A mixed solvent of these may also be used as the solvent.

Examples of the base include lithium diisopropylamide, lithium bis(trimethylsilyl)amide and potassium bis(trimethylsilyl)amide.

The amount of the base to be used is preferably 0.8 to 4 mol, more preferably 0.9 to 3.5 mol, with respect to 1 mol of Compound (VIII).

The amount of Compound (LVIII) to be used is preferably 0.8 to 5 mol, more preferably 0.9 to 3 mol, with respect to 1 mol of Compound (VIII).

The reaction temperature of the reaction between Compound (VIII) and Compound (LVIII) is preferably −78° C. to 150° C., more preferably 0° C. to 50° C.

The reaction time of the reaction between Compound (VIII) and Compound (LVIII) varies depending on the reaction conditions, and is preferably 5 minutes to 72 hours, more preferably 30 minutes to 48 hours.

(Production Method 14: Production Method of Intermediate Compound (XI))

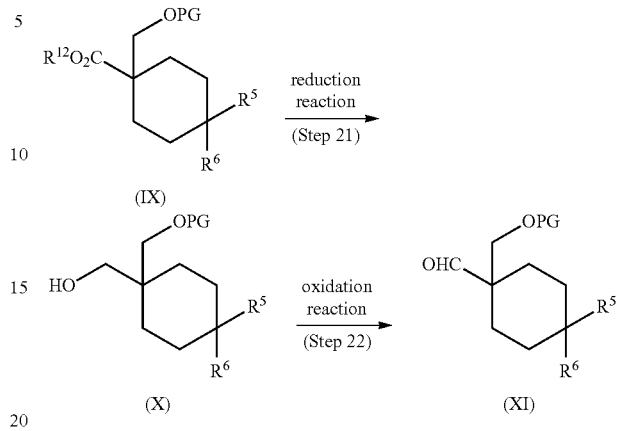

wherein the symbols have the same meanings as defined above.

Compound (XI) can be obtained by oxidizing Compound (X) which has been obtained by reducing Compound (IX).

(Step 21)

The reduction reaction of Compound (IX) is usually performed by reacting Compound (IX) with a reducing agent in a solvent. As the solvent, a solvent that does not inhibit the reaction is appropriately selected. Examples of the solvent that does not inhibit the reaction include hydrocarbons such as octane, hexane, benzene and toluene; ethers such as tetrahydrofuran, 1,4-dioxane, ethylene glycol dimethyl ether and diethyl ether; and alcohols such as methanol, ethanol and isopropyl alcohol. A mixed solvent of these may also be used as the solvent.

Examples of the reducing agent include lithium borohydride, diisobutylaluminium hydride, lithium aluminum hydride, lithium triethyl hydride, sodium bis(2-methoxyethoxy)aluminum hydride and borane complexes.

The amount of the reducing agent to be used is preferably 0.25 to 100 mol, more preferably 0.5 to 20 mol, with respect to 1 mol of Compound (IX).

The reaction temperature of the reduction reaction is preferably −78° C. to 150° C., more preferably −78° C. to 100° C.

The reaction time of the reduction reaction varies depending on the reaction conditions such as the reaction temperature, the amount of the reducing agent and the like, and is preferably 5 minutes to 72 hours, more preferably 30 minutes to 24 hours.

(Step 22)

The oxidation reaction of Compound (X) is usually performed by reacting Compound (X) with an oxidizing agent in a solvent. As the solvent, a solvent that does not inhibit the reaction is appropriately selected. Examples of the solvent that does not inhibit the reaction include trifluoroacetic acid; pyridine; acetone; hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile. A mixed solvent of these may also be used as the solvent.

Examples of the oxidizing agent include commercially available reagents such as sulfur trioxide-pyridine, activated dimethyl sulfoxide and Dess-Martin reagent.

The amount of the oxidizing agent to be used is preferably 0.5 to 3 mol, more preferably 0.8 to 2 mol, with respect to 1 mol of Compound (X).

The reaction temperature of the oxidation reaction varies depending on the type of the oxidizing agent, and is preferably −78° C. to 100° C., more preferably −78° C. to 40° C.

The reaction time of the oxidation reaction varies depending on the reaction conditions such as the type of the oxidizing agent, reaction temperature and the like, and is preferably 5 minutes to 72 hours, more preferably 1 hour to 24 hours.

(Production Method 15: Production Method of Intermediate Compound (XII))

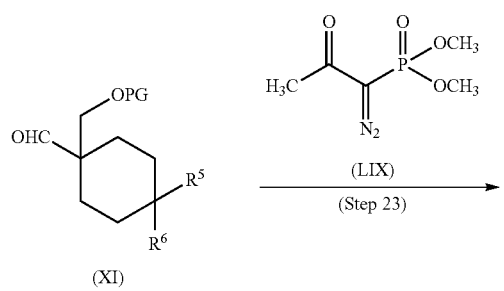

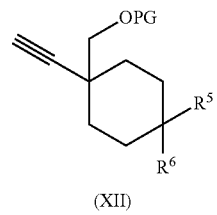

wherein the symbols have the same meanings as defined above.

(Step 23)

Compound (XII) can be obtained by converting Compound (XI) to an alkyne. Examples of the reagent which is used in the conversion reaction include dimethyl-1-diazo-2-oxopropylphosphonate. The conversion reaction may be carried out according to a method as described in *Tetrahedron Letters*, 2006, Vol. 47, pp. 1729-1731 or a method similar thereto.

(Production Method 16: Production Method of Intermediate Compound (SIIb))

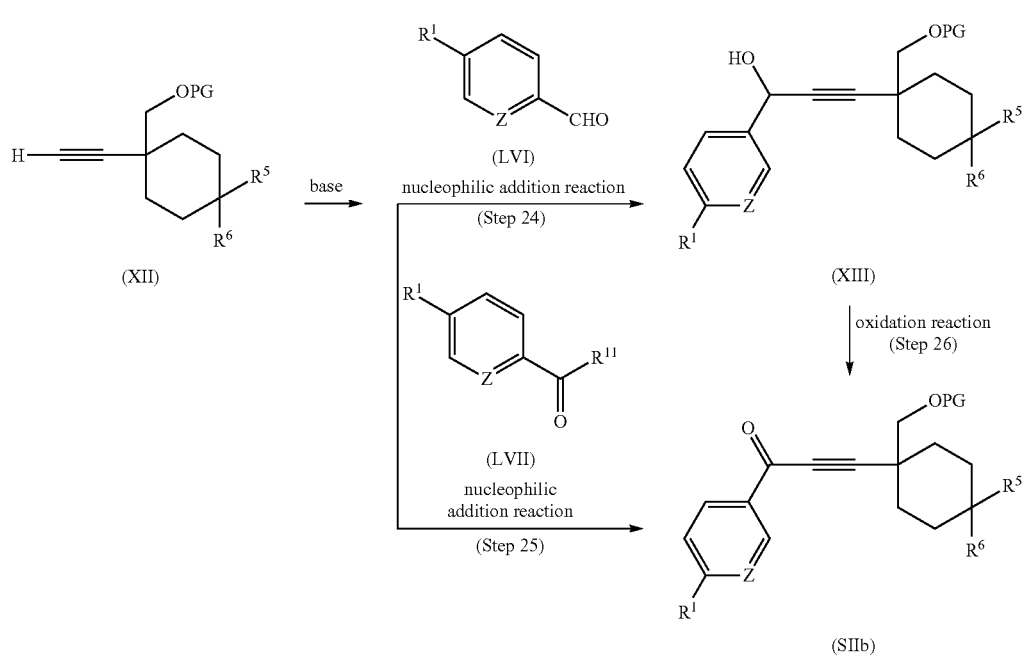

wherein the symbols have the same meanings as defined above.

Compound (SIIb) can be obtained by oxidizing Compound (XIII) which has been obtained by reacting Compound (XII) and Compound (LVI). Compound (SIIb) can also be obtained by reacting Compound (XII) and Compound (LVII). As Compound (LVI) and Compound (LVII), commercially available compounds may be used, or they may be synthesized according to a known method.

(Step 24 or Step 25)

The nucleophilic addition reaction of Compound (XII) is usually performed in an anhydrous solvent in the presence of a base; and, as the solvent, a solvent that does not inhibit the reaction is appropriately selected. Examples of the solvent that does not inhibit the reaction include hydrocarbons such as octane, hexane, benzene and toluene; and ethers such as tetrahydrofuran, 1,4-dioxane, ethylene glycol dimethyl ether and diethyl ether. A mixed solvent of these may also be used as the solvent.

Examples of the base include alkyllithiums such as methyllithium and n-butyllithium; and salts of dialkylamines such as lithium diisopropylamide, lithium bis(trimethylsilyl)amide and potassium bis(trimethylsilyl)amide.

The amount of the base to be used is preferably 0.8 to 5 mol, more preferably 0.9 to 3 mol, with respect to 1 mol of Compound (XII).

The amount of Compound (LVI) or Compound (LVII) to be used is preferably 0.8 to 5 mol, more preferably 0.9 to 3 mol, with respect to 1 mol of Compound (XII).

The reaction temperature of the nucleophilic addition reaction is preferably −78° C. to 150° C., more preferably 0° C. to 50° C.

The reaction time of the nucleophilic addition reaction varies depending on the reaction conditions, and is preferably 5 minutes to 72 hours, more preferably 30 minutes to 48 hours.

(Step 26)

The oxidation reaction of Compound (XIII) is usually performed by reacting Compound (XIII) with an oxidizing agent in a solvent. As the solvent, a solvent that does not inhibit the reaction is appropriately selected. Examples of the solvent that does not inhibit the reaction include trifluoroacetic acid; pyridine; acetone; hydrocarbons such as octane, hexane, benzene and toluene; halogenated hydrocarbons such as dichloromethane, chloroform, carbon tetrachloride and 1,2-dichloroethane; ethers such as tetrahydrofuran, 1,2-dimethoxyethane and 1,4-dioxane; and alkyl nitriles such as acetonitrile. A mixed solvent of these may also be used as the solvent.

Examples of the oxidizing agent include commercially available reagents such as manganese dioxide, sulfur trioxide-pyridine, activated dimethyl sulfoxide and Des s-Martin reagent.

The amount of the oxidizing agent to be used is preferably 0.5 to 3 mol, more preferably 0.8 to 2 mol, with respect to 1 mol of Compound (XIII)

The reaction temperature of the oxidation reaction varies depending on the type of the oxidizing agent, and is preferably −78° C. to 100° C., more preferably −78° C. to 40° C.

The reaction time of the oxidation reaction varies depending on the reaction conditions such as the type of the oxidizing agent, the reaction temperature and the like, and is preferably 5 minutes to 72 hours, more preferably 1 hour to 24 hours.

(Production Method 17: Production Method of Intermediate Compound (SIIIa))

wherein the symbols have the same meanings as defined above.

Compound (SIIIa) can be obtained by cyclizing Compound (XV) which has been obtained by alkylating Compound (XIV) with Compound (LX) or acylating Compound (XVI), obtained from Compound (XIV), with Compound (LXI). Compound (XIV) and Compound (LX) may be synthesized according to known methods. As Compound (LXI), a commercially available compound may be used, or it may be synthesized according to a known method.

(Step 27)

The alkylation reaction of Compound (XIV) is usually performed by reacting Compound (XIV) with an alkyl halide in a solvent in the presence of a base; and, as the solvent, a solvent that does not inhibit the reaction is appropriately selected. Examples of the solvent that does not inhibit the reaction include ethers such as tetrahydrofuran, 1,4-dioxane and ethylene glycol dimethyl ether; acetone; acetonitrile; and N,N-dimethylformamide. A mixed solvent of these may also be used as the solvent.

Examples of the base include alkali metal hydrogen carbonates such as sodium hydrogen carbonate and potassium hydrogen carbonate; alkali metal carbonates such as potassium carbonate and cesium carbonate; amines such as triethylamine, diisopropylethylamine and pyridine; potassium tert-butoxide; and sodium hydride.

The amount of the base to be used is preferably 0.5 to 6 mol, more preferably 0.8 to 3 mol, with respect to 1 mol of Compound (XIV).

The amount of Compound (LX) to be used is preferably 0.5 to 5 mol, more preferably 0.8 to 2 mol, with respect to 1 mol of Compound (XIV).

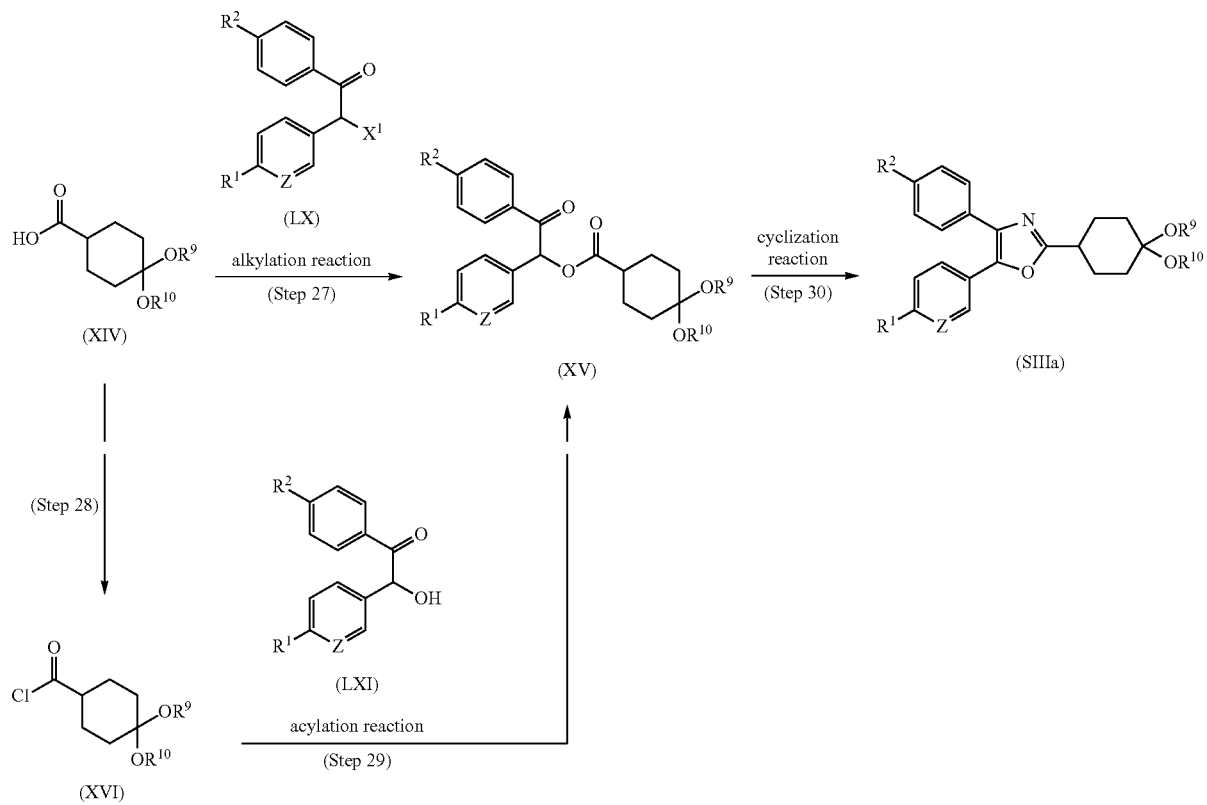

The reaction temperature of the alkylation reaction is preferably −78° C. to 200° C., more preferably −20° C. to 100° C.

The reaction time of the alkylation reaction varies depending on the reaction conditions, and is preferably 5 minutes to 78 hours, more preferably 30 minutes to 48 hours.

(Step 28)

Compound (XVI) can be synthesized from Compound (XIV) in accordance with, for example, a known method in which thionyl chloride, oxalyl chloride or the like is used.

(Step 29)

The acylation reaction of Compound (LXI) with Compound (XVI) is usually performed in a solvent in the presence of a base; and, as the solvent, a solvent that does not inhibit the reaction is appropriately selected. Examples of the solvent that does not inhibit the reaction include halogenated hydrocarbons such as dichloromethane, chloroform, carbon tetrachloride and 1,2-dichloroethane; and ethers such as tetrahydrofuran, 1,2-dimethoxyethane and 1,4-dioxane. A mixed solvent of these may also be used as the solvent.

Examples of the base include pyridine, triethylamine, diisopropylethylamine, N,N-dimethylaminopyridine and the like.

The amount of the base to be used is preferably 0.1 to 6 mol, more preferably 0.8 to 3 mol, with respect to 1 mol of Compound (XVI).

The amount of Compound (LXI) to be used is preferably 0.5 to 3 mol, more preferably 0.8 to 1.5 mol, with respect to 1 mol of Compound (XVI).

The reaction temperature of the acylation reaction is preferably −20° C. to 150° C., more preferably 0° C. to 100° C.

The reaction time of the acylation reaction varies depending on the reaction conditions, and is preferably 5 minutes to 72 hours, more preferably 30 minutes to 48 hours.

(Step 30)

The cyclization reaction of Compound (XV) is usually performed in a solvent in the presence of an ammonium salt, and, as the solvent, a solvent that does not inhibit the reaction is appropriately selected. Examples of the solvent that does not inhibit the reaction include acetic acid and formic acid. A mixed solvent of these may also be used as the solvent.

Examples of the ammonium salt include commercially available reagents such as ammonium acetate, ammonium formate and ammonium carbonate.

The amount of the ammonium salt to be used is preferably 1 to 20 mol, more preferably 2 to 15 mol, with respect to 1 mol of Compound (XV).

The reaction temperature of the cyclization reaction is preferably 0° C. to 200° C., more preferably 50° C. to 120° C.

The reaction time of the cyclization reaction varies depending on the reaction conditions, and is preferably 5 minutes to 100 hours, more preferably 30 minutes to 48 hours.

(Production Method 18: Production Method of Intermediate Compound (SIIIb))

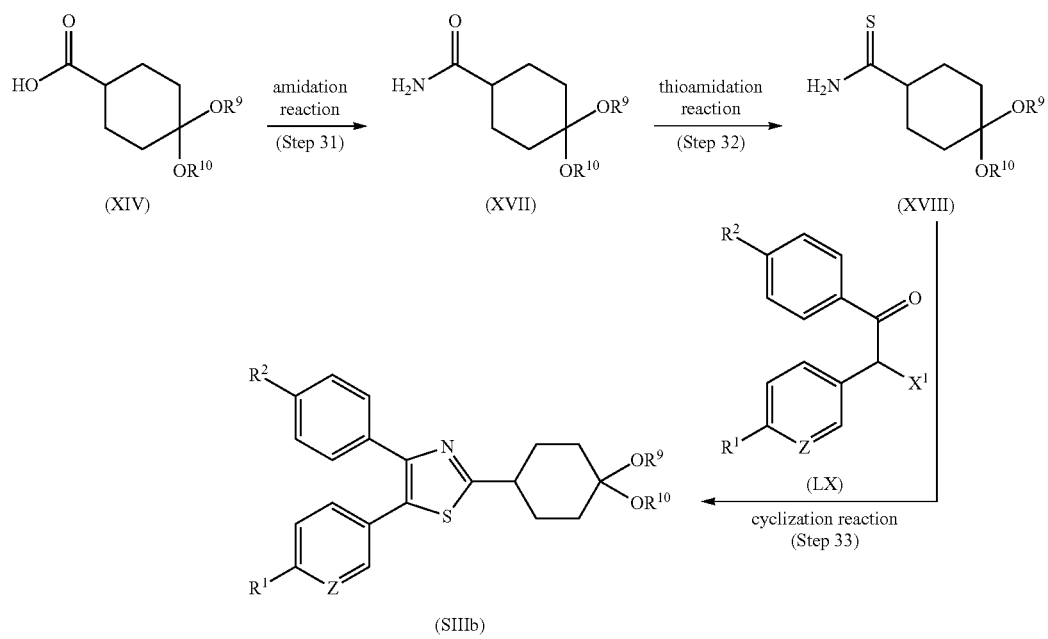

wherein the symbols have the same meanings as defined above.

Compound (SIIIb) can be obtained by amidating Compound (XIV) to obtain Compound (XVII), then thioamidating it to obtain Compound (XVIII), and thereafter cyclizing it with Compound (LX). Compound (XIV) may be synthesized according to a known method. Also, Compound (LX) may be synthesized according to a known method.

(Step 31)

The amidation reaction of Compound (XIV) is usually performed by forming a mixed acid anhydride in a solvent in the presence of a base using a chloroformic ester or the like, and then allowing aqueous ammonia to react therewith. As the solvent, a solvent that does not inhibit the reaction is appropriately selected. Examples of the solvent that does not inhibit the reaction include ethers such as tetrahydrofuran, 1,4-dioxane and ethylene glycol dimethyl ether; halogenated hydrocarbons such as dichloromethane and chloroform; and N,N-dimethylformamide. A mixed solvent of these may also be used as the solvent.

Examples of the chloroformic ester include methyl chloroformate, ethyl chloroformate, isopropyl chloroformate and sec-butyl chloroformate.

The amount of the chloroformic ester to be used is preferably 0.5 to 4 mol, more preferably 0.9 to 2 mol, with respect to 1 mol of Compound (XIV).

Examples of the base include inorganic bases such as sodium hydrogen carbonate, sodium carbonate, potassium carbonate and cesium carbonate; and organic bases such as triethylamine, diisopropylethylamine and pyridine.

The amount of the base to be used is preferably 0.5 to 5 mol, more preferably 0.9 to 2.5 mol, with respect to 1 mol of Compound (XIV).

As for the reaction temperature of the amidation reaction, the formation of a mixed acid anhydride is carried out preferably at −78° C. to 200° C., more preferably at −20° C. to 100° C., and the reaction after adding aqueous ammonia is carried out preferably at −78° C. to 200° C., more preferably at −20° C. to 100° C.

The reaction time of the amidation reaction varies depending on the reaction conditions; and the formation of a mixed acid anhydride is carried out preferably for 5 minutes to 48 hours, more preferably for 30 minutes to 24 hours, and the reaction after adding aqueous ammonia is carried out preferably for 5 minutes to 72 hours, more preferably 30 minutes to 48 hours.

(Step 32)

The thioamidation reaction of Compound (XVII) is usually performed by reacting Compound (XVII) with a commercially available reagent such as Lawesson's reagent, phosphorus pentasulfide or the like in a solvent. As the solvent, a solvent that does not inhibit the reaction is appropriately selected. Examples of the solvent that does not inhibit the reaction include saturated hydrocarbons such as benzene and toluene; halogenated solvents such as dichloromethane and chloroform; and ethers such as tetrahydrofuran and 1,4-dioxane. A mixed solvent of these may also be used as the solvent.

The amount of the Lawesson's reagent, phosphorus pentasulfide or the like to be used is preferably 0.3 to 4 mol, more preferably 0.4 to 2 mol, with respect to 1 mol of Compound (XVII).

The reaction temperature of the thioamidation reaction is preferably −20° C. to 200° C., more preferably 0° C. to 120° C.

The reaction time of the thioamidation reaction varies depending on the reaction conditions, and is preferably 5 minutes to 72 hours, more preferably 30 minutes to 48 hours.

(Step 33)

The cyclization reaction of Compound (XVIII) is usually performed in an appropriately selected solvent that does not inhibit the reaction. Examples of the solvent that does not inhibit the reaction include alcohols such as methanol and ethanol; ethers such as tetrahydrofuran and 1,4-dioxane; and acetonitrile. A mixed solvent of these may also be used as the solvent.

The amount of Compound (LX) to be used is preferably 0.5 to 4 mol, more preferably 0.9 to 1.5 mol, with respect to 1 mol of Compound (XVIII).

The reaction temperature of the cyclization reaction is preferably −20° C. to 200° C., more preferably 0° C. to 100° C.

The reaction time of the cyclization reaction varies depending on the reaction conditions, and is preferably 5 minutes to 72 hours, more preferably 30 minutes to 48 hours.

In cases where Compound (I) was obtained in a free form, it may be converted to a desired salt according to a known method or a method similar thereto. Conversely, in cases where it was obtained as a salt, it may be converted to a free form or another desired salt according to a known method or a method similar thereto.

Compound (I) may be used in a prodrug form. Examples of such a prodrug of Compound (I) include compounds which will be changed into Compound (I) by reaction with an enzyme, gastric acid or the like under physiological conditions in a living body; that is, compounds which will be changed into Compound (I) through enzymatic oxidation, reduction, hydrolysis or the like, and compounds having a structure in which a hydroxyl group(s) of Compound (I) is(are) acylated, alkylated, phosphorylated and/or borated, which compounds will be changed into Compound (I) through hydrolysis or the like by gastric acid or the like. Preferred specific examples of the prodrug of Compound (I) are shown in Table 2, but our therapeutic agents are not limited by these.

TABLE 2

| Compound | Structural Formula |
|---|---|
| 59 | |

TABLE 2-continued

| Compound | Structural Formula |
|---|---|
| 60 | |
| 61 | |
| 62 | |
| 63 | |
| 64 | |

TABLE 2-continued

| Compound | Structural Formula |
|---|---|
| 65 | |
| 66 | |
| 67 | |
| 68 | |
| 69 | |

TABLE 2-continued

| Compound | Structural Formula |
|---|---|
| 70 | 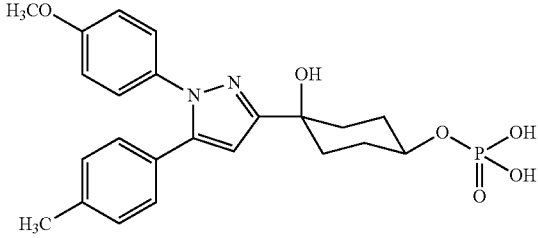 |

The prodrug of Compound (I) can be synthesized from Compound (I) according to a known method. The prodrug of Compound (I) may be those which will be changed into Compound (I) under the physiological conditions described in "Iyakuhin no Kaihatsu (Development of Pharmaceuticals)," *Hirokawa Shoten,* 1990, Vol. 7, p. 163-198; and *Prog. Med.* 5, 1985, p. 2157-2161.

A pharmaceutical comprising Compound (I) shows an excellent therapeutic effect on urine storage disorders also in cases where it is administered to mammal other than human. Examples of the mammal other than human include mouse, rat, hamster, rabbit, cat, dog, bovine, sheep, monkey and so on.

As a mode of administration of Compound (I), Compound (I) may be administered orally or parenterally as it is or after blending it with a pharmaceutically acceptable carrier(s).

In cases where a formulation comprising Compound (I) is orally administered, examples of the dosage form include tablets (including sugar coated tablets and film coated tablets), pills, granules, powders, capsules (including soft capsules and microcapsules), syrups, emulsions and suspensions. In cases where it is parenterally administered, examples of the dosage form include injection solutions, impregnating agents, drops and suppositories. It is also useful to combine the formulation with an appropriate base (for example, a polymer of butyric acid, a polymer of glycolic acid, a copolymer of butyric acid-glycolic acid, a mixture of a polymer of butyric acid and a polymer of glycolic acid, or a polyglycerol fatty acid ester) to form a sustained release formulation.

Preparation of the formulation which comprises Compound (I) and is in the above-mentioned dosage form may be carried out according to a known production method commonly used in the field of formulation of pharmaceuticals. In this case, the formulation may be produced such that an excipient, a binder, a lubricant, a disintegrator, a sweetener, a surfactant, a suspending agent, an emulsifier and/or the like which is(are) commonly used in the field of formulation of pharmaceuticals is(are) contained therein as required.

Preparation of a tablet comprising Compound (I) may be carried out such that an excipient, a binder, a disintegrator, a lubricant and/or the like is(are) contained therein; and preparation of a pill or a granule may be carried out such that an excipient, a binder, a disintegrator and/or the like is(are) contained therein. Preparation of a powder or a capsule may be carried out such that an excipient and/or the like is(are) contained therein; preparation of a syrup may be carried out such that a sweetener and/or the like is(are) contained therein; and preparation of an emulsion or a suspension may be carried out such that a surfactant, a suspending agent, an emulsifier and/or the like is(are) contained therein.

Examples of the excipient include lactose, glucose, starch, sucrose, microcrystalline cellulose, powdered glycyrrhiza, mannitol, sodium hydrogen carbonate, calcium phosphate and calcium sulfate.

Examples of the binder include a starch paste solution, a gum arabic solution, a gelatin solution, a tragacanth solution, a carboxymethylcellulose solution, a sodium alginate solution and glycerin.

Examples of the disintegrator include, for example, starch and calcium carbonate.

Examples of the lubricant include magnesium stearate, stearic acid, calcium stearate and purified talc.

Examples of the sweetener include glucose, fructose, invert sugar, sorbitol, xylitol, glycerin and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, sodium carboxymethylcellulose, methylcellulose and bentonite.

Examples of the emulsifier include gum arabic, tragacanth, gelatin and polysorbate 80.

In addition, in cases where the formulation comprising Compound (I) is formulated into the above-mentioned dosage form, a colorant, a preservative, an aromatic, a corrigent, a stabilizer, a thickener and/or the like which is(are) commonly used in the field of formulation of pharmaceuticals may be added therein.

The daily dose of the formulation varies depending on the conditions and the body weight of the patient, type of the compound, administration route and/or the like. For example, in the case of oral administration, it is preferred that administration be carried out at an amount of 1 mg to 1000 mg per adult (body weight: about 60 kg), once or up to three times dividedly. In the case of parenteral administration, it is preferred that, if the formulation is injection solution, administration be carried out at an amount of 0.01 to 100 mg per 1 kg of body weight by intravenous injection.

The term "urine storage disorder" refers to a condition or a symptom of inability to store a sufficient volume of urine in the bladder. Specific examples thereof include pollakiuria, urinary incontinence, urinary urgency and the like.

"Pollakiuria" refers to a condition in which the number of voiding episodes increases. Examples of the pollakiuria include daytime urinary frequency, nocturia, neurogenic pollakiuria, psychogenic pollakiuria and the like.

"Urinary incontinence" refers to a condition of involuntary leakage of urine. Examples of the urinary incontinence include stress urinary incontinence, urge urinary incontinence, mixed urinary incontinence, enuresis (diurnal enuresis, nocturnal enuresis, bed-wetting), persistent incontinence, overflow incontinence, uninhibited incontinence, reflex incontinence, true incontinence, functional incontinence and the like.

"Urinary urgency" refers to a strong, compelling need to urinate which suddenly occurs. Usually people feel a need to urinate at the time when the bladder is filled with a sufficient volume of urine, whereas, patients with a disorder such as overactive bladder feel an abrupt, strong urge to urinate that is difficult to be suppressed and have the sensation that they cannot hold urine anymore, even when the bladder is not filled with a sufficient volume of urine.

Examples of the disease which causes a urine storage disorder(s) such as pollakiuria, urinary incontinence and/or urinary urgency include neurogenic bladder, overactive bladder, unstable bladder, cystospasm, chronic cystitis, interstitial cystitis, painful bladder syndrome (bladder pain syndrome), chronic prostatitis, benign prostatic hyperplasia, prostate cancer and the like.

"Neurogenic bladder" refers to a condition in which the function of urinary storage or voiding of the lower urinary tract is in an abnormal state because of some damage of the nerve governing the lower urinary tract comprising bladder, urethra and external urethral sphincter. Examples of the disease which damages the nerve governing the lower urinary tract include cerebrovascular disease, brain tumor, brain injury, encephalitis, brain tumor, normal pressure hydrocephalus, dementia, Parkinson's disease, depression, striatonigral degeneration, progressive supranuclear palsy, olivo-ponto-cerebellar atrophy, Shy-Drager syndrome, spinal cord injury, vascular disease of spinal cord, spinal cord tumor, myelitis, cervical cord compression disease, syringomyelia, multiple sclerosis, spina bifida, myelomeningocele, spinal canal stenosis, Tethered cord syndrome, myelopathy, diabetes, pelvic cavity surgery and the like.

Interstitial cystitis is a disease in which the interstitial tissue between urothelium and bladder smooth muscle becomes chronically inflamed due to any cause. Main symptoms include urine storage disorders such as pollakiuria, urinary incontinence and urinary urgency; pain and discomfort on urination and the like. QOL (Quality of Life) of the patients seriously decreases depending on the symptoms such as, in particular, pain in the lower abdomen, increased frequency of urination and the like. Although various drug therapies have been performed, any of them cannot exhibit a sufficient therapeutic effect.

The therapeutic agent or the prophylactic agent for a urine storage disorder(s) is preferably used for urine storage disorders accompanied by pain, since it also has an analgesic effect. Among diseases which cause a urine storage disorder(s), diseases accompanied by pain include inflammatory diseases which cause a urine storage disorder(s), for example, chronic cystitis, interstitial cystitis, painful bladder syndrome (bladder pain syndrome) and the like. The therapeutic agent or prophylactic agent for a urine storage disorder(s) is still more preferably used for interstitial cystitis.

The therapeutic agent or prophylactic agent for a urine storage disorder(s) may be used in combination with other therapeutic agent(s) or prophylactic agent(s) for a urine storage disorder(s) or a therapeutic agent(s) or prophylactic agent(s) for any disease(s) which cause(s) a urine storage disorder(s).

Examples of other therapeutic agent or prophylactic agent for a urine storage disorder(s) include anticholinergic drugs such as Propantheline, Oxybutynin, Propiverine, Tolterodine, Temiverine, Trospium, Darifenacin, Solifenacin and KRP-197; smooth muscle relaxants such as Flavoxate; potassium channel openers such as NS-8, ZD-0947, KW-7158, ABT-598 and WAY-151616; calcium channel antagonists such as Nifedipine and Flunarizine; skeletal muscle relaxants such as Baclofen, Diazepam and Lanperisone; antidepressants such as Imipramine, Desipramine, Fluoxetine, Fluvoxamine, Milnacipran, Paroxetine and Duloxetine; vasopressin agonists such as Desmopressin; tachykinin antagonists such as TAK-637, SR-48968 and Talnetant; β-agonists such as Clenbuterol, KUC-7483, YM-178 and GW-427353; vanilloid agonists such as capsaicin and resiniferatoxin; vanilloid antagonists such as SB-705498, AMG-0347, BCTC, A-784168, SPM-955 and DD-161515; PGE antagonists such as ONO-8711 and ONO-8992; COX inhibitors such as Flurbiprofen; cd agonists such as R-450; cd antagonists such as Doxazosin, Indramin, Terazosin, Urapidil, Alfuzosin, Prazosin, Naftopidil, Tamsulosin, Selodosin, Fiduxosin and KMD-3213; sodium channel blockers such as Vinpocetine, GW-286103, Zonisamide, Mexiletine, Ranolazine and Rilzole and the like.

Examples of the disease which causes a urine storage disorder(s) include benign prostatic hyperplasia, prostate cancer, diabetes, cerebrovascular disease, dementia including Alzheimer's disease, depression, Parkinson's disease, multiple sclerosis and the like.

Examples of the therapeutic agent or prophylactic agent for benign prostatic hyperplasia include 5α reductase inhibitors such as Finasteride, Dutasteride, Izonsteride, CS-891 and MK-434; androgen receptor antagonists such as Flutamide, Bicalutamide and Nilutamide; antiandrogen drugs such as Allylestrenol, Chlormadinone, Gestonorone, Cyproterone, Osaterone and Nomegestrol; endothelin antagonists such as SB-217242 and TA-0201; botanical drugs such as Eviprostat and Cernilton; α1 antagonists described above and the like.

Examples of the therapeutic agent or prophylactic agent for prostate cancer include LH-RH agonists such as Leuprorelin, Goserelin, Buserelin, Nafarelin and Triptorelin; LH-RH antagonists such as Cetrorelix, Ganirelix and Abarelix; 5α-reductase inhibitors described above; androgen receptor antagonists described above; antiandrogen drugs described above and the like.

Examples of the therapeutic agent or prophylactic agent for diabetes include anti-insulin resistance drugs such as Pioglitazone, Troglitazone and Rosiglitazone; insulin secretion enhancers such as Tolbutamide, Chlorpropamide, Tolazamide, Acetohexamide, Glyclopyramide, Glibenclamide, Gliclazide, Glimepiride, Repaglinide and Nateglinide; biguanides such as Metformin and Buformin; α-glucosidase inhibitors such as insulin, Acarbose, Voglibose, Miglitol and Emiglitate; β3 adrenaline receptor agonists such as AJ-9677, SR-58611-A, SB-226552 and AZ40140; Erogoset; Pramlintide; Leptin; BAY-27-9955 and the like.

Examples of the therapeutic agent or prophylactic agent for cerebrovascular disease include Aniracetam, Ibudilast, Tiapride, Cardiocrome, Citicoline, γ-aminobutyric acid, Ifenprodil, Nicergoline, Vinpocetine, Nizofenone, Bencyclane, Cinepazide and the like.

Examples of the therapeutic agent or prophylactic agent for dementia including Alzheimer's disease include Donepezil, Memantine, Galantamine and the like.

Examples of the therapeutic agent or prophylactic agent for depression include antidepressants described above and the like.

Examples of the therapeutic agent or prophylactic agent for Parkinson's disease include Amantadine, Trihexyphenidyl, Bromocriptine, Levodopa, Carbidopa, Apomorphine and the like.

Examples of the therapeutic agent or prophylactic agent for multiple sclerosis include steroid drugs, Interferon-β-1b and the like.

EXAMPLES

Our therapeutic agents will now be described practically by way of examples thereof, but this disclosure is not restricted thereto.

(Effects in Cyclophosphamide-induced Pollakiuria Model Rats)

In the experiments, 6 to 7 female SD rats of 7 to 11 weeks old were used for one experimental group. The pollakiuria model (Lecci A et al., *British Journal of Pharmacology*, 2000, vol. 130, p. 331) was prepared by intraperitoneally administering cyclophosphamide (SIGMA) to rats (150 mg/kg). This model has been considered to be useful as a model of urine storage disorders associated with inflammatory disease, in particular, a model of pollakiuria of interstitial cystitis. Four to five hours after administration of cyclophosphamide, pollakiuria model rats were anesthetized by intraperitoneal administration of urethane (1 g/kg). Thereafter, a small incision was formed in the hypogastrium, and both ureters were ligated, followed by forming small incision in the ureters at the side of the kidney. Next, the bladder apex of each pollakiuria model rat was incised, and a polyethylene tube filled with physiological saline was inserted and indwelled. The other end of the tube was equipped with a three-necked cock. One of the necks thereof was connected to a pressure transducer (NIHON KOHDEN) for measurement of intravesical pressure, and the other neck was connected to an infusion pump to infuse physiological saline.

Thirty minutes after the above-described surgery was completed, physiological saline was continuously infused into the bladder (3.6 mL/hr) to obtain continuous cystometrograms (hereinafter "CMGs"). After confirming that CMGs became stable, a solution of the test compound or its vehicle was administered through the tail vein. The ratio of change in the number of voiding episodes from before to after the administration in the test compound group was obtained and compared to the ratio in the vehicle group.

A solution of the test compound was prepared so that the concentration of the test compound was 10 mg/mL, and intravenously administered in an administration volume of 0.5 mL per 1 kg body weight (5 mg/kg). Dimethyl sulfoxide (hereinafter "DMSO"):Tween 80:physiological saline (1:1:8) was used as a vehicle of the test compound solution.

The number of voiding episodes was counted based on CMGs. Taking the number of voiding episodes counted for a time period of 20 minutes before the administration of the test compound as 100%, the number of voiding episodes counted for a time period of 20 minutes after the administration of the test compound was expressed in %, which was used as the ratio of change in the number of voiding episodes. Statistical processing was carried out by unpaired t test.

The result is shown in FIG. 1. The vertical axis shows the ratio of change in the number of voiding episodes (mean±standard error, N=6 to 7). Asterisk in the figure indicates a significant difference (*: p<0.05) from the vehicle group of pollakiuria model rats ("Vehicle" group in the figure).

Intravenous administration of 5 mg/kg Compound 3 significantly improved the increase in the number of voiding episodes observed in pollakiuria model rats compared to the vehicle group. This result indicates that Compound (I) having a cyclohexane skeleton is effective against urine storage disorders.

(Binding Ability to Human Muscarinic Receptors)

CHO cells expressing human muscarinic M1, 2, 3, 4 and 5 receptors, respectively, were used (Buckley N J et al., *Mol. Pharmacol.*, 1989, vol. 35, no. 4, p. 469-476). Receptor binding experiments were carried out according to a conventional method (Luthin G R et al., *Pharmacol Exp Ther.*, 1984, vol. 228, no. 3, p. 648-655). As a radiolabeled ligand, 0.8 nmol/L [$^3$H]N-Methylscopolamine was used; and as a nonspecific ligand, 1 μmol/L Atoropine was used. The inhibition ratios by Compound 3 to specific binding of radiolabeled ligand to muscarinic receptors are shown in Table 3.

TABLE 3

| Receptors | Inhibition Ratio by 10 μmol/L Compound 3 (%) |
|---|---|
| Muscarinic M1 | −10 |
| Muscarinic M2 | −6 |
| Muscarinic M3 | −4 |
| Muscarinic M4 | −1 |
| Muscarinic M5 | −4 |

It was confirmed that Compound 3 did not bind to any of muscarinic receptor subtypes, indicating that there is no concern that Compound (I) having a cyclohexane skeleton will cause side effects due to the anticholinergic action.

(Effects on Pain)

The mouse acetic acid writhing model, by which pain can be evaluated, was used to evaluate the analgesic effect of Compound (I).

Male ddY mice of 5 to 6 weeks old were fasted for 16 hours while allowing them to freely drink water, and a test compound solution or its vehicle was orally administered (10 mL/kg) to them. DMSO:Tween80:distilled water (1:1:8) or 27% hydroxypropyl-β-cyclodextrin (hereinafter "HP-β-CD") was used as a vehicle of test compound solutions. Forty five minutes after the administration, 0.6% acetic acid solution (10 mL/kg) was intraperitoneally administered thereto to induce writhing response (i.e., the behavior to stretch the body and/or bend the body backward). The number of the writhing response observed for 10 minutes from 10 minutes after the administration of acetic acid solution was counted, which was taken as an indicator of pain.

Taking the mean number of writhing response of the vehicle group as 100%, the dose of a test compound by which the response was inhibited by 50% was expressed as "$ED_{50}$". The results are shown in Table 4.

TABLE 4

| Compound | $ED_{50}$ (mg/kg) | Vehicle |
|---|---|---|
| 1 | 3.78 | A |
| 2 | 1.80 | A |
| 3 | 1.40 | A |
| 4 | 1.95 | A |
| 5 | 7.97 | B |
| 9 | 9.92 | B |
| 10 | 0.54 | B |
| 11 | 1.37 | B |
| 12 | 1.77 | B |
| 13 | 5.36 | B |
| 14 | 1.44 | B |
| 15 | 6.07 | B |
| 16 | 1.19 | B |
| 41 | 3.02 | A |
| 43 | 7.32 | B |
| 46 | 9.65 | B |
| 48 | 5.27 | B |

TABLE 4-continued

| Compound | ED$_{50}$ (mg/kg) | Vehicle |
|---|---|---|
| 49 | 2.69 | B |
| 51 | 4.69 | B |
| 53 | 3.77 | A |
| 54 | 3.73 | B |
| 55 | 0.41 | B |
| 58 | 1.58 | A |
| 60 | 6.18 | B |
| 61 | 4.79 | B |

Vehicle A is DMSO:Tween80:distilled water=1:1:8; Vehicle B is HP-β-CD.

The compounds listed in Table 4 all inhibited the writhing response in the mouse acetic acid writhing model, indicating that Compound (I) has an analgesic effect.

Synthesis processes of Compound (I) and source materials and intermediates thereof were described below. Those used in synthesis of intermediates but whose synthesis process was not described hereinbelow were commercially available compounds.

Solvent names in ( ) shown in the NMR data indicate solvents used for the measurements.

JNM-AL400 nuclear magnetic resonance apparatus produced by JEOL LTD. was used to measure 400 MHz NMR spectrum. Chemical shifts were represented by δ (in ppm) using tetramethylsilane as a standard. Signals were represented by s (singlet), d (doublet), t (triplet), q (quartet), quint (quintet), sept (septet), m (multiplet), br (broad), dd (double doublet), dt (double triplet), ddd (double double0 doublet), dq (double quartet), td (triple doublet), tt (triple triplet), respectively. IR spectrum was measured using FT/IR-41 produced by Jasco, and ESI-MS spectrum was measured using Micromass ZQ2K produced by Waters or 1200LC/MSD produced by AgilentTechnology. Solvents used were all commercially available products. For flash chromatography, YFLC W-prep2XY produced by Yamazen was used.

(Compound 1)

As Compound 1,1-(1-(4-methoxyphenyl)-5-(p-tolyl)-1H-pyrazol-3-yl)cyclohexanol:

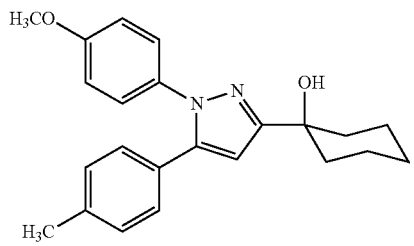 [SMILES: COc1ccc(-n2nc(C3(O)CCCCC3)cc2-c2ccc(C)cc2)cc1]

was synthesized by the following procedure.

Triethylamine (258 μL, 1.88 mmol) was added to a suspension of 4-methoxyphenylhydrazine hydrochloride (165 mg, 0.944 mmol) in ethanol (5.0 mL). The resulting mixture was stirred at room temperature for 30 minutes, and then added to a solution of 3-(1-hydroxycyclohexyl)-1-(p-tolyl)-2-propyn-1-one (Intermediate 8) (214 mg, 0.883 mmol) in ethanol (3.0 mL), followed by stifling the mixture at room temperature for 20 hours. The reaction solution was concentrated under reduced pressure, and distilled water was added to the residue, followed by extraction of the resulting mixture with ethyl acetate. The organic layer was dried over anhydrous magnesium sulfate, and concentrated under reduced pressure. The residue was purified by flash chromatography (silica gel, n-hexane/ethyl acetate) to obtain Compound 1 (141 mg, 0.389 mmol, 44%) as a yellow amorphous product.

-NMR (400 MHz, CDCl$_3$) δ: 1.31-1.42 (1H, m), 1.54-2.03 (9H, m), 2.33 (3H, s), 2.52 (1H, brs), 3.81 (3H, s), 6.40 (1H, s), 6.84 (2H, d, J=8.8 Hz), 7.09 (4H, s), 7.21 (2H, d, J=8.8 Hz).

(Compound 2 and Compound 3)

As Compound 2,1-(1-(4-methoxyphenyl)-5-(p-tolyl)-1H-pyrazol-3-yl)cyclohexan-trans-1,4-diol:

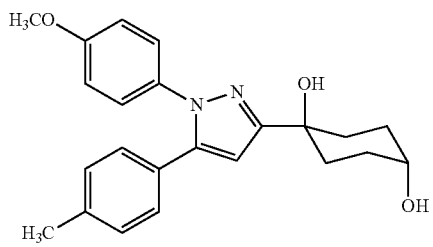

was synthesized by the following procedure. As Compound 3,1-(1-(4-methoxyphenyl)-5-(p-tolyl)-1H-pyrazol-3-yl)cyclohexan-cis-1,4-diol:

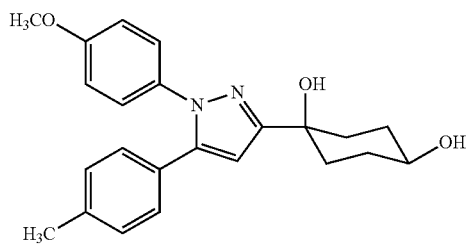

was synthesized by the following procedure.

Sodium borohydride (804 mg, 21.3 mmol) was added to a solution of 4-hydroxy-4-(1-(4-methoxyphenyl)-5-(p-tolyl)-1H-pyrazol-3-yl)-cyclohexan-1-one (Compound 4) (8.00 g, 21.3 mmol) in methanol (200 mL). The resulting mixture was stirred at room temperature for 2 hours, and thereafter poured into 1M hydrochloric acid. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 2 (1.66 g, 4.39 mmol, 21%) and Compound 3 (4.85 g, 12.8 mmol, 60%) as a white solid, respectively.

Compound 2: $^1$H-NMR (400 MHz, CDCl$_3$) δ: 1.36 (1H, d, J=3.6 Hz), 1.64-1.72 (2H, m), 1.77-1.83 (2H, m), 2.04-2.12 (2H, m), 2.32-2.39 (5H, m), 2.56 (1H, s), 3.81 (3H, s), 4.03-4.06 (1H, m), 6.43 (1H, s), 6.85 (2H, d, J=8.8 Hz), 7.10 (4H, s), 7.21 (2H, d, J=8.8 Hz).

IR (KBr, cm$^{-1}$): 3344, 2929, 2875, 1740, 1516, 1443, 1369, 1251, 1032, 1001, 832.

ESI-MS: m/z=379 (M+H)$^+$

Mp 151-153° C.

Anal. Calcd for C23H26N2O3: C, 72.99; H, 6.92; N, 7.40. found: C, 72.97; H, 6.92; N, 7.34.

Compound 3: $^1$H-NMR (400 MHz, CDCl$_3$) δ: 1.44 (1H, s), 1.81-1.99 (6H, m), 2.04-2.12 (2H, m), 2.33 (3H, s), 2.56 (1H, s), 3.70-3.77 (1H, m), 3.80 (3H, s), 6.37 (1H, s), 6.85 (2H, d, J=8.8 Hz), 7.09 (4H, s), 7.20 (2H, d, J=8.8 Hz).

IR (KBr, cm$^{-1}$): 3303, 2918, 1517, 1442, 1366, 1248, 1063, 1026, 837, 807.

ESI-MS: m/z=379 (M+H)+
Mp 164-166° C.
Anal. Calcd for C23H26N2O3: C, 72.99; H, 6.92; N, 7.40. found: C, 72.87; H, 6.86; N, 7.22.

(Compound 5 and Compound 22)

As Compound 5,1-(1-(4-chlorophenyl)-5-(p-tolyl)-1H-pyrazol-3-yl)cyclohexan-trans-1,4-diol:

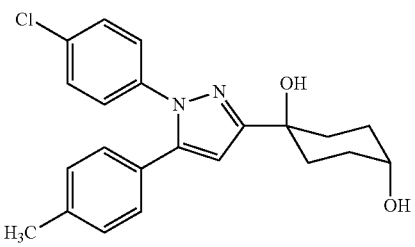

was synthesized by the following procedure. As Compound 22, 1-(1-(4-chlorophenyl)-5-(p-tolyl)-1H-pyrazol-3-yl)cyclohexan-cis-1,4-diol:

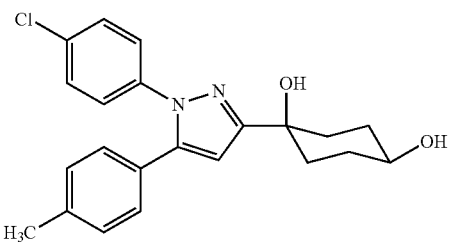

was synthesized by the following procedure.

Sodium borohydride (53 mg, 1.40 mmol) was added to a solution of 4-hydroxy-4-(1-(4-chlorophenyl)-5-(p-tolyl)-1H-pyrazol-3-yl)-cyclohexan-1-one (Intermediate 65) (510 mg, 1.34 mmol) in methanol (13 mL), and the resulting mixture was stirred at room temperature for 2 hours. The reaction solution was concentrated under reduced pressure, and thereafter dissolved in ethyl acetate, and washed with distilled water and brine. The organic layer was dried over anhydrous sodium sulfate, and concentrated under reduced pressure. The residue was purified by flash chromatography (silica gel, n-hexane/ethyl acetate) to obtain Compound 5 (114 mg, 0.298 mmol, 22%) and Compound 22 (360 mg, 0.940 mmol, 70%) as a white solid, respectively.

Compound 5: $^1$H-NMR (400 MHz, CDCl$_3$) δ: 1.36 (1H, br), 1.65-1.72 (2H, m), 1.77-1.82 (2H, m), 2.04-2.11 (2H, m), 2.31-2.38 (2H, m), 2.36 (3H, s), 2.51 (1H, s), 4.03-4.08 (1H, m), 6.44 (1H, s), 7.10 (2H, d, J=8.8 Hz), 7.13 (2H, d, J=8.8 Hz), 7.22-7.30 (4H, m).

IR (KBr, cm$^{-1}$): 3349, 2918, 1497, 1440, 1366, 1240, 1098, 1007, 969, 833, 810.

ESI-MS: m/z=383 (M+H)+

Compound 22: $^1$H-NMR (400 MHz, CDCl$_3$) δ: 1.45 (1H, br), 1.80-1.99 (6H, m), 2.03-2.07 (2H, m), 2.35 (3H, s), 2.51 (1H, s), 3.70-3.80 (1H, m), 6.39 (1H, s), 7.09 (2H, d, J=8.4 Hz), 7.13 (2H, d, J=8.4 Hz), 7.21-7.24 (2H, m), 7.27-7.31 (2H, m).

IR (KBr, cm$^{-1}$): 3365, 2946, 1496, 1442, 1368, 1241, 1095, 1059, 1014, 970, 887.

ESI-MS: m/z=365 (M−OH)+

(Compound 6 and Compound 8)

As Compound 6,1-(1,5-bis(4-methoxyphenyl)-1H-pyrazol-3-yl)cyclohexan-trans-1,4-diol:

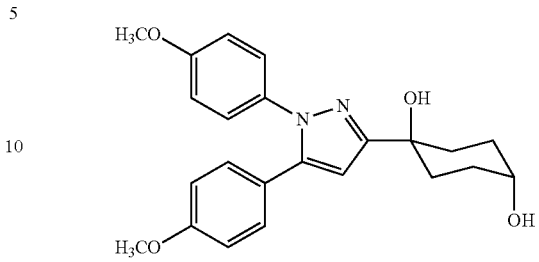

was synthesized by the following procedure. As Compound 8, 1-(1,5-bis(4-methoxyphenyl)-1H-pyrazol-3-yl)cyclohexan-cis-1,4-diol:

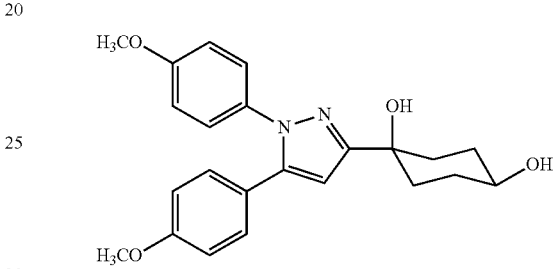

was synthesized by the following procedure.

Sodium borohydride (65 mg, 1.7 mmol) was added to a solution of 4-(1,5-bis(4-methoxyphenyl)-1H-pyrazol-3-yl)-4-hydroxy-cyclohexan-1-one (Intermediate 63) (523 mg, 1.38 mmol) in methanol, and the resulting mixture was stirred at room temperature for 1.5 hours and concentrated under reduced pressure. Distilled water was added to the residue, and the resulting solution was extracted with ethyl acetate. The organic layer was dried over anhydrous magnesium sulfate, and concentrated under reduced pressure. The residue was purified by flash chromatography to separate into low polar components and high polar components. The low polar components were purified by recrystallization (ethyl acetate/n-hexane=2/1) to obtain Compound 6 (79 mg, 0.20 mmol, 14%) as a white crystal. The high polar components were purified by recrystallization (ethyl acetate/n-hexane=2/1) to obtain Compound 8 (186 mg, 0.471 mmol, 34%) as a white crystal.

Compound 6: $^1$H-NMR (400 MHz, CDCl$_3$) δ: 1.33 (1H, d, J=3.4 Hz), 1.63-1.73 (2H, m), 1.75-1.84 (2H, m), 2.03-2.13 (2H, m), 2.30-2.39 (2H, m), 2.55 (1H, s), 3.80 (3H, s), 3.81 (3H, s), 4.02-4.08 (1H, m), 6.40 (1H, s), 6.82 (2H, d, J=8.8 Hz), 6.85 (2H, d, J=8.8 Hz), 7.14 (2H, d, J=8.8 Hz), 7.21 (2H, d, J=8.8 Hz).

IR (KBr, cm$^{-1}$): 3379, 1613, 1517, 1503, 1251, 1180, 1032, 1001, 835.

ESI-MS: m/z=395 (M+H)+

Compound 8: $^1$H-NMR (400 MHz, CDCl$_3$) δ: 1.41 (1H, d, J=4.1 Hz), 1.79-2.55 (8H, m), 2.55 (1H, s), 3.69-3.78 (1H, m), 3.80 (3H, s), 3.81 (3H, s), 6.34 (1H, s), 6.81 (2H, d, J=8.8 Hz), 6.85 (2H, d, J=8.8 Hz), 7.13 (2H, d, J=8.8 Hz), 7.20 (2H, d, J=8.8 Hz).

IR (KBr, cm$^{-1}$): 3385, 1613, 1517, 1503, 1250, 1064, 1031, 970, 835.

ESI-MS: m/z=395 (M+H)+

(Compound 7 and Compound 21)

As Compound 7,1-(5-(4-chlorophenyl)-1-(4-methoxyphenyl)-1H-pyrazol-3-yl)cyclohexan-trans-1,4-diol:

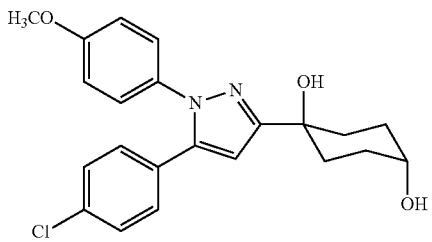 [SMILES: COc1ccc(-n2nc(C3(O)CCC(O)CC3)cc2-c2ccc(Cl)cc2)cc1]

was synthesized by the following procedure. As Compound 21, 1-(5-(4-chlorophenyl)-1-(4-methoxyphenyl)-1H-pyrazol-3-yl)cyclohexan-cis-1,4-diol:

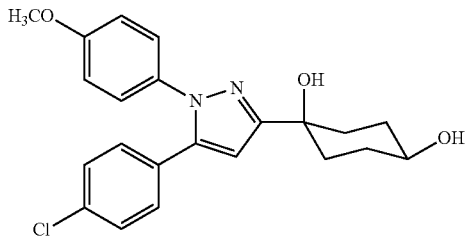 [SMILES: COc1ccc(-n2nc(C3(O)CCC(O)CC3)cc2-c2ccc(Cl)cc2)cc1]

was synthesized by the following procedure.

Sodium borohydride (59.0 mg, 1.56 mmol) was added to a solution of 44544-chlorophenyl)-1-(4-methoxyphenyl)-1H-pyrazol-3-yl)-4-hydroxy-cyclohexan-1-one (Intermediate 64) (619 mg, 1.56 mmol) in methanol (15.6 mL). The resulting mixture was stirred at room temperature for 1 hour, and thereafter poured into 1 M hydrochloric acid. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 7 (131 mg, 0.328 mmol, 21%) and Compound 21 (291 mg, 0.730 mmol, 47%) as a white solid, respectively.

Compound 7: $^1$H-NMR (400 MHz, CDCl$_3$) δ: 1.32 (1H, d, J=3.2 Hz), 1.63-1.73 (2H, m), 1.76-1.84 (2H, m), 2.03-2.12 (2H, m), 2.30-2.39 (2H, m), 2.50 (1H, s), 3.82 (3H, s), 4.02-4.09 (1H, m), 6.46 (1H, s), 6.84-6.87 (2H, m), 7.14 (2H, d, J=8.8 Hz), 7.19 (2H, d, J=8.8 Hz), 7.26-7.28 (2H, m).

ESI-MS: m/z=399 (M+H)$^+$

Compound 21: $^1$H-NMR (400 MHz, CDCl$_3$) δ: 1.41 (1H, d, J=5.2 Hz), 1.82-2.09 (8H, m), 2.49 (1H, s), 3.70-3.78 (1H, s), 3.82 (3H, s), 6.41 (1H, s), 6.85-6.87 (2H, m), 7.13 (2H, d, J=8.4 Hz), 7.18 (2H, d, J=8.4 Hz), 7.25-7.27 (2H, m).

ESI-MS: m/z=399 (M+H)$^+$ (Compound 9)

As Compound 9, 1-(4-chloro-1-(4-methoxyphenyl)-5-(p-tolyl)-1H-pyrazol-3-yl)cyclohexan-cis-1,4-diol:

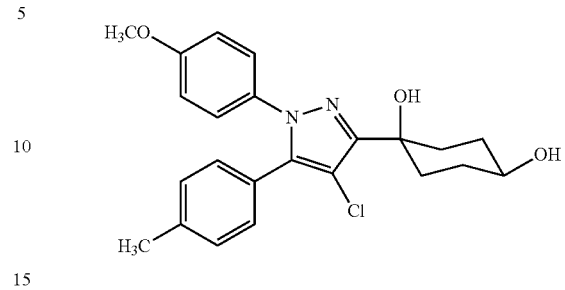

was synthesized by the following procedure.

Potassium carbonate (102 mg, 0.736 mmol) was added to a solution of 4-(4-chloro-1-(4-methoxyphenyl)-5-(p-tolyl)-1H-pyrazol-3-yl)-c-4-hydroxy-cyclohexan-r-1-yl acetate (Intermediate 81) (67 mg, 0.147 mmol) in methanol (1.5 mL), and the resulting mixture was stirred at room temperature for 2 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 9 (58 mg, 0.140 mmol, 95%) as a white solid.

$^1$H-NMR (400 MHz, CDCl$_3$) δ: 1.45 (1H, s), 1.83-2.05 (6H, m), 2.21-2.23 (2H, m), 2.36 (3H, s), 3.04 (1H, s), 3.76-3.79 (4H, m), 6.79-6.83 (2H, m), 7.11-7.16 (6H, m).

ESI-MS: m/z=395, 397 (M–OH)$^+$ (Compound 10)

As Compound 10, 1-(1-(4-methoxyphenyl)-5-(p-tolyl)-1H-pyrazol-3-yl)-4-(trifluoromethyl)cyclohexan-cis-1,4-diol:

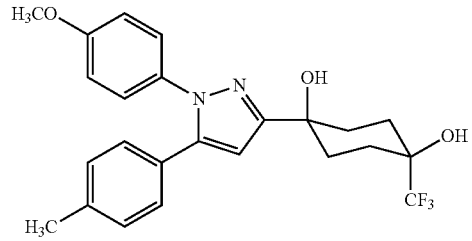

was synthesized by the following procedure.

To a solution of 4-hydroxy-4-(1-(4-methoxyphenyl)-5-(p-tolyl)-1H-pyrazol-3-yl)cyclohexan-1-one (Compound 4) (620 mg, 1.65 mmol) in tetrahydrofuran (6.60 mL), (trifluoromethyl)trimethylsilane (535 μL, 3.62 mmol) was added at 0° C. Thereafter, tetra-n-butylammonium fluoride (TBAF, 1 M solution in tetrahydrofuran) (362 μL, 0.36 mmol) was added dropwise thereto, and the obtained solution was stirred at room temperature for 6 hours. To the reaction solution, tetra-n-butylammonium fluoride (TBAF, 1 M solution in tetrahydrofuran) (3.29 mL, 3.29 mmol) was added. The resulting mixture was stirred at room temperature for 1 hour, and thereafter poured into 1 M hydrochloric acid. The reaction solution was extracted with diethyl ether. The organic layer was washed with brine, dried over anhydrous sodium sulfate, and concentrated under reduced pressure. The residue was purified by flash chromatography (silica gel, n-hexane/ethyl acetate) to obtain Compound 10 (410 mg, 0.92 mmol, 56%) as a white solid.

¹H-NMR (400 MHz, CDCl₃) δ: 1.60 (1H, s), 1.87-2.02 (4H, m), 2.09-2.02 (2H, m), 2.34-2.40 (6H, m), 3.82 (3H, s), 6.47 (1H, s), 6.86 (2H, d, J=8.8 Hz), 7.08-7.11 (4H, m), 7.20 (2H, d, J=8.8 Hz).

IR (KBr, cm⁻¹): 3402, 2954, 1517, 1463, 1305, 1250, 1249, 1179, 1121, 1056, 1024, 834.

ESI-MS: m/z=447 (M+H)⁺

(Compound 11)

As Compound 11, t-4-fluoro-4-(1-(4-methoxyphenyl)-5-(p-tolyl)-1H-pyrazol-3-yl)-cyclohexan-r-1-ol:

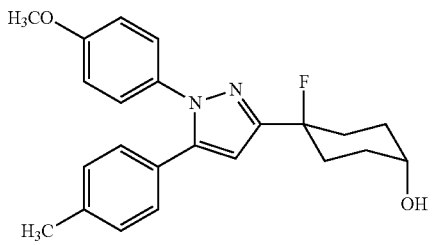 [SMILES: COc1ccc(-n2nc(C3(F)CCC(O)CC3)cc2-c2ccc(C)cc2)cc1]

was synthesized by the following procedure.

Deoxofluor™ (48 μL, 0.262 mmol) was added to a solution of c-4-hydroxy-4-(1-(4-methoxyphenyl)-5-(p-tolyl)-1H-pyrazol-3-yl)-cyclohexan-r-1-yl acetate (Compound 12) (100 mg, 0.238 mmol) in dichloromethane (1.19 mL), and the resulting mixture was stirred at room temperature for 15 minutes. To the reaction solution, 1 M hydrochloric acid was added, and the resulting solution was extracted with chloroform. The organic layer was washed with brine, and then dried over anhydrous magnesium sulfate, and concentrated under reduced pressure to obtain a residue.

Potassium carbonate (164 mg, 1.18 mmol) was added to a solution of the obtained residue in methanol (2.4 mL), and the resulting mixture was stirred at room temperature for 2 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 11 (22.4 mg, 0.058 mmol, 25%) as a white solid.

¹H-NMR (400 MHz, CDCl₃) δ: 1.37 (1H, m), 1.72-1.77 (2H, m), 2.02-2.14 (4H, m), 2.34 (3H, s), 2.38-2.49 (2H, m), 3.81 (3H, s), 4.11 (1H, m), 6.52 (1H, m), 6.84 (2H, d, J=8.8 Hz), 7.22 (2H, d, J=8.8 Hz), 7.26 (4H, s).

ESI-MS: m/z=381 (M+H)⁺

(Compound 12)

As Compound 12, c-4-hydroxy-4-(1-(4-methoxyphenyl)-5-(p-tolyl)-1H-pyrazol-3-yl)-cyclohexan-r-1-yl acetate:

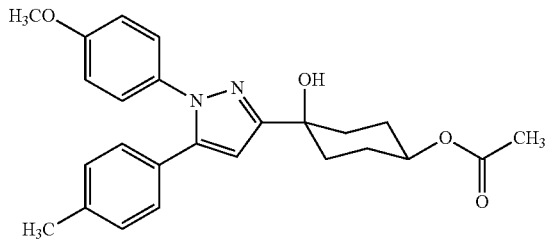 [SMILES: COc1ccc(-n2nc(C3(O)CCC(OC(C)=O)CC3)cc2-c2ccc(C)cc2)cc1]

was synthesized by the following procedure.

Acetic anhydride (0.312 mL, 3.30 mmol), pyridine (0.267 mL, 3.30 mmol), and 4-dimethylaminopyridine (16.1 mg, 0.132 mmol) were added to a suspension of 1-(1-(4-methoxyphenyl)-5-(p-tolyl)-1H-pyrazol-3-yl)cyclohexan-cis-1,4-diol (Compound 3) (500 mg, 1.32 mmol) in dichloromethane (4.4 mL), and the resulting mixture was stirred at room temperature for 45 minutes. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 12 (556 mg, 1.32 mmol, quant.) as an amorphous product.

¹H-NMR (400 MHz, CDCl₃) δ: 1.89-2.08 (11H, m), 2.34 (3H, s), 2.64 (1H, brs), 3.81 (3H, s), 4.80-4.88 (1H, m), 6.36 (1H, s), 6.85 (2H, d, J=8.8 Hz), 7.00 (4H, s), 7.20 (2H, d, J=8.8 Hz).

ESI-MS: m/z=421 (M+H)⁺

(Compound 13)

As Compound 13, 4-methoxy-1-(1-(4-methoxyphenyl)-5-(p-tolyl)-1H-pyrazol-3-yl)cyclohexanol:

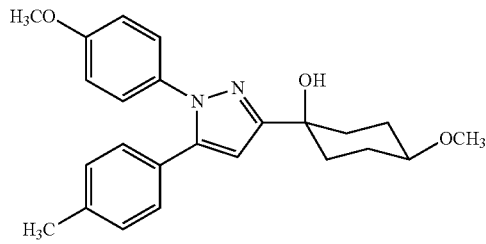

was synthesized by the following procedure.

Potassium carbonate (197 mg, 1.42 mmol) was added to a solution of c-4-methoxy-1-(1-(4-methoxyphenyl)-5-(p-tolyl)-1H-pyrazol-3-yl)-cyclohexan-r-1-yl acetate (Intermediate 39) (124 mg, 0.284 mmol) in methanol (2.8 mL), and the resulting mixture was stirred at room temperature for 18 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 13 (102 mg, 0.260 mmol, 91%) as a white amorphous product.

¹H-NMR (400 MHz, CDCl₃) δ: 1.78-1.88 (2H, m), 1.90-1.99 (4H, m), 2.03-2.09 (2H, m), 2.33 (3H, s), 2.49 (1H, s), 3.24-3.32 (1H, m), 3.39 (3H, s), 3.81 (3H, s), 6.39 (1H, s), 6.85 (2H, d, J=8.8 Hz), 7.09 (4H, s), 7.20 (2H, d, J=8.8 Hz).

IR (KBr, cm⁻¹): 3425, 2937, 1516, 1443, 1369, 1300, 1249, 1171, 1099, 1030, 968, 834, 801.

ESI-MS: m/z=393 (M+H)⁺

(Compound 14 and Compound 20)

As Compound 14, 4-(hydroxymethyl)-4-(1-(4-methoxyphenyl)-5-(p-tolyl)-1H-pyrazol-3-yl)-trans-1,4-cyclohexanol (Compound 14):

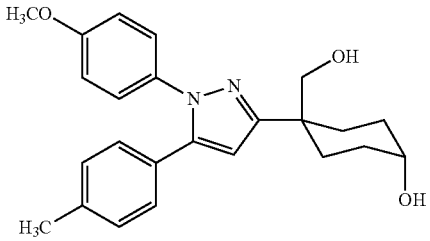 [SMILES: COc1ccc(-n2nc(C3(CO)CCC(O)CC3)cc2-c2ccc(C)cc2)cc1]

was synthesized by the following procedure. As Compound 20, 4-(hydroxymethyl)-4-(1-(4-methoxyphenyl)-5-(p-tolyl)-1H-pyrazol-3-yl)-cis-1,4-cyclohexanol (Compound 20):

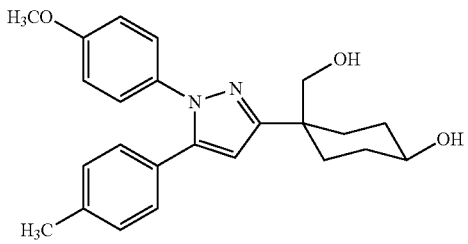 [SMILES: COc1ccc(-n2nc(C3(CO)CCC(O)CC3)cc2-c2ccc(C)cc2)cc1]

was synthesized by the following procedure.

Sodium borohydride (30.4 mg, 0.804 mmol) was added to a solution of 4-(benzyloxymethyl)-4-(1-(4-methoxyphenyl)-5-(p-tolyl)-1H-pyrazol-3-yl)cyclohexan-1-one (Intermediate 51) (387 mg, 0.804 mmol) in methanol (8.0 mL). The resulting mixture was stirred at room temperature for 1 hour, and thereafter poured into 1 M hydrochloric acid. The reaction solution was extracted with ethyl acetate. The organic layer was washed with brine, dried over anhydrous sodium sulfate, and concentrated under reduced pressure to obtain a residue.

To a solution of the obtained residue in methanol (8.0 mL), 10% palladium carbon (86.0 mg, 0.080 mmol) was added under hydrogen atmosphere, and the resulting mixture was stirred at room temperature for 3 hours. The reaction solution was filtered through Celite, and the filtrate was concentrated under reduced pressure. The residue was purified by flash chromatography (amine silica gel, n-hexane/ethyl acetate) to obtain Compound 14 (51.6 mg, 0.131 mmol, 16%) as a white solid and Compound 20 (164 mg, 0.418 mmol, 52%) as a white amorphous product.

Compound 14: $^1$H-NMR (400 MHz, CDCl$_3$) δ: 1.43 (1H, brs), 1.54-1.67 (2H, m), 1.83-1.91 (4H, m), 2.00-2.08 (2H, m), 2.34 (3H, s), 3.24-3.33 (1H, m), 3.78-3.86 (6H, m), 6.32 (1H, s), 6.84 (2H, d, J=8.8 Hz), 7.10 (4H, s), 7.19 (2H, d, J=8.8 Hz).

ESI-MS: m/z=393 (M+H)$^+$

Compound 20: $^1$H-NMR (400 MHz, CDCl$_3$) δ: 1.39 (1H, d, J=4.8 Hz), 1.46-1.60 (4H, m), 1.85-1.95 (2H, m), 2.33-2.40 (5H, m), 2.71 (1H, t, J=6.4 Hz), 3.55 (2H, d, J=6.4 Hz), 3.71-3.83 (4H, m), 6.37 (1H, s), 6.85 (2H, d, J=8.8 Hz), 7.10 (4H, s), 7.20 (2H, d, J=8.8 Hz).

ESI-MS: m/z=393 (M+H)$^+$ (Compound 15)

As Compound 15, 1-(1-(4-methoxyphenyl)-5-(6-methylpyridin-3-yl)-1H-pyrazol-3-yl)cyclohexan-cis-1,4-diol:

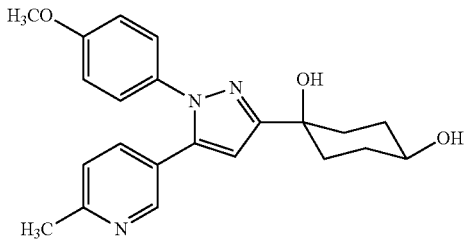

was synthesized by the following procedure.

Sodium borohydride (12.1 mg, 0.32 mmol) was added to a solution of 4-hydroxy-4-(1-(4-methoxyphenyl)-5-(6-methylpyridin-3-yl)-1H-pyrazol-3-yl)-cyclohexan-1-one (Intermediate 62) (109.5 mg, 0.29 mmol) in methanol (1.5 mL). The resulting mixture was stirred at room temperature for 40 minutes, and thereafter 1 M hydrochloric acid was added thereto. The reaction solution was washed with ethyl acetate, and the aqueous layer was basified with 1 M aqueous sodium hydroxide solution, followed by extraction of the resulting mixture twice with ethyl acetate. The organic layer was washed with brine, dried over anhydrous sodium sulfate, and concentrated under reduced pressure. The residue was purified by flash chromatography (silica gel, ethyl acetate) to obtain Compound 15 (30.6 mg, 0.81 mmol, 28%) as a white solid.

$^1$H-NMR (400 MHz, CDCl$_3$) δ: 1.59 (1H, brs), 1.81-2.00 (6H, m), 2.05-2.08 (2H, m), 2.55 (3H, s), 2.61 (1H, s), 3.71-3.78 (1H, m), 3.81 (3H, s), 6.46 (1H, s), 6.86 (2H, d, J=8.8 Hz), 7.06 (1H, d, J=8.0 Hz), 7.18 (2H, d, J=8.8 Hz), 7.32 (1H, dd, J=2.0, 8.0 Hz), 8.40 (1H, d, J=2.0 Hz).

IR (KBr, cm$^{-1}$): 3444, 2933, 2858, 1516, 1249, 1067, 968, 839.

ESI-MS: m/z=380 (M+H)$^+$ (Compound 16)

As Compound 16, 4-hydroxy-4-(1-(4-methoxyphenyl)-5-(p-tolyl)-1H-pyrazol-3-yl)-cis-cyclohexanecarboxylic acid:

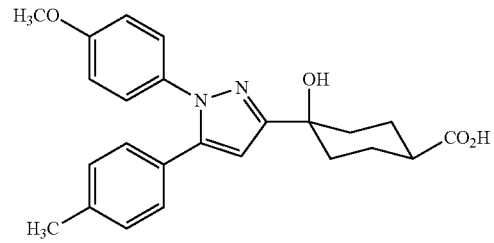 [SMILES: COc1ccc(-n2nc(C3(O)CCC(C(=O)O)CC3)cc2-c2ccc(C)cc2)cc1]

was synthesized by the following procedure.

Distilled water (0.8 ml) and 2-methyl-2-butene (101 μl, 0.96 mmol) were added to a solution of c-4-hydroxy-4-(1-(4-methoxyphenyl)-5-(p-tolyl)-1H-pyrazol-3-yl)-cis-cyclohexan-r-1-carbaldehyde (Intermediate 42) (124.9 mg, 0.32 mmol) in t-butanol (2.4 ml), and the obtained solution was cooled in ice. At 0° C., sodium dihydrogen phosphate (42.1 mg, 0.35 mmol) and sodium chlorite (72.3 mg, 0.80 mmol) were added thereto, and the obtained mixture was stirred for 5 minutes. The mixture was allowed to warm to room temperature, stirred for 1 hour, and then cooled in ice to 0° C. Thereafter, an aqueous sodium thiosulfate solution was added thereto, and the resulting mixture was stirred. To the mixture, 1 M hydrochloric acid and ethyl acetate were added, and the resulting solution was subjected to extraction. The organic layer was washed with brine, dried over anhydrous sodium sulfate, and concentrated under reduced pressure. The residue was purified by flash chromatography (silica gel, n-hexane/ethyl acetate) to obtain Compound 16 (116.6 mg, 0.29 mmol, 93%) as a white solid.

$^1$H-NMR (400 MHz, CDCl$_3$) δ: 1.87-2.11 (9H, m), 2.33 (3H, s), 2.40-2.43 (1H, m), 3.81 (3H, s), 6.38 (1H, s), 6.84 (2H, d, J=9.2 Hz), 7.09-7.09 (4H, m), 7.20 (2H, d, J=9.2 Hz).

IR (KBr, cm$^{-1}$): 3523, 2928, 1706, 1517, 1252, 831.

ESI-MS: m/z=407 (M+H)$^+$ (Compound 17)

As Compound 17, 4,4-difluoro-1-(1-(4-methoxyphenyl)-5-(p-tolyl)-1H-pyrazol-3-yl)cyclohexanol:

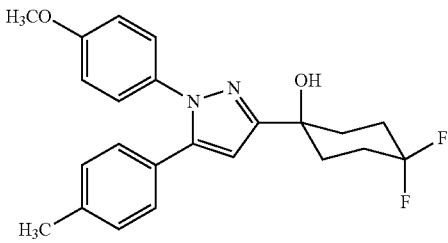 [SMILES: COc1ccc(-n2nc(C3(O)CCC(F)(F)CC3)cc2-c2ccc(C)cc2)cc1]

was synthesized by the following procedure.

To a solution of 1-(1-(4-methoxyphenyl)-5-(p-tolyl)-1H-pyrazol-3-yl)-4-oxo-cyclohexan-1-yl acetate (Intermediate 41) (110 mg, 0.263 mmol) in dichloromethane (2.63 mL), (dimethylamino)sulfur trifluoride (DAST) (104 μL, 0.578 mmol) was added, and the resulting mixture was stirred at room temperature for 2 hours. To the reaction solution, 1 M hydrochloric acid was added, and the resulting solution was extracted with chloroform. The organic layer was washed with brine, and then dried over anhydrous magnesium sulfate, and concentrated under reduced pressure to obtain a residue.

To a solution of the obtained residue in tetrahydrofuran (193 μL) and methanol (386 μL), a 4 M aqueous sodium hydroxide solution (193 μL, 0.772 mmol) was added, and the resulting mixture was stirred at room temperature for 6 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Compound 17 (41.0 mg, 0.103 mmol, 39%) as a white solid.

$^1$H-NMR (400 MHz, CDCl$_3$) δ: 2.01-2.31 (8H, m), 2.34 (3H, s), 2.77 (1H, s), 3.81 (3H, s), 6.37 (1H, s), 6.86 (2H, d, J=8.8 Hz), 7.10 (4H, s), 7.21 (2H, d, J=8.8 Hz).

ESI-MS: m/z=399 (M+H)$^+$

The following compounds were synthesized in the same manner as in the synthesis of the above-described Compound 2 and Compound 3.

TABLE 5

| Compound | Structural Formula | Compound Data |
|---|---|---|
| 18 | | $^1$H-NMR (400 MHz, CDCl3) δ: 1.44 (1H, d, J = 4.0 Hz), 1.84-2.01 (8H, m), 2.48 (1H, s), 3.75 (1H, s), 3.82 (3H, s), 6.49 (1H, s), 6.87 (2H, d, J = 9.2 Hz), 7.19 (2H, d, J = 9.2 Hz), 7.32 (2H, d, J = 8.2 Hz), 7.55 (2H, d, J = 8.2 Hz). ESI-MS: m/z = 433 (M + H)$^+$ |
| 19 | | $^1$H-NMR (400 MHz, CDCl3) δ: 1.35 (1H, s), 1.67-1.71 (2H, m), 1.78-1.84 (2H, m), 2.0-2.11 (2H, m), 2.33-2.40 (2H, m), 2.49 (1H, s), 3.83 (3H, s), 4.07 (1H, m), 6.53 (1H, s), 6.87 (2H, d, J = 8.2 Hz), 7.19 (2H, d, J = 8.2 Hz), 7.33 (2H, d, J = 8.2 Hz), 7.55 (2H, d, J = 8.2 Hz). ESI-MS: m/z = 433 (M + H)$^+$ |
| 23 | | $^1$H-NMR (400 MHz, CDCl$_3$) δ: 1.34 (1H, d, J = 3.2 Hz), 1.64-1.72 (2H, m), 1.76-1.83 (2H, m), 2.03-2.12 (2H, m), 2.30-2.39 (2H, m), 2.45 (1H, s), 4.03-4.09 (1H, m), 6.48 (1H, s), 7.15 (2H, d, J = 8.8 Hz), 7.22 (2H, d, J = 8.8 Hz), 7.30-7.33 (4H, m). ESI-MS: m/z = 403 (M + H)$^+$ |
| 24 | | $^1$H-NMR (400 MHz, CDCl$_3$) δ: 1.45 (1H, d, J = 4.0 Hz), 1.80-2.07 (8H, m), 2.46 (1H, s), 3.70-3.79 (1H, s), 6.43 (1H, s), 7.14 (2H, d, J = 8.8 Hz), 7.21 (2H, d, J = 8.8 Hz), 7.29-7.33 (4H, m). ESI-MS: m/z = 403 (M + H)$^+$ |

TABLE 5-continued

| Compound | Structural Formula | Compound Data |
| --- | --- | --- |
| 25 | | $^1$H-NMR (400 MHz, CDCl$_3$) δ: 1.33 (1H, d, J = 3.2 Hz), 1.65-1.73 (2H, m), 1.78-1.84 (2H, m), 2.04-2.13 (2H, m), 2.32-2.40 (2H, m), 2.51 (1H, s), 4.03-4.09 (1H, m), 6.48 (1H, s), 7.14-7.16 (2H, m), 7.26-7.28 (7H, m). ESI-MS: m/z = 369 (M + H)$^+$ |
| 26 | | $^1$H-NMR (400 MHz, CDCl$_3$) δ: 1.43 (1H, d, J = 5.2 Hz), 1.81-2.09 (8H, m), 2.50 (1H, s), 3.71-3.79 (1H, m), 6.43 (1H, s), 7.12-7.16 (2H, m), 7.25-7.38 (7H, m). ESI-MS: m/z = 369 (M + H)$^+$ |
| 27 | | $^1$H-NMR (400 MHz, CDCl$_3$) δ: 1.41 (1H, brs), 1.64-1.72 (2H, m), 1.77-1.83 (2H, m), 2.04-2.11 (2H, m), 2.31-2.38 (2H, m), 2.34 (3H, s), 2.35 (3H, s), 2.59 (1H, s), 4.02-4.07 (1H, m), 6.43 (1H, s), 7.09-7.11 (4H, m), 7.12 (2H, d, J = 8.4 Hz), 7.18 (2H, d, J = 8.4 Hz).<br>IR (KBr, cm$^{-1}$): 3343, 2918, 1518, 1440, 1367, 1266, 1240, 1196, 1159, 1107, 1007, 824, 810.<br>ESI-MS: m/z = 363 (M + H)$^+$ |
| 28 | | $^1$H-NMR (400 MHz, CDCl$_3$) δ: 1.48 (1H, brs), 1.80-1.99 (6H, m), 2.02-2.09 (2H, m), 2.34 (3H, s), 2.35 (3H, s), 2.61 (1H, s), 3.70-3.78 (1H, m), 6.38 (1H, s), 7.08-7.12 (4H, m), 7.12 (2H, d, J = 8.8 Hz), 7.17 (2H, d, J = 8.8 Hz).<br>IR (KBr, cm$^{-1}$): 3375, 2937, 2870, 1519, 1502, 1440, 1362, 1217, 1193, 1112, 1064, 1042, 1017, 973, 886, 821, 804.<br>ESI-MS: m/z = 345 (M − OH)$^+$ |
| 29 | | $^1$H-NMR (400 MHz, CDCl$_3$) δ: 1.47 (1H, brs), 1.64-1.73 (2H, m), 1.76-1.85 (2H, m), 2.03-2.12 (2H, m), 2.31-2.40 (2H, m), 2.34 (3H, s), 2.62 (1H, s), 4.02-4.08 (1H, m), 6.45 (1H, s), 7.08-7.14 (4H, m), 7.26-7.36 (5H, m).<br>IR (KBr, cm$^{-1}$): 3337, 2920, 1599, 1506, 1437, 1366, 1005, 810, 765, 696.<br>ESI-MS: m/z = 349 (M + H)$^+$ |
| 30 | | $^1$H-NMR (400 MHz, CDCl$_3$) δ: 1.50 (1H, brs), 1.80-2.00 (6H, m), 2.03-2.09 (2H, m), 2.34 (3H, s), 2.60 (1H, s), 3.70-3.79 (1H, m), 6.40 (1H, s), 7.08-7.12 (4H, m), 7.27-7.35 (5H, m).<br>IR (KBr, cm$^{-1}$): 3374, 2919, 1596, 1505, 1440, 1361, 1217, 1112, 1064, 1044, 1019, 973, 886, 819, 799, 771, 693.<br>ESI-MS: m/z = 331 (M − OH)$^+$ |

TABLE 5-continued

| Compound | Structural Formula | Compound Data |
|---|---|---|
| 31 | | ¹H-NMR (400 MHz, CDCl₃) δ: 1.42 (1H, d, J = 4.8 Hz), 1.79-2.01 (6H, m), 2.03-2.08 (2H, m), 2.54 (1H, s), 3.71-3.80 (1H, m), 3.81 (3H, s), 6.41 (1H, s), 6.84 (2H, d, J = 6.8 Hz), 7.18-7.23 (4H, m), 7.28-7.30 (3H, m).<br>ESI-MS: m/z = 365 (M + H)⁺ |
| 32 | | ¹H-NMR (400 MHz, CDCl₃) δ: 1.34 (1H, d, J = 3.6 Hz), 1.65-1.73 (2H, m), 1.17-1.85 (2H, m), 2.03-2.12 (2H, m), 2.32-2.40 (2H, m), 2.54 (1H, s), 3.81 (3H, s), 4.00-4.10 (1H, m), 6.46 (1H, s), 6.85 (2H, d, J = 8.8 Hz), 7.19-7.24 (4H, m), 7.28-7.31 (3H, m).<br>ESI-MS: m/z = 365 (M + H)⁺ |
| 33 | | ¹H-NMR (400 MHz, CDCl₃) δ: 1.34 (1H, d, J = 3.6 Hz), 1.62-1.73 (2H, m), 1.77-1.85 (2H, m), 2.03-2.12 (2H, m), 2.31-2.40 (5H, m), 2.57 (1H, s), 4.00-4.08 (1H, m), 6.61 (1H, s), 7.12 (2H, d, J = 8.4 Hz), 7.17 (2H, d, J = 8.8 Hz), 7.21-7.24 (2H, m), 7.28-7.30 (3H, m).<br>ESI-MS: m/z = 349 (M + H)⁺ |
| 34 | | ¹H-NMR (400 MHz, CDCl₃) δ: 1.79-2.00 (6H, m), 2.03-2.08 (2H, m), 2.34 (3H, s), 2.57 (1H, s), 3.70-3.79 (1H, m), 6.41 (1H, s), 7.10 (2H, d, J = 8.4 Hz), 7.16 (2H, d, J = 8.4 Hz), 7.27-7.31 (3H, m), 7.19-7.23 (2H, m).<br>ESI-MS: m/z = 349 (M + H)⁺ |
| 35 | | ¹H-NMR (400 MHz, CDCl₃) δ: 1.35 (1H, d, J = 3.6 Hz), 1.62-1.73 (2H, m), 1.75-1.86 (2H, m), 2.02-2.13 (2H, m), 2.29-2.40 (5H, m), 2.58 (1H, s), 3.80 (3H, s), 4.01-4.09 (1H, m), 6.40 (1H, s), 6.82 (2H, d, J = 8.8 Hz), 7.10-7.20 (6H, m). |
| 36 | | ¹H-NMR (400 MHz, CDCl₃) δ: 1.34 (1H, d, J = 5.6 Hz), 1.80-2.10 (8H, m), 2.34 (3H, s), 2.59 (1H, s), 3.68-3.79 (1H, m), 3.80 (3H, s), 6.34 (1H, s), 6.81 (2H, d, J = 8.4 Hz), 7.08-7.20 (6H, m). |

TABLE 5-continued

| Compound | Structural Formula | Compound Data |
|---|---|---|
| 37 | | $^1$H-NMR (400 MHz, CDCl$_3$) δ: 1.48 (1H, s), 1.62-1.72 (2H, m), 1.73-1.83 (2H, m), 2.02-2.12 (2H, m), 2.30-2.39 (2H, m), 2.57 (1H, s), 3.82 (3H, s), 4.02-4.06 (1H, m), 6.42 (1H, s), 6.84 (2H, d, J = 8.8 Hz), 7.13 (2H, d, J = 12.0 Hz), 7.23 (2H, d, J = 8.8 Hz), 7.29 (2H, d, J = 8.8 Hz). ESI-MS: m/z = 399 (M + H)$^+$ |
| 38 | | $^1$H-NMR (400 MHz, CDCl$_3$) δ: 1.79-1.99 (6H, m), 2.03-2.07 (3H, m), 3.70-3.79 (1H, m), 3.81 (3H, s), 6.37 (1H, s), 6.84 (2H, d, J = 8.8 Hz), 7.14 (2H, d, J = 8.8 Hz), 7.22 (2H, d, J = 8.8 Hz), 7.29 (2H, d, J = 8.8 Hz). ESI-MS: m/z = 399 (M + H)$^+$ |
| 39 | | $^1$H-NMR (400 MHz, CDCl$_3$) δ: 1.38 (1H, s), 1.64-1.74 (2H, m), 1.76-1.85 (2H, m), 2.03-2.13 (2H, m), 2.31-2.40 (2H, m), 2.58 (1H, s), 3.81 (3H, s), 4.06 (1H, s), 6.42 (1H, s), 6.82 (2H, d, J = 8.8 Hz), 7.14 (2H, d, J = 8.8 Hz), 7.28-7.37 (5H, m). ESI-MS: m/z = 365 (M + H)$^+$ |
| 40 | | $^1$H-NMR (400 MHz, CDCl$_3$) δ: 1.47 (1H, s), 1.79-1.99 (6H, m), 2.03-2.07 (2H, m), 2.59 (1H, s), 3.70-3.79 (1H, m), 3.80 (3H, s), 6.37 (1H, s), 6.82 (2H, d, J = 8.6 Hz), 7.13 (2H, d, J = 8.6 Hz), 7.27-7.36 (5H, m). ESI-MS: m/z = 365 (M + H)$^+$ |

(Compound 41 and Compound 42)

As Compound 41, 1-(4-(4-methoxyphenyl)-5-(p-tolyl)thiazol-2-yl)cyclohexan-trans-1,4-diol:

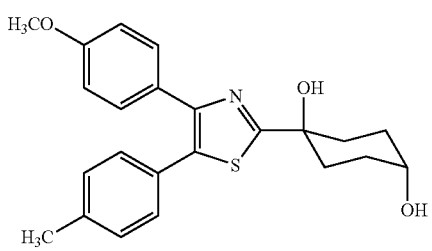 [SMILES: COc1ccc(-c2nc(C3(O)CCC(O)CC3)sc2-c2ccc(C)cc2)cc1]

was synthesized by the following procedure. As Compound 42, 1-(4-(4-methoxyphenyl)-5-(p-tolyl)thiazol-2-yl)cyclohexan-cis-1,4-diol:

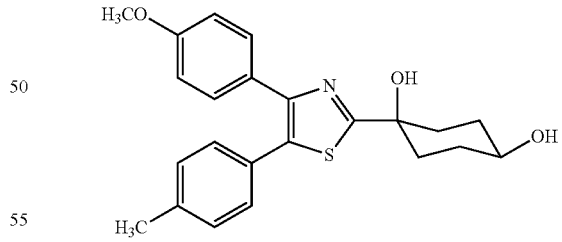

was synthesized by the following procedure.

Sodium borohydride (36 mg, 0.943 mmol) was added to a solution of 4-hydroxy-4-(4-(4-methoxyphenyl)-5-(p-tolyl)thiazol-2-yl)cyclohexan-1-one (Intermediate 83) (186 mg, 0.471 mmol) in methanol (4.7 mL), and the resulting mixture was stirred at room temperature for 1 hour. The reaction solution was concentrated under reduced pressure, and thereafter dissolved in ethyl acetate, and washed with distilled water and brine. The organic layer was dried over anhydrous sodium sulfate, and concentrated under reduced pressure.

The residue was purified by flash chromatography (silica gel, n-hexane/ethyl acetate) to obtain Compound 41 (42 mg, 0.106 mmol, 23%) and Compound 42 (136 mg, 0.344 mmol, 73%) as a white solid, respectively.

Compound 41: $^1$H-NMR (400 MHz, CDCl$_3$) δ: 1.53-1.57 (1H, m), 1.76-1.87 (4H, m), 2.05-2.12 (2H, m), 2.35-2.42 (2H, m), 2.36 (3H, s), 3.15 (1H, br), 3.80 (3H, s), 4.10-4.14 (1H, m), 6.80-6.84 (2H, m), 7.13 (2H, d, J=8.0 Hz), 7.24 (2H, d, J=8.0 Hz), 7.45-7.49 (2H, m).

IR (KBr, cm$^{-1}$): 3409, 2923, 1613, 1515, 1252, 1179, 1004, 815.

ESI-MS: m/z=396 (M+H)$^+$

Compound 42: $^1$H-NMR (400 MHz, CDCl$_3$) δ: 1.48 (1H, d, J=4.8 Hz), 1.82-1.89 (2H, m), 1.95-2.01 (2H, m), 2.05-2.09 (4H, m), 2.36 (3H, s), 3.01 (1H, s), 3.76-3.82 (1H, m), 3.80 (3H, s), 6.80-6.83 (2H, m), 7.13 (2H, d, J=8.0 Hz), 7.22 (2H, d, J=8.0 Hz), 7.43-7.47 (2H, m).

IR (KBr, cm$^{-1}$): 3418, 2938, 1611, 1515, 1249, 1177, 1058, 816.

ESI-MS: m/z=396 (M+H)$^+$ (Compound 43 and Compound 44)

As Compound 43, 4-(4,5-bis(4-methoxyphenyl)oxazol-2-yl) cyclohexan-cis-1,4-diol:

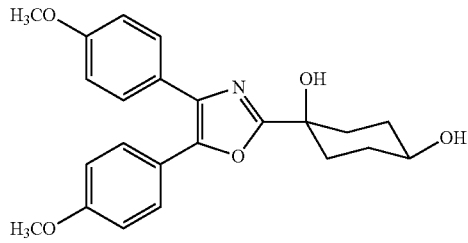 [SMILES: COc1ccc(-c2nc(C3(O)CCC(O)CC3)oc2-c2ccc(OC)cc2)cc1]

was synthesized by the following procedure. As Compound 44, 4-(4,5-bis(4-methoxyphenyl)oxazol-2-yl)cyclohexan-trans-1,4-diol:

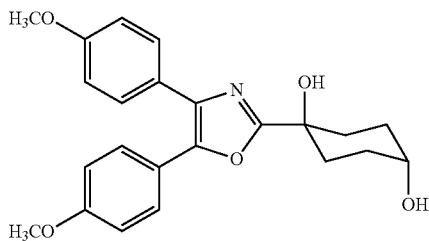

was synthesized by the following procedure.

Sodium borohydride (47 mg, 1.24 mmol) was added to a solution of 4-(4,5-bis(4-methoxyphenyl)oxazol-2-yl)-4-hydroxycyclohexan-1-one (Intermediate 82) (395 mg, 1.00 mmol) in methanol (20 mL), and the resulting mixture was stirred at room temperature for 16 hours. The reaction solution was concentrated under reduced pressure, and distilled water was added to the residue, followed by extraction of the resulting mixture with ethyl acetate. The organic layer was dried over anhydrous magnesium sulfate, and concentrated under reduced pressure. The residue was purified by flash chromatography (silica gel, n-hexane/ethyl acetate) to obtain Compound 43 (207 mg, 0.523 mmol, 52%) and Compound 44 (73 mg, 0.18 mmol, 18%) as a white solid, respectively.

Compound 43: $^1$H-NMR (400 MHz, CDCl$_3$) δ: 1.49 (1H, brs), 1.78-2.13 (8H, m), 2.76 (1H, s), 3.72-3.78 (1H, m), 3.83 (6H, s), 6.89 (2H, d, J=8.8 Hz), 6.90 (2H, d, J=8.8 Hz), 7.49 (2H, d, J=8.8 Hz), 7.55 (2H, d, J=8.8 Hz).

IR (KBr, cm$^{-1}$): 3364, 1615, 1599, 1520, 1500, 1302, 1252, 1176, 1069, 1053, 1028, 965, 833.

ESI-MS: m/z=396 (M+H)$^+$

Compound 44: $^1$H-NMR (400 MHz, CDCl$_3$) δ: 1.63-1.75 (2H, m), 1.78-1.88 (2H, m), 2.01-2.12 (2H, m), 2.44-2.53 (2H, m), 2.67 (1H, s), 4.00-4.07 (1H, m), 6.89 (2H, d, J=8.8 Hz), 6.90 (2H, d, J=8.8 Hz), 7.51 (2H, d, J=8.8 Hz), 7.57 (2H, d, J=8.8 Hz).

IR (KBr, cm$^{-1}$): 3356, 1613, 1600, 1520, 1503, 1254, 1182, 1033, 999, 966, 834.

ESI-MS: m/z=396 (M+H)$^+$ (Compound 45 and Compound 46)

As Compound 45, 1-(4-(4-methoxyphenyl)-5-(p-tolyl)thiazol-2-yl)-4-(trifluoromethyl)cyclohexan-trans-1,4-diol:

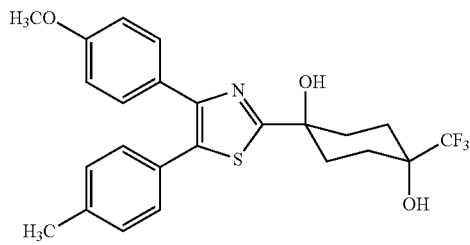 [SMILES: COc1ccc(-c2nc(C3(O)CCC(O)(C(F)(F)F)CC3)sc2-c2ccc(C)cc2)cc1]

was synthesized by the following procedure. As Compound 46, 1-(4-(4-methoxyphenyl)-5-(p-tolyl)thiazol-2-yl)-4-(trifluoromethyl)cyclohexan-cis-1,4-diol:

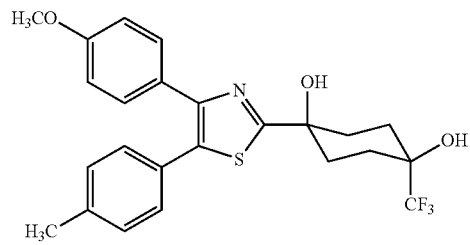

was synthesized by the following procedure.

To a solution of 4-hydroxy-4-(4-(4-methoxyphenyl)-5-(p-tolyl)thiazol-2-yl)cyclohexan-1-one (Intermediate 83) (199 mg, 0.506 mmol) and Ruppert's reagent (0.187 mL, 1.26 mmol) in tetrahydrofuran (2.5 mL), a 1.0 M tetrabutylammonium fluoride/tetrahydrofuran solution (0.051 mL, 0.051 mmol) was added at room temperature, and the resulting mixture was stirred for 10 minutes. The reaction solution was concentrated under reduced pressure, and thereafter dissolved in tetrahydrofuran (3.0 mL). Distilled water (0.2 mL) and a 1.0 M tetrabutylammonium fluoride/tetrahydrofuran solution (1.02 mL, 1.02 mmol) were added thereto, and the resulting mixture was stirred at room temperature for 30 minutes. Distilled water was added to the reaction solution, and the resulting solution was extracted with ethyl acetate, followed by washing with brine. The organic layer was dried over anhydrous sodium sulfate, and concentrated under reduced pressure. The residue was purified by flash chromatography (silica gel, n-hexane/ethyl acetate) to obtain Compound 45 (70 mg, 0.151 mmol, 30%) and Compound 46 (132 mg, 0.285 mmol, 56%) as a white solid, respectively.

Compound 45: $^1$H-NMR (400 MHz, CDCl$_3$) δ: 1.79-1.84 (2H, m), 1.90 (1H, s), 1.96-2.01 (2H, m), 2.21-2.33 (4H, m), 2.37 (3H, s), 3.28 (1H, s), 3.80 (3H, s), 6.80-6.84 (2H, m), 7.13 (2H, d, J=8.0 Hz), 7.23 (2H, d, J=8.0 Hz), 7.44-7.48 (2H, m).

IR (KBr, cm$^{-1}$): 3460, 2940, 1610, 1515, 1494, 1442, 1310, 1245, 1175, 1035, 1005, 837, 813

ESI-MS: m/z=464 (M+H)$^+$

Compound 46: $^1$H-NMR (400 MHz, CDCl$_3$) δ: 1.90-1.96 (2H, m), 1.97 (1H, br), 2.16-2.23 (2H, m), 2.28-2.36 (4H, m), 2.37 (3H, s), 2.81 (1H, br), 3.80 (3H, s), 6.80-6.83 (2H, m), 7.14 (2H, d, J=8.0 Hz), 7.26 (2H, d, J=8.0 Hz), 7.44-7.48 (2H, m).

IR (KBr, cm$^{-1}$): 3419, 2940, 1611, 1515, 1443, 1290, 1250, 1175, 1120, 1066, 993, 837, 814

ESI-MS: m/z=464 (M+H)$^+$

The following compounds were synthesized in the same manner as in the synthesis of the above-described Compound 2 and Compound 3.

TABLE 6

| Compound | Structural Formula | Compound Data |
|---|---|---|
| 47 | | $^1$H-NMR (400 MHz, CDCl3) δ: 1.23 (3H, t, J = 7.6 Hz), 1.33 (1H, br), 1.64-1.73 (2H, m), 1.77-1.84 (2H, m), 2.03-2.12 (2H, m), 2.31-2.40 (2H, m), 2.55 (1H, s), 2.63 (2H, q, J = 7.6 Hz), 3.81 (3H, s), 4.02-4.07 (1H, m), 6.43 (1H, s), 6.83-6.89 (2H, m), 7.12 (4H, s), 7.19-7.28 (2H, m). ESI-MS: m/z = 393 (M + H)$^+$ |
| 48 | | $^1$H-NMR (400 MHz, CDCl3) δ: 1.23 (3H, t, J = 7.6 Hz), 1.41 (1H, d, J = 4.4 Hz), 1.80-2.09 (8H, m), 2.55 (1H, s), 2.63 (2H, q, J = 7.6 Hz), 3.69-3.83 (4H, m), 6.38 (1H, s), 6.82-6.87 (2H, m), 7.12 (4H, s), 7.17-7.28 (2H, m). ESI-MS: m/z = 393 (M + H)$^+$ |
| 49 | | $^1$H-NMR (400 MHz, CDCl$_3$) δ: 1.33 (1H, br), 1.65-1.82 (4H, m), 2.03-2.12 (2H, m), 2.30-2.39 (5H, m), 2.43 (1H, s), 4.03-4.11 (1H, m), 6.48 (1H, s), 7.10-7.19 (4H, m), 7.41-7.45 (2H, m), 7.57-7.61 (2H, m). ESI-MS: m/z = 374 (M + H)$^+$ |
| 50 | | $^1$H-NMR (400 MHz, CDCl$_3$) δ: 1.45 (1H, br), 1.81-2.07 (8H, m), 2.38 (3H, s), 2.45 (1H, br), 3.70-3.80 (1H, m), 6.43 (1H, s), 7.09-7.18 (4H, m), 7.40-7.44 (2H, m), 7.57-7.61 (2H, m). ESI-MS: m/z = 374 (M + H)$^+$ |
| 51 | | $^1$H-NMR (400 MHz, CDCl$_3$) δ: 1.62-1.90 (4H, m), 2.02-2.16 (2H, m), 2.31-2.49 (3H, m), 3.83 (3H, s), 4.03-4.11 (1H, m), 6.55 (1H, s), 6.86-6.90 (2H, m), 7.16-7.22 (2H, m), 7.29-7.33 (2H, m), 7.53-7.60 (2H, m). ESI-MS: m/z = 390 (M + H)$^+$ |

TABLE 6-continued

| Compound | Structural Formula | Compound Data |
|---|---|---|
| 52 | | $^1$H-NMR (400 MHz, CDCl$_3$) δ: 1.43 (1H, br), 1.80-2.10 (8H, m), 2.43 (1H, s), 3.70-3.80 (1H, m), 3.83 (3H, s), 6.51 (1H, s), 6.85-6.91 (2H, m), 7.15-7.21 (2H, m), 7.27-7.33 (2H, m), 7.55-7.61 (2H, m).<br>ESI-MS: m/z = 390 (M + H)$^+$ |
| 53 | | $^1$H-NMR (400 MHz, CDCl$_3$) δ: 1.32 (1H, br), 1.65-1.72 (2H, m), 1.77-1.83 (2H, m), 2.04-2.11 (2H, m), 2.30-2.39 (5H, m), 2.48 (1H, br), 3.89 (3H, s), 4.02-4.08 (1H, m), 6.43 (1H, s), 6.88 (1H, t, J = 8.8 Hz), 6.93-7.02 (1H, m), 7.08-7.15 (5H, m).<br>ESI-MS: m/z = 397 (M + H)$^+$ |
| 54 | | $^1$H-NMR (400 MHz, CDCl$_3$) δ: 1.41 (1H, br), 1.80-2.08 (8H, m), 2.35 (3H, s), 2.48 (1H, s), 3.70-3.80 (1H, m), 3.89 (3H, s), 6.38 (1H, s), 6.88 (1H, t, J = 8.8 Hz), 6.96-7.01 (1H, m), 7.06-7.14 (5H, m).<br>ESI-MS: m/z = 397 (M + H)$^+$ |
| 55 | | $^1$H-NMR (400 MHz, CDCl$_3$) δ: 1.63-1.84 (4H, m), 2.03-2.12 (2H, m), 2.26 (3H, d, J =1.6 Hz), 2.31-2.41 (2H, m), 2.51 (1H, br), 3.82 (3H, s), 4.03-4.08 (1H, m), 6.44 (1H, s), 6.84-6.90 (4H, m), 7.08 (1H, t, J = 8.0 Hz), 7.18-7.23 (2H, m).<br>ESI-MS: m/z = 397 (M + H)$^+$ |
| 56 | | $^1$H-NMR (400 MHz, CDCl$_3$) δ: 1.41 (1H, d, J = 4.8 Hz), 1.81-2.08 (8H, m), 2.25 (3H, d, J = 1.6 Hz), 2.51 (1H, s), 3.69-3.78 (1H, m), 3.82 (3H, s), 6.39 (1H, s), 6.84-6.89 (4H, m), 7.09 (1H, t, J = 7.6 Hz), 7.17-7.24 (2H, m).<br>ESI-MS: m/z = 397 (M + H)$^+$ |

(Compound 58)

As Compound 58, ethyl 4-hydroxy-4-(1-(4-methoxyphenyl)-5-(p-tolyl)-1H-pyrazol-3-yl)-cis-cyclohexanecarboxylate:

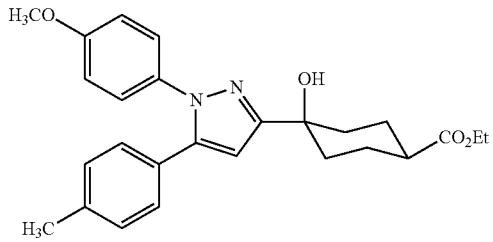

was synthesized by the following procedure.

Potassium carbonate (41.4 mg, 0.3 mmol) and ethyl iodide (24.8 μl, 0.3 mmol) were added to a solution of 4-hydroxy-4-(1-(4-methoxyphenyl)-5-(p-tolyl)-1H-pyrazol-3-yl)-cis-cyclohexanecarboxylic acid (Compound 16) (41.6 mg, 0.10 mmol) in DMF (1.0 ml), and the resulting mixture was stirred for 2 hours. Brine was added to the reaction solution, and the resulting solution was extracted with ethyl acetate. The organic layer was washed with brine, dried over anhydrous sodium sulfate, and concentrated under reduced pressure. The residue was purified by flash column chromatography (silica gel, n-hexane/ethyl acetate) to obtain Compound 58 (44.1 mg, 0.10 mmol, 97%) as a white amorphous product.

$^1$H-NMR (400 MHz, CDCl$_3$) δ: 1.27 (3H, t, J=6.8 Hz), 1.85-2.09 (8H, m), 2.33 (3H, s), 2.34-2.41 (1H, m), 2.59 (1H, s), 3.80 (3H, s), 4.15 (2H, q, J=6.8 Hz), 6.38 (1H, s), 6.84 (2H, d, J=8.8 Hz), 7.09-7.09 (4H, m), 7.20 (2H, d, J=8.8 Hz).

ESI-MS: m/z=435 (M+H)$^+$

Prodrugs of the above-described Compound 3 were synthesized (Compounds 59 to 70).

(Compound 59)

As Compound 59, 4-hydroxy-4-(1-(4-methoxyphenyl)-5-(p-tolyl)-1H-pyrazol-3-yl)-cis-cyclohexyl dimethylcarbamate (Compound 59):

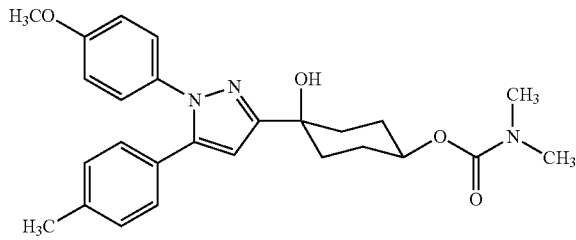

was synthesized by the following procedure.

A solution of 1-(1-(4-methoxyphenyl)-5-(p-tolyl)-1H-pyrazol-3-yl)cyclohexan-cis-1,4-diol (Compound 3) (230 mg, 0.60 mmol) in tetrahydrofuran (6.0 ml) was stirred for 10 minutes under ice-cooling. Sodium hydride (26.4 mg, 0.66 mmol) was added to the reaction solution, and the resulting mixture was stirred at the same temperature for 20 minutes. Dimethylcarbamoyl chloride (84 μL, 0.9 mmol) was added dropwise thereto, and the resulting mixture was stirred at room temperature for 3 hours. Thereafter, brine was added to the reaction solution, and the resulting solution was extracted with ethyl acetate. The organic layer was washed with brine, dried using anhydrous sodium sulfate, and concentrated under reduced pressure. The residue was purified by flash column chromatography (silica gel, n-hexane/ethyl acetate) to obtain Compound 59 (95.6 mg, 0.21 mmol, 35%) as a pale yellow amorphous product.

$^1$H-NMR (400 MHz, CDCl$_3$) δ: 1.93-2.04 (8H, m), 2.33 (3H, s), 2.71 (1H, s), 2.92 (6H, s), 3.80 (3H, s), 4.73-4.79 (1H, m), 6.37 (1H, s), 6.84 (2H, d, J=8.8 Hz), 7.09-7.09 (4H, m), 7.20 (2H, J=8.8 Hz).

ESI-MS: m/z=450 (M+H)$^+$ (Compound 60)

As Compound 60, cyclohexyl 4-hydroxy-4-(1-(4-methoxyphenyl)-5-(p-tolyl)-1H-pyrazol-3-yl)-cis-cyclohexyl carbonate (Compound 60):

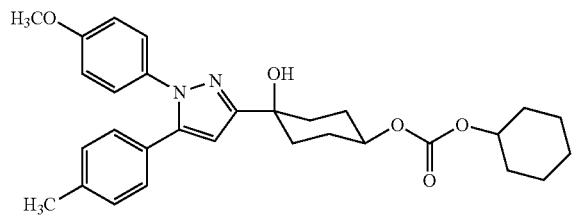 [SMILES: COc1ccc(-n2nc(C3(O)CCC(OC(=O)OC4CCCCC4)CC3)cc2-c2ccc(C)cc2)cc1]

was synthesized by the following procedure.

A solution of 1-(1-(4-methoxyphenyl)-5-(p-tolyl)-1H-pyrazol-3-yl)cyclohexan-cis-1,4-diol (Compound 3) (250 mg, 0.66 mmol) in tetrahydrofuran (2.2 ml) was cooled in ice, and sodium hydride (63.4 mg, 1.45 mmol) was added thereto, followed by stifling the resulting mixture at the same temperature for 10 minutes. Cyclohexyl 1-iodoethyl carbonate (354 mg, 1.18 mmol) was then added to the mixture, and the resulting mixture was stirred at room temperature for 12 hours. Brine was added to the reaction solution, and the resulting solution was extracted with ethyl acetate. The organic layer was washed with brine, dried using anhydrous sodium sulfate, and concentrated under reduced pressure. The residue was purified by flash column chromatography (silica gel, n-hexane/ethyl acetate) to obtain Compound 60 (161 mg, 0.29 mmol, 44%) as a white amorphous product.

$^1$H-NMR (400 MHz, CDCl$_3$) δ: 1.23-1.28 (4H, m), 1.31-1.40 (2H, m), 1.44-1.56 (4H, m), 1.70-1.79 (4H, m), 1.93-2.08 (4H, m), 2.32 (3H, s), 2.82 (1H, s), 3.79 (3H, s), 4.57-4.64 (1H, m), 4.67-4.71 (1H, m), 6.38 (1H, s), 6.84 (2H, d, J=8.4 Hz), 7.08-7.08 (4H, m), 7.19 (2H, d, J=8.4 Hz).

ESI-MS: m/z=505 (M+H)$^+$

The following compounds were synthesized in the same manner as in the synthesis of the above-described Compound 59 and Compound 60.

TABLE 7

| Compound | Structural Formula | Compound Data |
|---|---|---|
| 61 | | $^1$H-NMR (400 MHz, CDCl3) δ: 1.32 (3H, t, J = 8.0 Hz), 1.97-2.09 (8H, m), 2.33 (3H, s), 2.62 (1H, s), 3.80 (3H, s), 4.20 (2H, q, J = 8.0 Hz), 4.69-4.71 (1H, m), 6.37 (1H, s), 6.84 (2H, d, J = 8.8 Hz), 7.09-7.09 (4H, m), 7.20 (2H, J = 8.8 Hz).<br>ESI-MS: m/z = 451 (M + H)$^+$ |
| 62 | | $^1$H-NMR (400 MHz, CDCl3) δ: 1.21 (9H, s), 1.92-2.06 (9H, m), 2.33 (3H, s), 3.80 (3H, s), 4.80-4.86 (1H, m), 6.38 (1H, s), 6.84 (2H, d, J = 8.4 Hz), 7.09-7.09 (4H, m), 7.20 (2H, J = 8.4 Hz).<br>ESI-MS: m/z = 463 (M + H)$^+$ |

(Compound 63)

As Compound 63, succinic acid mono-4-hydroxy-4-(1-(4-methoxyphenyl)-5-(p-tolyl)-1H-pyrazol-3-yl)-cis-cyclohexyl ester:

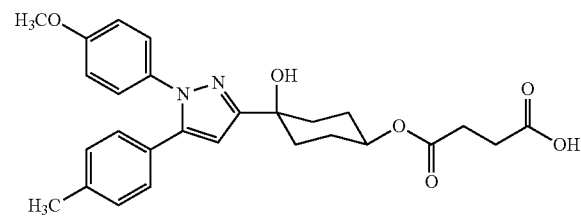 [SMILES: COc1ccc(-n2nc(C3(O)CCC(OC(=O)CCC(=O)O)CC3)cc2-c2ccc(C)cc2)cc1]

was synthesized by the following procedure.

Sodium hydride (63.4 mg, 1.45 mmol) was added to a solution of 1-(1-(4-methoxyphenyl)-5-(p-tolyl)-1H-pyrazol-3-yl)cyclohexan-cis-1,4-diol (Compound 3) (250 mg, 0.66 mmol) in DMF (3.3 ml), and the resulting mixture was stirred for 30 minutes. Succinic anhydride (99 mg, 0.99 mmol) was added thereto, and the resulting mixture was stirred for 12 hours. Thereafter, 1 M hydrochloric acid and ethyl acetate were added to the reaction solution, and the resulting solution was extracted with ethyl acetate. The organic layer was washed with brine, dried using anhydrous sodium sulfate, and concentrated under reduced pressure. The residue was purified by flash column chromatography (silica gel, n-hexane/ethyl acetate) to obtain Compound 63 (87.0 mg, 0.18 mmol, 28%) as a white amorphous product.

$^1$H-NMR (400 MHz, CDCl$_3$) δ: 1.86-1.88 (2H, m), 1.96-2.02 (4H, m), 2.08-2.11 (3H, m), 2.32 (3H, s), 2.58-2.64 (4H, m), 3.81 (3H, s), 4.82-4.88 (1H, m), 6.38 (1H, s), 6.84 (2H, d, J=8.0 Hz), 7.09-7.09 (4H, m), 7.18 (2H, J=8.0 Hz).

ESI-MS: m/z=479 (M+H)$^+$ (Compound 64)

As Compound 64, cyclohexyl (4-hydroxy-4-(1-(4-methoxyphenyl)-5-(p-tolyl)-1H-pyrazol-3-yl)-cis-cyclohexyloxy)ethyl carbonate:

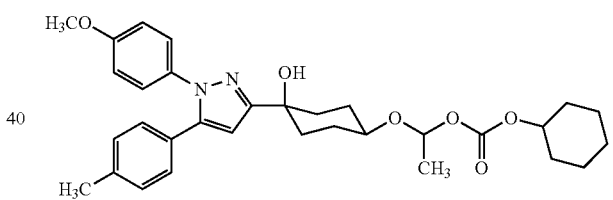

was synthesized by the following procedure.

Cyclohexyl 1-iodoethyl carbonate (567 mg, 1.90 mmol), diisopropylethylamine (460 μL, 2.64 mmol) and silver chloride (273 mg, 1.90 mmol) were added to a solution of 1-(1-(4-methoxyphenyl)-5-(p-tolyl)-1H-pyrazol-3-yl)cyclohexan-cis-1,4-diol (Compound 3) (400 mg, 1.05 mmol) in dichloroethane (5.4 ml), and the resulting mixture was stirred at 80° C. for 12 hours. The mixture was allowed to cool to room temperature, and the reaction solution was filtered through Celite. To the filtrate, 1 M hydrochloric acid and ethyl acetate were added, and thereafter the resulting solution was extracted with ethyl acetate. The organic layer was washed with brine, dried using anhydrous sodium sulfate, and concentrated under reduced pressure. The residue was purified by flash column chromatography (silica gel, n-hexane/ethyl acetate) to obtain Compound 64 (31.9 mg, 0.058 mmol, 5.1%) as a white amorphous product.

$^1$H-NMR (400 MHz, CDCl$_3$) δ: 1.15-1.34 (9H, m), 1.48-1.65 (4H, m), 1.83-1.98 (8H, m), 2.33 (3H, s), 2.49 (1H, s), 3.52-3.58 (1H, m), 3.64-3.71 (1H, m), 3.81 (3H, s), 4.92 (1H, q, J=5.2 Hz), 6.39 (1H, s), 6.84 (2H, d, J=8.8 Hz), 7.09-7.09 (4H, m), 7.19 (2H, J=8.8 Hz).

ESI-MS: m/z=549 (M+H)$^+$

The following compounds were synthesized in the same manner as in the synthesis of the above-described Compound 59 and Compound 60.

methanol (2.00 mL), 10% palladium/carbon (6.16 mg, 50 wt %) was added at room temperature, and the resulting mixture was stirred under hydrogen atmosphere for 14 hours. The

TABLE 8

| Compound | Structural Formula | Compound Data |
|---|---|---|
| 65 | | $^1$H-NMR (400 MHz, CDCl$_3$) δ: 1.26 (3H, t, J = 5.0 Hz), 1.33 (3H, d, J = 4.8 Hz), 1.86-2.01 (8H, m), 2.33 (3H, s), 2.49 (1H, s), 3.49-3.53 (1H, m), 3.65-3.70 (2H, m), 3.80 (3H, s), 4.84 (1H, q, J = 4.8 Hz), 6.39 (1H, s), 6.84 (2H, d, J = 8.0 Hz), 7.09-7.09 (4H, m), 7.19 (2H, J = 8.0 Hz). ESI-MS: m/z = 495 (M + H)$^+$ |
| 66 | | $^1$H-NMR (400 MHz, CDCl$_3$) δ: 1.23 (9H, s), 1.89-2.00 (6H, m), 2.05-2.08 (2H, m), 2.33 (3H, s), 2.48 (1H, s), 3.67-3.71 (1H, m), 3.81 (3H, s), 5.39 (2H, s), 6.38 (1H, s), 6.84 (2H, d, J = 9.2 Hz), 7.09-7.09 (4H, m), 7.19 (2H, J = 9.2 Hz). ESI-MS: m/z = 493 (M + H)$^+$ |

(Compound 67)

As Compound 67, 4-hydroxy-4-(1-(4-methoxyphenyl)-5-(p-tolyl)-1H-pyrazol-3-yl)-cis-cyclohexyl 2-aminoacetate:

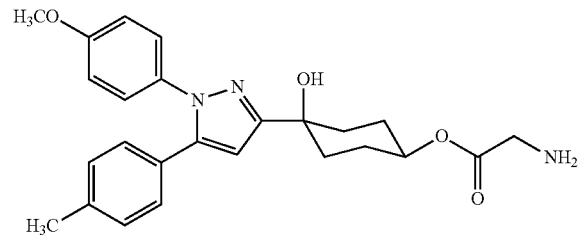 [SMILES: COc1ccc(-n2nc(C3(O)CCC(OC(=O)CN)CC3)cc2-c2ccc(C)cc2)cc1]

reaction solution was filtered through Celite, and the filtrate was concentrated under reduced pressure. The residue was purified by flash chromatography (NH silica gel, chloroform/methanol) to obtain Compound 67 (18.4 mg, 0.042 mmol, 73%) as a colorless amorphous product.

$^1$H-NMR (400 MHz, CDCl$_3$) δ: 1.58-1.82 (2H, m), 1.88-2.12 (9H, m), 2.33 (3H, s), 3.43 (2H, s), 3.81 (3H, s), 4.88-4.94 (1H, m), 6.37 (1H, s), 6.83-6.87 (2H, m), 7.09-7.11 (4H, m), 7.18-7.22 (2H, m).

ESI-MS: m/z=436 (M+H)$^+$

The following compound was synthesized in the same manner as in the synthesis of Compound 67 as described above.

TABLE 9

| Compound | Structural Formula | Compound Data |
|---|---|---|
| 68 | | $^1$H-NMR (400 MHz, CDCl$_3$) δ: 0.93 (3H, d, J = 6.4 Hz), 1.00 (3H, d, J = 6.4 Hz), 1.90-2.10 (9H, m), 2.34 (3H, s), 3.31 (1H, d, J = 8.0 Hz), 3.81 (3H, s), 4.88-4.94 (1H, s), 6.36, (1H, s), 6.83-6.87 (2H, m), 7.09-7.11 (4H, m), 7.18-7.22 (2H, m). ESI-MS: m/z = 460 (M − OH)$^+$ | was synthesized by the following procedure.

To a solution of 4-hydroxy-4-(1-(4-methoxyphenyl)-5-(p-tolyl)-1H-pyrazol-3-yl)-cis-cyclohexyl 2-benzyloxycarbonylaminoacetate (Intermediate 57) (33.2 mg, 0.058 mmol) in (Compound 69)

As Compound 69, (S)-4-hydroxy-4-(1-(4-methoxyphenyl)-5-(p-tolyl)-1H-pyrazol-3-yl)-cis-cyclohexyl 2-amino-3-methylbutanoate:

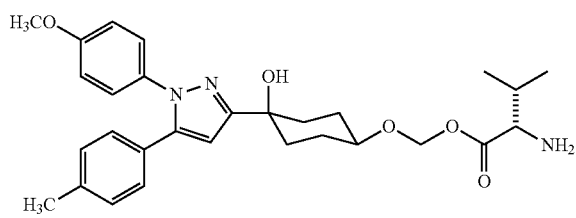

was synthesized by the following procedure.

To a mixed solution of (S)-4-hydroxy-4-(1-(4-methoxyphenyl)-5-(p-tolyl)-1H-pyrazol-3-yl)cyclohexyloxy)methyl 2-(benzyloxycarbonylamino)-3-methylbutanoate (Intermediate 59) (122 mg, 0.190 mmol) in dioxane/ethanol (2.00 mL/2.00 mL), 2,2'-bipyridyl (15.0 mg, 0.096 mmol) and 10% palladium/carbon (49.0 mg, 40 wt %) were added at room temperature, and the resulting mixture was stirred under hydrogen atmosphere for 14 hours. The reaction solution was filtered through Celite, and the filtrate was concentrated under reduced pressure. The residue was purified by flash chromatography (silica gel, chloroform/methanol) to obtain Compound 69 (38.6 mg, 0.076 mmol, 40%) as a colorless amorphous product.

$^1$H-NMR (400 MHz, CDCl$_3$) δ: 0.92 (3H, d, J=6.8 Hz), 1.02 (3H, d, J=6.8 Hz), 1.90-2.12 (9H, m), 2.34 (3H, s), 3.32-3.34 (1H, m), 3.67-3.76 (1H, m), 3.81 (3H, s), 5.41 (1H, d, J=6.4 Hz), 5.47 (1H, d, J=6.4 Hz), 6.38, (1H, s), 6.83-6.87 (2H, m), 7.09-7.12 (4H, m), 7.18-7.22 (2H, m).

ESI-MS: m/z=490 (M−OH)$^+$ (Compound 70)

As Compound 70, 4-hydroxy-4-(1-(4-methoxyphenyl)-5-(p-tolyl)-1H-pyrazol-3-yl)-cis-cyclohexyl dihydrogen phosphate:

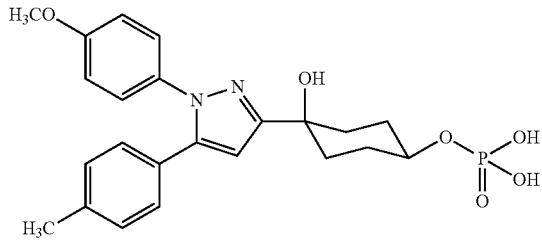 [SMILES: COc1ccc(-n2nc(C3(O)CCC(OP(=O)(O)O)CC3)cc2-c2ccc(C)cc2)cc1]

was synthesized by the following procedure.

To a mixed solution of dibenzyl 4-hydroxy-4-(1-(4-methoxyphenyl)-5-(p-tolyl)-1H-pyrazol-3-yl)-cis-cyclohexyl phosphate (Intermediate 60) (251 mg, 0.393 mmol), methanol (2.6 mL) and ethyl acetate (2.6 mL), 10% palladium/carbon (41.8 mg, 50 wt %) was added, and the resulting mixture was stirred under hydrogen atmosphere at room temperature for 2.5 hours. The reaction solution was filtered through Celite, and the filtrate was concentrated under reduced pressure. The residue was recrystallized from dichloromethane/diethyl ether to obtain Compound 70 (97.2 mg, 0.212 mmol, 54%) as a white solid.

$^1$H-NMR (400 MHz, DMSO-d$_6$) δ: 1.68-1.98 (8H, m), 2.28 (3H, s), 3.76 (3H, s), 4.13 (1H, br), 4.92 (1H, br), 6.53 (1H, s), 6.91-6.95 (2H, m), 7.08-7.17 (6H, m).

ESI-MS: m/z=459 (M+H)$^+$ (Intermediate 1)

As Intermediate 1,8-ethinyl-1,4-dioxaspiro[4.5]decan-8-ol:

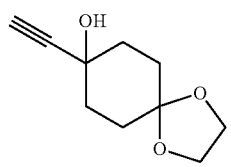

was synthesized by the following procedure.

To a solution of trimethylsilylacetylene (27.1 mL, 0.192 mol) in tetrahydrofuran (300 mL), 2.77 M n-butyllithium (a solution in n-hexane, 69.3 mL, 0.192 mol) was added dropwise at −76° C. for 30 minutes, and the resulting mixture was stirred at the same temperature for 30 minutes. Thereafter, a solution of 1,4-dioxaspiro[4.5]decan-8-one (25.0 g, 0.160 mol) in tetrahydrofuran (100 mL) was added dropwise thereto at −74° C. for 30 minutes, and the resulting mixture was stirred at the same temperature for 1 hour and 30 minutes. The reaction solution was poured into a saturated aqueous ammonium chloride solution, and the resulting solution was extracted with ethyl acetate. The organic layer was washed with brine, dried over anhydrous sodium sulfate, and concentrated under reduced pressure.

Methanol (320 mL) was added to the residue to dissolve it, and potassium carbonate (55.3 g, 0.400 mol) was added thereto. The resulting mixture was stirred at room temperature for 2 hours, and the reaction solution was concentrated under reduced pressure. Distilled water was added to the residue, and the resulting solution was extracted with ethyl acetate. The organic layer was washed with distilled water and brine. The organic layer was dried over anhydrous sodium sulfate, and concentrated under reduced pressure. The residue was purified by flash chromatography (silica gel, n-hexane/ethyl acetate) to obtain Intermediate 1 (29.1 g, 0.160 mol, 100%) as a white solid.

$^1$H-NMR (400 MHz, CDCl$_3$) δ: 1.75-2.03 (9H, m), 2.49 (1H, m), 3.95 (4H, s).

ESI-MS: m/z=165 (M−OH)$^+$ (Intermediate 2)

As Intermediate 2,1-(3-hydroxy-3-(p-tolyl)propyn-1-yl) cyclohexanol:

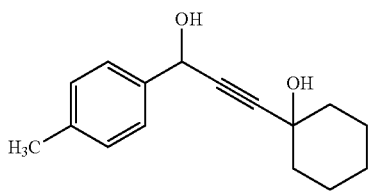 [SMILES: Cc1ccc(C(O)C#CC2(O)CCCCC2)cc1]

was synthesized by the following procedure.

To a solution of 1-ethynylcyclohexanol (500 mg, 4.02 mmol) in tetrahydrofuran (20 mL), 2.77 M n-butyllithium (a solution in n-hexane, 3.6 mL, 9.90 mmol) was added dropwise at −78° C., and the resulting mixture was stirred at the same temperature for 1 hour. To the reaction solution, p-tolualdehyde (0.52 mL, 4.40 mmol) was added at −78° C., and the obtained solution was allowed to warm gradually to room temperature with stifling. Distilled water and 1 M hydrochloric acid were added to the reaction solution to acidify it, and thereafter the resulting solution was extracted with ethyl acetate. The organic layer was dried over anhydrous magnesium sulfate, and concentrated under reduced pressure. The residue was purified by flash chromatography (silica gel, n-hexane/ethyl acetate) to obtain Intermediate 2 (598 mg, 2.44 mmol, 61%) as a pale yellow solid.

$^1$H-NMR (400 MHz, CDCl$_3$) δ: 1.18-1.30 (1H, m), 1.47-1.74 (7H, m), 1.89-1.98 (2H, m), 2.08 (1H, brs), 2.22 (1H, brs), 2.36 (3H, s), 5.47 (1H, s), 7.19 (2H, d, J=8.0 Hz), 7.43 (2H, d, J=8.0 Hz).

ESI-MS: m/z=227 (M−OH)$^+$ (Intermediate 3)

As Intermediate 3,8-(3-hydroxy-3-(p-tolyl)propyn-1-yl)-1,4-dioxaspiro[4.5]decan-8-ol:

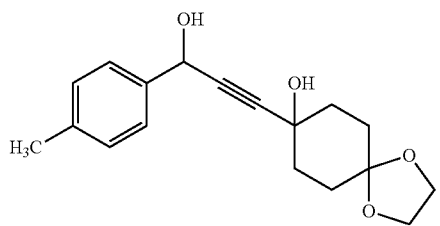

was synthesized by the following procedure.

To a solution of 8-ethinyl-1,4-dioxaspiro[4.5]decan-8-ol (Intermediate 1) (15.0 g, 82.3 mmol) in tetrahydrofuran (165 mL), 2.77 M n-butyllithium (a solution in n-hexane, 62.4 mL, 172.9 mmol) was added dropwise at −72° C. for 25 minutes, and the resulting mixture was stirred at the same temperature for 30 minutes. Then, p-tolualdehyde (10.2 mL, 86.4 mmol) was added dropwise thereto at −72° C. for 5 minutes, and the resulting mixture was stirred at the same temperature for 30 minutes. The reaction solution was allowed to warm to room temperature, and thereafter poured into a saturated aqueous ammonium chloride solution. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 3 (17.7 g, 58.5 mmol, 71%) as an amorphous product.

$^1$H-NMR (400 MHz, CDCl$_3$) δ: 1.72-1.85 (4H, m), 1.90-2.04 (4H, m), 2.35 (3H, s), 2.55 (1H, s), 2.78 (1H, d, J=6.0 Hz), 3.93 (4H, s), 5.44 (1H, d, J=6.0 Hz), 7.17 (2H, d, J=8.0 Hz), 7.40 (2H, d, J=8.0 Hz).

ESI-MS: m/z=285 (M−OH)$^+$ (Intermediate 4)

As Intermediate 4,8-(3-hydroxy-3-(4-methoxyphenyl)propyn-1-yl)-1,4-dioxaspiro[4.5]decan-8-ol:

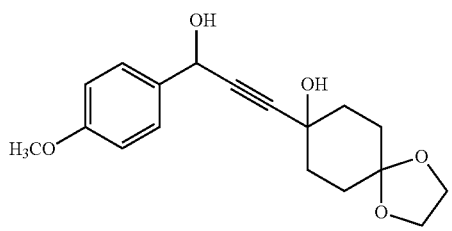

was synthesized by the following procedure.

To a solution of 8-ethinyl-1,4-dioxaspiro[4.5]decan-8-ol (Intermediate 1) (5.02 g, 27.6 mmol) in tetrahydrofuran (100 mL), 2.63 M n-butyllithium (a solution in n-hexane, 22.0 mL, 57.9 mmol) was added dropwise at −72° C. for 15 minutes, and the resulting mixture was stirred at the same temperature for 60 minutes. Then, 4-methoxyaldehyde (3.52 mL, 28.9 mmol) was added dropwise thereto at −72° C. for 10 minutes, and the resulting mixture was stirred at the same temperature for 60 minutes. The reaction solution was allowed to warm to room temperature, and thereafter poured into a saturated aqueous ammonium chloride solution. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 4 (7.46 g, 23.4 mmol, 85%) as an amorphous product.

$^1$H-NMR (400 MHz, CDCl$_3$) δ: 1.73-1.85 (4H, m), 1.91-2.04 (4H, m), 2.32 (1H, s), 2.52 (1H, d, J=6.1 Hz), 3.81 (3H, s), 3.94 (4H, s), 5.44 (1H, d, J=6.1 Hz), 6.89 (2H, d, J=8.5 Hz), 7.44 (2H, d, J=8.5 Hz).

(Intermediate 5)

As Intermediate 5,8-(3-(4-chlorophenyl)-3-hydroxypropyn-1-yl)-1,4-dioxaspiro[4.5]decan-8-ol:

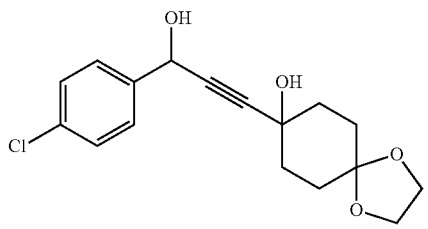 [SMILES: OC(C#CC1(O)CCC2(CC1)OCCO2)c1ccc(Cl)cc1]

was synthesized by the following procedure.

To a solution of 8-ethinyl-1,4-dioxaspiro[4.5]decan-8-ol (Intermediate 1) (5.03 g, 27.6 mmol) in tetrahydrofuran (100 mL), 2.63 M n-butyllithium (a solution in n-hexane, 22.1 mL, 57.9 mmol) was added dropwise at −72° C. for 15 minutes, and the resulting mixture was stirred at the same temperature for 60 minutes. Then, 4-chlorobenzaldehyde (4.06 g, 28.9 mmol) was added dropwise thereto at −72° C. for 10 minutes, and the resulting mixture was stirred at the same temperature for 60 minutes. The reaction solution was allowed to warm to room temperature, and thereafter poured into a saturated aqueous ammonium chloride solution. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 5 (8.13 g, 25.2 mmol, 91%) as an amorphous product.

$^1$H-NMR (400 MHz, CDCl$_3$) δ: 1.68-1.81 (4H, m), 1.86-1.90 (4H, m), 3.55 (1H, s), 3.90 (4H, s), 4.03 (1H, d, J=4.2 Hz), 5.41 (1H, d, J=4.2 Hz), 7.28 (2H, d, J=8.3 Hz), 7.41 (2H, d, J=8.3 Hz).

The following compounds were synthesized in the same manner as in the synthesis of the above-described Intermediates 1 to 5.

TABLE 10

| Intermediate | Structural Formula | Compound Data |
| --- | --- | --- |
| 6 | | $^1$H-NMR (400 MHz, CDCl$_3$) δ: 1.71-1.84 (4H, m), 1.88-2.03 (4H, m), 2.65-3.31 (2H, m), 3.91 (4H, s), 5.47 (1H, d, J = 5.2 Hz), 7.29-7.38 (3H, m), 7.51 (2H, d, J = 8.4 Hz).<br>ESI-MS: m/z = 271 (M − OH)$^+$ |
| 7 | | $^1$H-NMR (400 MHz, CDCl$_3$) δ: 1.63 (1H, s), 1.75-1.83 (4H, m), 1.95-2.05 (4H, m), 2.62 (1H, s), 3.94 (4H, s), 5.56 (1H, s), 7.64 (4H, s).<br>ESI-MS: m/z = 339 (M − OH)$^+$ |

(Intermediate 8)

As Intermediate 8,3-(1-hydroxycyclohexyl)-1-(p-tolyl)-2-propyn-1-one:

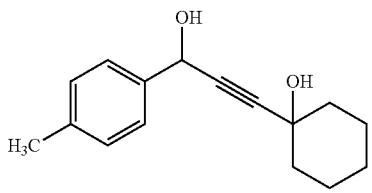 [SMILES: Cc1ccc(C(O)C#CC2(O)CCCCC2)cc1]

was synthesized by the following procedure.

Manganese dioxide (1.15 g, 13.2 mmol) was added to a solution of 1-(3-hydroxy-3-(p-tolyl)propyn-1-yl)cyclohexanol (Intermediate 2) (593 mg, 2.42 mmol) in dichloromethane (20 mL), and the resulting mixture was stirred at room temperature for 5 hours. The reaction solution was filtered through Celite, and the filtrate was concentrated under reduced pressure. The residue was purified by flash chromatography (silica gel, n-hexane/ethyl acetate) to obtain Intermediate 8 (534 mg, 2.20 mmol, 91%) as a pale yellow oily product.

$^1$H-NMR (400 MHz, CDCl$_3$) δ: 1.28-1.39 (1H, m), 1.55-1.84 (7H, m), 2.02-2.11 (2H, m), 2.23 (1H, brs), 2.43 (3H, s), 7.28 (2H, d, J=8.0 Hz), 8.02 (2H, d, J=8.0 Hz).

(Intermediate 9)

As Intermediate 9,3-(8-hydroxy-1,4-dioxaspiro[4.5]decan-8-yl)-1-(p-tolyl)-2-propyn-1-one:

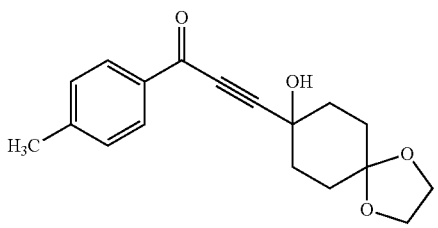 [SMILES: Cc1ccc(C(=O)C#CC2(O)CCC3(CC2)OCCO3)cc1]

was synthesized by the following procedure.

Manganese dioxide (29.6 g, 289 mmol) was added to a solution of 8-(3-hydroxy-3-(p-tolyl)propyn-1-yl)-1,4-dioxaspiro[4.5]decan-8-ol (Intermediate 3) (17.5 g, 57.9 mmol) in dichloromethane (289 mL), and the resulting mixture was stirred at room temperature for 15 hours. The reaction solution was filtered through Celite, and the filtrate was concentrated under reduced pressure. The residue was purified by flash chromatography (silica gel, n-hexane/ethyl acetate) to obtain Intermediate 9 (14.3 g, 47.6 mmol, 82%) as an oily product.

$^1$H-NMR (400 MHz, CDCl$_3$) δ: 1.79-1.85 (2H, m), 1.87-1.93 (2H, m), 2.04-2.15 (4H, m), 2.20 (1H, s), 2.43 (3H, s), 3.97 (4H, s), 7.28 (2H, d, J=8.0 Hz), 8.00 (2H, d, J=8.0 Hz).

ESI-MS: m/z=284 (M−OH)$^+$ (Intermediate 10)

As Intermediate 10, 3-(8-hydroxy-1,4-dioxaspiro[4.5]decan-8-yl)-1-(6-methylpyridin-3-yl)-2-propyn-1-one:

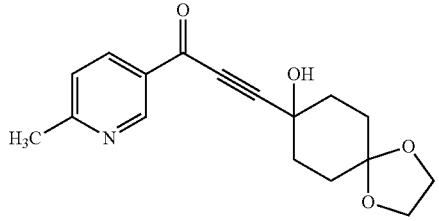 [SMILES: Cc1ccc(C(=O)C#CC2(O)CCC3(CC2)OCCO3)cn1]

was synthesized by the following procedure.

To a solution of 8-ethinyl-1,4-dioxaspiro[4.5]decan-8-ol (Intermediate 1) (592 mg, 3.25 mmol) in tetrahydrofuran (6 mL), 2.63 M n-butyllithium (a solution in n-hexane, 2.6 mL, 6.82 mmol) was added dropwise at −78° C. for 5 minutes, and the resulting mixture was stirred at the same temperature for 30 minutes. Then, a solution of N-methoxy-N-methyl-6-methylnicotinamide (614.5 mg, 3.41 mmol) in tetrahydrofuran (5 ml) was added dropwise thereto at −78° C. for 20 minutes, and the resulting mixture was stirred at the same temperature for 30 minutes. The reaction solution was allowed to warm to room temperature, and thereafter poured into a saturated aqueous ammonium chloride solution. The reaction solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 10 (626.3 mg, 2.08 mmol, 65%) as a pale yellow solid.

$^1$H-NMR (400 MHz, CDCl$_3$) δ: 1.76-1.83 (2H, m), 1.87-1.94 (2H, m), 2.04-2.10 (2H, m), 2.12-2.19 (2H, m), 2.30 (1H, s), 2.66 (3H, s), 3.97 (4H, s), 7.29 (1H, d, J=8.0 Hz), 8.22 (1H, dd, J=2.4, 8.0 Hz), 9.21 (1H, d, J=2.4 Hz).

ESI-MS: m/z=284 (M−OH)$^+$ (Intermediate 11)

As Intermediate 11, 3-(8-hydroxy-1,4-dioxaspiro[4.5]decan-8-yl)-1-(4-methoxyphenyl)-2-propyn-1-one:

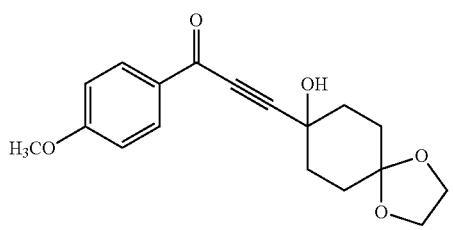 [SMILES: COc1ccc(C(=O)C#CC2(O)CCC3(CC2)OCCO3)cc1]

was synthesized by the following procedure.

Manganese dioxide (9.69 g, 112 mmol) was added to a solution of 8-(3-hydroxy-3-(4-methoxyphenyl)propyn-1-yl)-1,4-dioxaspiro[4.5]decan-8-ol (Intermediate 4) (7.10 g, 22.3 mmol) in dichloromethane (100 mL), and the resulting mixture was stirred at room temperature for 18 hours. The reaction solution was filtered through Celite, and the filtrate was concentrated under reduced pressure. The residue was purified by flash chromatography (silica gel, n-hexane/ethyl acetate) to obtain Intermediate 11 (5.45 g, 17.2 mmol, 77%) as an oily product.

$^1$H-NMR (400 MHz, CDCl$_3$) δ: 1.78-1.93 (4H, m), 2.03-2.17 (4H, m), 2.27 (1H, s), 3.89 (3H, s), 3.97 (4H, s), 6.95 (2H, d, J=9.0 Hz), 8.08 (2H, d, J=9.0 Hz).

ESI-MS: m/z=299 (M−OH)$^+$ (Intermediate 12)

As Intermediate 12, 1-(4-chlorophenyl)-3-(8-hydroxy-1,4-dioxaspiro[4.5]decan-8-yl)-2-propyn-1-one:

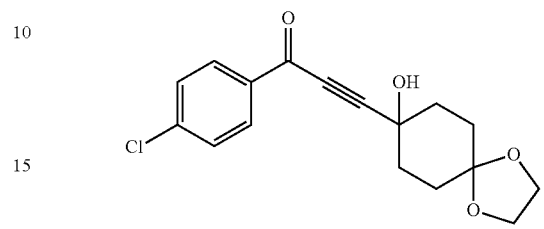

was synthesized by the following procedure.

Manganese dioxide (10.4 g, 119 mmol) was added to a solution of 8-(3-(4-chlorophenyl)-3-hydroxypropyn-1-yl)-1,4-dioxaspiro[4.5]decan-8-ol (Intermediate 5) (7.70 g, 23.9 mmol) in dichloromethane (120 mL), and the resulting mixture was stirred at room temperature for 18 hours. The reaction solution was filtered through Celite, and the filtrate was concentrated under reduced pressure. The residue was purified by flash chromatography (silica gel, n-hexane/ethyl acetate) to obtain Intermediate 12 (5.45 g, 17.0 mmol, 71%) as an oily product.

$^1$H-NMR (400 MHz, CDCl$_3$) δ: 1.77-1.94 (4H, m), 2.04-2.19 (4H, m), 2.15 (1H, s), 3.98 (4H, s), 7.47 (2H, d, J=8.5 Hz), 8.04 (2H, d, J=8.5 Hz).

ESI-MS: m/z=303 (M−OH)$^+$

The following compounds were synthesized in the same manner as in the synthesis of the above-described Intermediates 8 to 12.

TABLE 11

| Intermediate | Structural Formula | Compound Data |
|---|---|---|
| 13 | 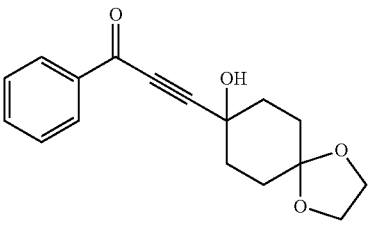 [SMILES: O=C(C#CC1(O)CCC2(CC1)OCCO2)c1ccccc1] | $^1$H-NMR (400 MHz, CDCl$_3$) δ: 1.78-1.94 (4H, m), 2.04-2.20 (4H, m), 2.33 (1H, s), 3.97 (4H, s), 7.49 (2H, t, J = 7.2 Hz), 7.62 (1H, t, J = 7.2 Hz), 7.69 (2H, d, J = 7.2 Hz). ESI-MS: m/z = 269 (M − OH)$^+$ |
| 14 | 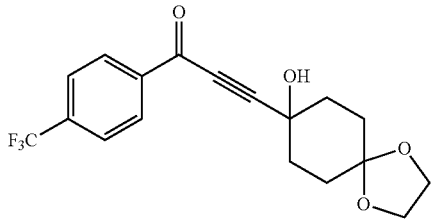 [SMILES: O=C(C#CC1(O)CCC2(CC1)OCCO2)c1ccc(C(F)(F)F)cc1] | $^1$H-NMR (400 MHz, CDCl3) δ: 1.81-1.84 (2H, m), 1.89-1.94 (2H, m), 2.09-2.17 (4H, m), 2.38 (1H, s), 3.98 (4H, s), 7.76 (2H, d, J = 8.0 Hz), 8.21 (2H, d, J = 8.0 Hz). |
| 15 | 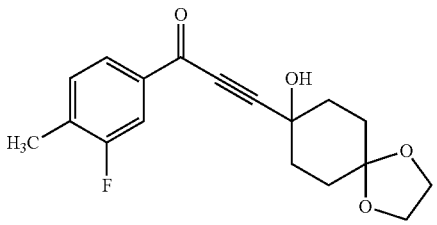 [SMILES: Cc1ccc(C(=O)C#CC2(O)CCC3(CC2)OCCO3)cc1F] | $^1$H-NMR (400 MHz, CDCl3) δ: 1.76-1.95 (4H, m), 2.04-2.20 (5H, m), 2.36 (3H, d, J = 2.0 Hz), 3.97 (4H, s), 7.31 (1H, t, J = 8.0 Hz), 7.71 (1H, d, J = 10.0 Hz), 7.81 (1H, d, J = 8.0 Hz). ESI-MS: m/z = 319 (M + H)$^+$ |

TABLE 11-continued

| Intermediate | Structural Formula | Compound Data |
| --- | --- | --- |
| 16 | | $^1$H-NMR (400 MHz, CDCl3) δ: 1.75-1.96 (4H, m), 2.03-2.25 (4H, m), 2.47-2.60 (1H, m), 3.98 (4H, s), 7.77-7.82 (2H, m), 8.16-8.23 (2H, m). ESI-MS: m/z = 312 (M + H)$^+$ |
| 17 | | $^1$H-NMR (400 MHz, CDCl3) δ: 1.26 (3H, t, J = 7.6 Hz), 1.78-1.94 (4H, m), 2.03-2.19 (4H, m), 2.27 (1H, br), 2.72 (2H, q, J = 7.6 Hz), 3.98 (4H, s), 7.30 (2H, d, J = 8.4 Hz), 8.03 (2H, d, J = 8.4 Hz). ESI-MS: m/z = 315 (M + H)$^+$ |

(Intermediate 18)

As Intermediate 18, 8-(1-(4-methoxyphenyl)-5-(p-tolyl)-1H-pyrazol-3-yl)-1,4-dioxaspiro[4.5]decan-8-ol:

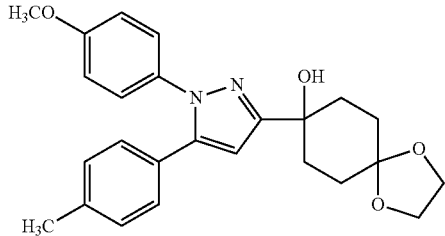

was synthesized by the following procedure.

Triethylamine (5.87 mL, 42.1 mmol) was added dropwise to a solution of 4-methoxyphenylhydrazine hydrochloride (7.35 g, 42.1 mmol) in ethanol (76.6 mL), and the resulting mixture was stirred at room temperature for 30 minutes. To the reaction solution, a solution of 3-(8-hydroxy-1,4-dioxaspiro[4.5]decan-8-yl)-1-(p-tolyl)-2-propyn-1-one (Intermediate 9) (11.5 g, 38.3 mmol) in ethanol (76.6 mL) was added dropwise, and the resulting mixture was stirred at room temperature for 15 hours. Thereafter, the reaction solution was concentrated under reduced pressure. Water was added to the residue, and the resulting solution was extracted with ethyl acetate. The organic layer was washed with 1 M hydrochloric acid, distilled water and brine, and then dried over anhydrous magnesium sulfate, and concentrated under reduced pressure. The residue was purified by flash chromatography (silica gel, n-hexane/ethyl acetate) to obtain Intermediate 18 (14.7 g, 35.0 mmol, 91%) as an amorphous product.

$^1$H-NMR (400 MHz, CDCl$_3$) δ: 1.71-1.74 (2H, m), 1.99-2.25 (6H, m), 2.33 (3H, s), 2.71 (1H, s), 3.81 (3H, s), 3.96-4.01 (4H, m), 6.39 (1H, s), 6.84 (2H, d, J=8.0 Hz), 7.09 (4H, s), 7.21 (2H, d, J=8.0 Hz).

ESI-MS: m/z=421 (M+H)$^+$ (Intermediate 19)

As Intermediate 19, 8-(1-(4-methoxyphenyl)-5-(6-methylpyridin-3-yl)-1H-pyrazol-3-yl)-1,4-dioxaspiro[4.5]decan-8-ol:

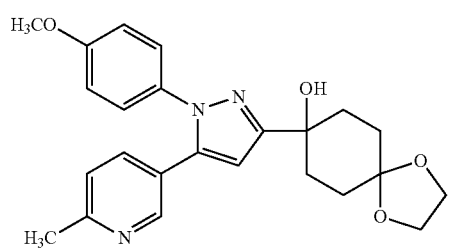

was synthesized by the following procedure.

Triethylamine (286 µL, 2.06 mmol) was added dropwise to a solution of 4-methoxyphenylhydrazine hydrochloride (359 mg, 2.06 mmol) in ethanol (4 mL), and the resulting mixture was stirred at room temperature for 30 minutes. To the reaction solution, a solution of 3-(8-hydroxy-1,4-dioxaspiro[4.5]decan-8-yl)-1-(6-methylpyridin-3-yl)-2-propyn-1-one (Intermediate 10) (563.7 mg, 1.87 mmol) in ethanol (5.4 mL) was added dropwise, and the resulting mixture was stirred at room temperature for 22 hours. Thereafter, the reaction solution was concentrated under reduced pressure. Water was added to the residue, and the resulting solution was extracted with ethyl acetate. The organic layer was washed with distilled water and brine, and then dried over anhydrous magnesium sulfate, and concentrated under reduced pressure. The residue was purified by flash chromatography (silica gel, n-hexane/ethyl acetate) to obtain Intermediate 19 (177 mg, 0.42 mmol, 22%) as an amorphous product.

$^1$H-NMR (400 MHz, CDCl$_3$) δ: 1.72-1.75 (2H, m), 2.00-2.03 (2H, m), 2.07-2.14 (2H, m), 2.19-2.26 (2H, m), 2.55 (3H, s), 2.65 (1H, s), 3.81 (3H, s), 3.96-4.03 (4H, m), 6.47 (1H, s), 6.86 (2H, d, J=8.8 Hz), 7.06 (1H, d, J=8.0 Hz), 7.20 (2H, d, J=8.8 Hz), 7.33 (1H, dd, J=2.2, 8.0 Hz), 8.40 (1H, d, J=2.2 Hz).

ESI-MS: m/z=422 (M+H)$^+$ (Intermediate 20)

As Intermediate 20, 8-(1,5-bis(4-methoxyphenyl)-1H-pyrazol-3-yl)-1,4-dioxaspiro[4.5]decan-8-ol:

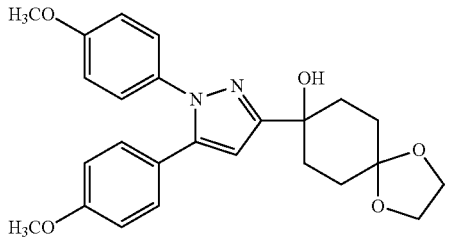 [SMILES: COc1ccc(-c2cc(C3(O)CCC4(CC3)OCCO4)nn2-c2ccc(C)cc2)cc1]

was synthesized by the following procedure.

A solution of 4-methoxyphenylhydrazine hydrochloride (470 mg, 2.69 mmol) and triethylamine (0.74 mL, 5.41 mmol) in ethanol (4.5 mL) was added to a solution of 3-(8-hydroxy-1,4-dioxaspiro[4.5]decan-8-yl)-1-(4-methoxyphenyl)-2-propyn-1-one (Intermediate 11) (700 mg, 2.24 mmol) in ethanol (4.5 mL), and the resulting mixture was stirred at room temperature for 20 hours. The reaction solution was concentrated under reduced pressure, and distilled water was added to the residue, followed by extraction of the resulting mixture with ethyl acetate. The organic layer was dried over anhydrous magnesium sulfate, and concentrated under reduced pressure. The residue was purified by flash chromatography (silica gel, n-hexane/ethyl acetate) to obtain Intermediate 20 (864 mg, 1.98 mmol, 88%) as a white amorphous product.

$^1$H-NMR (400 MHz, CDCl$_3$) δ: 1.68-1.77 (2H, m), 1.96-2.26 (6H, m), 2.70 (1H, brs), 3.80 (3H, s), 3.81 (3H, s), 3.94-4.04 (4H, m), 6.37 (1H, s), 6.81 (2H, d, J=8.8 Hz), 6.85 (2H, d, J=8.8 Hz), 7.13 (2H, d, J=8.8 Hz), 7.21 (2H, d, J=8.8 Hz).

ESI-MS: m/z=437 (M+H)$^+$ (Intermediate 21)

As Intermediate 21, 8-(5-(4-chlorophenyl)-1-(4-methoxyphenyl)-1H-pyrazol-3-yl)-1,4-dioxaspiro[4.5]decan-8-ol:

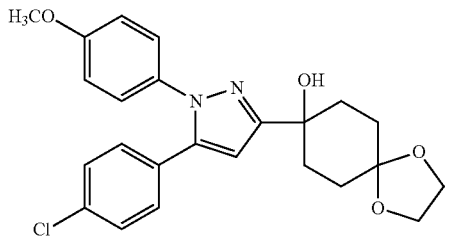 [SMILES: COc1ccc(-n2nc(C3(O)CCC4(CC3)OCCO4)cc2-c2ccc(C#N)cc2)cc1]

was synthesized by the following procedure.

Triethylamine (0.730 mL, 5.24 mmol) was added dropwise to a solution of 4-methoxyphenylhydrazine hydrochloride (457 mg, 2.62 mmol) in ethanol (4.4 mL), and the resulting mixture was stirred at room temperature for 30 minutes. To the reaction solution, a solution of 1-(4-chlorophenyl)-3-(8-hydroxy-1,4-dioxaspiro[4.5]decan-8-yl)-2-propyn-1-one (Intermediate 12) (700 mg, 2.18 mmol) in ethanol (4.4 mL) was added dropwise, and the resulting mixture was stirred at room temperature for 14 hours. Thereafter, the reaction solution was concentrated under reduced pressure. Water was added to the residue, and the resulting solution was extracted with ethyl acetate. The organic layer was washed with 1 M hydrochloric acid, distilled water and brine, and then dried over anhydrous magnesium sulfate, and concentrated under reduced pressure. The residue was purified by flash chromatography (silica gel, n-hexane/ethyl acetate) to obtain Intermediate 21 (756 mg, 1.71 mmol, 79%) as an amorphous product.

$^1$H-NMR (400 MHz, CDCl$_3$) δ: 1.69-1.76 (2H, m), 1.97-2.25 (6H, m), 2.66 (1H, brs), 3.82 (3H, s), 3.94-4.03 (4H, m), 6.43 (1H, s), 6.85-6.87 (2H, m), 7.13 (2H, d, J=8.4 Hz), 7.19 (2H, d, J=8.4 Hz), 7.25-7.27 (2H, m).

ESI-MS: m/z=441 (M+H)$^+$ (Intermediate 22)

As Intermediate 22, 8-(1-(4-chlorophenyl)-5-(p-tolyl)-1H-pyrazol-3-yl)-1,4-dioxaspiro[4.5]decan-8-ol:

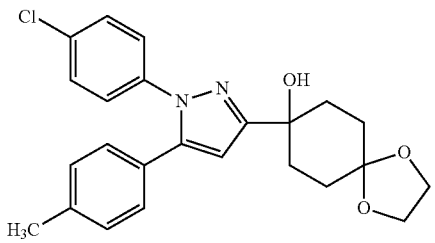

was synthesized by the following procedure.

Triethylamine (5.87 mL, 42.1 mmol) was added dropwise to a solution of 4-chlorophenylhydrazine hydrochloride (418 mg, 2.33 mmol) in ethanol (4.8 mL), and the resulting mixture was stirred at room temperature for 30 minutes. To the reaction solution, a solution of 3-(8-hydroxy-1,4-dioxaspiro[4.5]decan-8-yl)-1-(p-tolyl)-2-propyn-1-one (Intermediate 9) (698 mg, 2.32 mmol) in ethanol (4.7 mL) was added dropwise, and the resulting mixture was stirred at room temperature for 14 hours. Thereafter, the reaction solution was concentrated under reduced pressure. Water was added to the residue, and the resulting solution was extracted with ethyl acetate. The organic layer was washed with distilled water and brine, and then dried over anhydrous sodium sulfate, and concentrated under reduced pressure. The residue was purified by flash chromatography (silica gel, n-hexane/ethyl acetate) to obtain Intermediate 22 (948 mg, 2.23 mmol, yield: 96%) as an amorphous product.

$^1$H-NMR (400 MHz, CDCl$_3$) δ: 1.71-1.75 (2H, m), 1.98-2.14 (4H, m), 2.17-2.25 (2H, m), 2.36 (3H, s), 2.62 (1H, s), 3.96-4.03 (4H, m), 6.41 (1H, s), 7.09 (2H, d, J=8.0 Hz), 7.13 (2H, d, J=8.0 Hz), 7.22-7.30 (4H, m).

ESI-MS: m/z=407 (M−OH)$^+$

The following compounds were synthesized in the same manner as in the above-described Intermediates 18 to 22.

TABLE 12

| Intermediate | Structural Formula | Compound Data |
| --- | --- | --- |
| 23 | ![structure] | $^1$H-NMR (400 MHz, CDCl$_3$) δ: 1.69-1.76 (2H, m), 2.16-2.25 (2H, m), 1.96-2.23 (4H, m), 2.63 (1H, s), 3.94-4.03 (4H, m), 6.45 (1H, s), 7.14 (2H, d, J = 8.4 Hz), 7.21 (2H, d, J = 8.4 Hz), 7.29-7.32 (4H, m). ESI-MS: m/z = 445 (M + H)$^+$ |

TABLE 12-continued

| Intermediate | Structural Formula | Compound Data |
| --- | --- | --- |
| 24 | | $^1$H-NMR (400 MHz, CDCl$_3$) δ: 1.70-1.76 (2H, m), 1.98-2.14 (4H, m), 2.18-2.25 (2H, m), 2.68 (1H, s), 3.95-4.02 (4H, m), 6.45 (1H, s), 7.13-7.15 (2H, m), 7.25-7.37 (7H, m).<br>ESI-MS: m/z = 411 (M + H)$^+$ |
| 25 | | $^1$H-NMR (400 MHz, CDCl$_3$) δ: 1.70-1.76 (2H, m), 1.98-2.04 (2H, m), 2.07-2.14 (2H, m), 2.18-2.25 (2H, m), 2.34 (3H, s), 2.35 (3H, s), 2.70 (1H, s), 3.95-4.02 (4H, m), 6.40 (1H, s), 7.08-7.11 (4H, m), 7.12 (2H, d, J = 8.4 Hz), 7.17 (2H, d, J = 8.4 Hz).<br>ESI-MS: m/z = 387 (M − OH)$^+$ |
| 26 | | $^1$H-NMR (400 MHz, CDCl$_3$) δ: 1.71-1.77 (2H, m), 1.98-2.05 (2H, m), 2.07-2.14 (2H, m), 2.18-2.26 (2H, m), 2.34 (3H, s), 2.69 (1H, s), 3.96-4.03 (4H, m), 6.42 (1H, s), 7.09-7.11 (4H, m), 7.26-7.35 (5H, m).<br>ESI-MS: m/z = 373 (M − OH)$^+$ |
| 27 | | $^1$H-NMR (400 MHz, CDCl3) δ: 1.60 (2H, m), 1.73 (2H, d, J = 12.4 Hz), 2.10 (2H, d, J = 3.4, 12.8 Hz), 2.22 (2H, td, J = 3.9, 12.4 Hz), 3.80 (3H, s), 3.96-4.03 (4H, m), 6.44 (1H, s), 6.83-6.85 (2H, m), 7.18-7.22 (4H, m), 7.26-7.30 (3H, m). |
| 28 | | $^1$H-NMR (400 MHz, CDCl3) δ: 1.73 (2H, d, J = 12.0 Hz), 2.01 (2H, d, J = 12.4 Hz), 2.10 (2H, td, J = 3.2 Hz), 2.22 (2H, td, J = 3.2, 12.4 Hz), 2.24 (3H, s), 3.96-4.03 (4H, m), 6.44 (1H, s), 7.12 (2H, d, J = 8.4 Hz), 7.16 (2H, d, J = 8.8 Hz), 7.21-7.23 (2H, m), 7.27-7.30 (3H, m).<br>ESI-MS: m/z = 391 (M + H)$^+$ |
| 29 | | $^1$H-NMR (400 MHz, CDCl3) δ: 1.73 (2H, d, J = 12.4 Hz), 1.99 (2H, d, J = 12.4 Hz), 2.10 (2H, td, J = 3.2, 12.4 Hz), 2.21 (2H, td, J = 3.6, 12.4 Hz), 2.25 (3H, s), 2.73 (1H, s), 3.80 (3H, s), 3.96-4.03 (4H, m), 6.37 (1H, s), 6.82 (2H, m), 7.09-7.18 (6H, m).<br>ESI-MS: m/z = 421 (M + H)$^+$ |

TABLE 12-continued

| Intermediate | Structural Formula | Compound Data |
| --- | --- | --- |
| 30 | | $^1$H-NMR (400 MHz, CDCl3) δ: 1.73 (2H, d, J = 12.4 Hz), 2.01 (2H, d, J = 12.4 Hz), 2.10 (2H, td, J = 3.2, 12.8 Hz), 2.21 (2H, td, J = 3.2, 12.4 Hz), 2.64 (1H, s), 3.82 (3H, s), 3.95-4.03 (4H, m), 6.40 (1H, s), 6.84 (2H, d, J = 8.4 Hz), 7.12 (2H, d, J = 8.8 Hz), 7.23 (2H, d, J = 8.8 Hz), 7.28 (2H, d, J = 8.8 Hz).<br>ESI-MS: m/z = 441 (M + H)⁺ |
| 31 | | $^1$H-NMR (400 MHz, CDCl3) δ: 1.70 (2H, d, J = 12.0 Hz), 2.01 (2H, d, J = 8.8 Hz), 2.10 (2H, td, J = 4.0, 12.8 Hz), 2.21 (2H, td, J = 3.6, 12.4 Hz), 2.71 (1H, s), 3.80 (3H, s), 3.92-4.03 (4H, m), 6.39 (1H, s), 6.81 (2H, d, J = 12.0 Hz), 7.13 (2H, d, J = 12.0 Hz), 7.22-7.35 (5H, m). |
| 32 | | $^1$H-NMR (400 MHz, CDCl3) δ: 1.71-1.74 (4H, m), 1.96-2.16 (4H, m), 2.87 (1H, s), 3.81 (3H, s), 3.94-4.01 (4H, m), 6.52 (1H, s), 6.86 (2H, d, J = 8.0 Hz), 7.19 (2H, d, J = 8.0 Hz), 7.32 (2H, d, J = 8.0 Hz), 7.54 (2H, d, J = 8.0 Hz). |
| 33 | | $^1$H-NMR (400 MHz, CDCl3) δ: 1.23 (3H, t, J = 7.6 Hz), 1.69-1.76 (2H, m), 1.98-2.26 (6H, m), 2.63 (2H, q, J = 7.6 Hz), 2.69 (1H, br), 3.81 (3H, s), 3.95-4.03 (4H, m), 6.40 (1H, s), 6.82-6.87 (2H, m), 7.12 (4H, s), 7.19-7.24 (2H, m).<br>ESI-MS: m/z = 425 (M + H)⁺ |
| 34 | | $^1$H-NMR (400 MHz, CDCl$_3$) δ: 1.68-1.77 (2H, m), 1.97-2.25 (6H, m), 2.35 (3H, s), 2.64 (1H, s), 3.89 (3H, s), 3.94-4.03 (4H, m), 6.40 (1H, s), 6.87 (1H, t, J = 8.8 Hz), 6.94-7.01 (1H, m), 7.07-7.13 (5H, m).<br>ESI-MS: m/z = 425 (M + H)⁺ |
| 35 | | $^1$H-NMR (400 MHz, CDCl$_3$) δ: 1.69-1.77 (2H, m), 1.97-2.28 (9H, m), 2.64 (1H, s), 3.82 (3H, s), 3.95-4.03 (4H, m), 6.41 (1H, s), 6.83-6.89 (4H, m), 7.08 (1H, t, J = 8.0 Hz), 7.18-7.27 (2H, m).<br>ESI-MS: m/z = 439 (M + H)⁺ |

TABLE 12-continued

| Intermediate | Structural Formula | Compound Data |
|---|---|---|
| 36 | | $^1$H-NMR (400 MHz, CDCl$_3$) δ: 1.70-1.78 (2H, m), 1.97-2.27 (6H, m), 2.38 (3H, s), 2.54 (1H, s), 3.94-4.03 (4H, m), 6.45 (1H, s), 7.09-7.20 (4H, m), 7.40-7.44 (2H, m), 7.57-7.62 (2H, m). ESI-MS: m/z = 416 (M + H)$^+$ |
| 37 | | $^1$H-NMR (400 MHz, CDCl$_3$) δ: 1.69-1.76 (2H, m), 1.97-2.26 (6H, m), 2.56 (1H, br), 3.83 (3H, s), 3.94-4.03 (4H, m), 6.52 (1H, s), 6.84-6.90 (2H, m), 7.14-7.20 (2H, m), 7.29-7.33 (2H, m), 7.55-7.59 (2H, m). ESI-MS: m/z = 432 (M + H)$^+$ |

(Intermediate 38)

As Intermediate 38, 1-(1-(4-methoxyphenyl)-5-(p-tolyl)-1H-pyrazol-3-yl)-cyclohexan-cis-1,4-diyl diacetate:

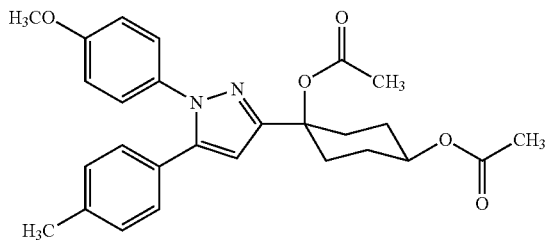 [SMILES: COc1ccc(-n2nc(C3(OC(C)=O)CCC(OC(C)=O)CC3)cc2-c2ccc(C)cc2)cc1]

was synthesized by the following procedure.

Acetic anhydride (0.187 mL, 1.98 mmol), pyridine (0.192 mL, 2.38 mmol), and 4-dimethylaminopyridine (48.4 mg, 0.396 mmol) were added to a suspension of 1-(1-(4-methoxyphenyl)-5-(p-tolyl)-1H-pyrazol-3-yl)cyclohexan-cis-1,4-diol (Compound 3) (300 mg, 0.793 mmol) in dichloromethane (2.6 mL), and the resulting mixture was stirred at room temperature for 60 hours. Again, 4-dimethylaminopyridine (48.4 mg, 0.396 mmol) was added thereto, and the resulting mixture was stirred at room temperature for an additional 6 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 38 (297 mg, 0.642 mmol, 81%) as a white solid.

$^1$H-NMR (400 MHz, CDCl$_3$) δ: 1.74-1.82 (2H, m), 1.92-1.98 (2H, m), 2.01-2.08 (5H, m), 2.10 (3H, s), 2.32 (3H, s), 2.70-2.77 (2H, m), 3.80 (3H, s), 4.80-4.89 (1H, m), 6.38 (1H, s), 6.83 (2H, d, J=8.8 Hz), 7.08 (4H, s), 7.20 (2H, d, J=8.8 Hz).

ESI-MS: m/z=463 (M+H)$^+$ (Intermediate 39)

As Intermediate 39, c-4-methoxy-1-(1-(4-methoxyphenyl)-5-(p-tolyl)-1H-pyrazol-3-yl)-cyclohexan-r-1-yl acetate:

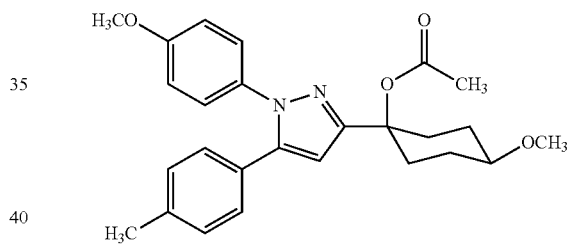

was synthesized by the following procedure.

To a solution of c-4-hydroxy-1-(1-(4-methoxyphenyl)-5-(p-tolyl)-1H-pyrazol-3-yl)-cyclohexan-r-1-yl acetate (Intermediate 84) (0.150 g, 0.357 mmol) in N,N-dimethylformamide (1.8 mL), 55% sodium hydride (23.4 mg, 0.535 mmol) and methyl iodide (29.0 μL, 0.464 mmol) were added with stirring under ice-cooling, and the resulting mixture was stirred at room temperature for 9 hours. Water was added to the reaction solution with stirring under ice-cooling to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 39 (124 mg, 0.284 mmol, 80%) as a white solid.

$^1$H-NMR (400 MHz, CDCl$_3$) δ: 1.60-1.68 (2H, m), 1.94-2.03 (4H, m), 2.08 (3H, s), 2.32 (3H, s), 2.69-2.76 (2H, m), 3.24-3.33 (1H, m), 3.39 (3H, s), 3.80 (3H, s), 6.37 (1H, s), 6.83 (2H, d, J=8.8 Hz), 7.08 (4H, s), 7.20 (2H, d, J=8.8 Hz).

ESI-MS: m/z=435 (M+H)$^+$ (Intermediate 40)

As Intermediate 40, 4-(4-fluoro-1-(4-methoxyphenyl)-5-(p-tolyl)-1H-pyrazol-3-yl)-c-4-hydroxy-cyclohexan-r-1-yl acetate:

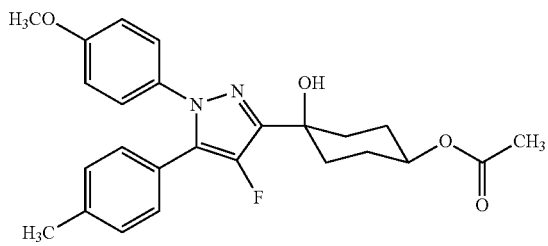

was synthesized by the following procedure.

Selectfluor™ (120 mg, 0.340 mmol) was added to a solution of c-4-hydroxy-4-(1-(4-methoxyphenyl)-5-(p-tolyl)-1H-pyrazol-3-yl)-cyclohexan-r-1-yl acetate (Compound 12) (130 mg, 0.309 mmol) in acetonitrile (3.09 mL), and the resulting mixture was stirred at room temperature for 3 hours. A saturated aqueous sodium thiosulfate solution was added to the reaction solution, and the resulting solution was extracted with ethyl acetate. The organic layer was washed with brine, and then dried over anhydrous magnesium sulfate, and concentrated under reduced pressure. The residue was purified by flash chromatography (silica gel, n-hexane/ethyl acetate) to obtain Intermediate 40 (61 mg, 0.140 mmol, 45%) as a pale yellow amorphous product.

$^1$H-NMR (400 MHz, CDCl$_3$) δ: 1.89-2.15 (11H, m), 2.35 (3H, m), 2.73 (1H, s), 3.81 (3H, s), 4.82-4.89 (1H, m), 6.84-6.86 (2H, m), 7.10-7.18 (6H, m).

ESI-MS: m/z=439 (M+H)$^+$ (Intermediate 41)

As Intermediate 41, 1-(1-(4-methoxyphenyl)-5-(p-tolyl)-1H-pyrazol-3-yl)-4-oxo-cyclohexan-1-yl acetate:

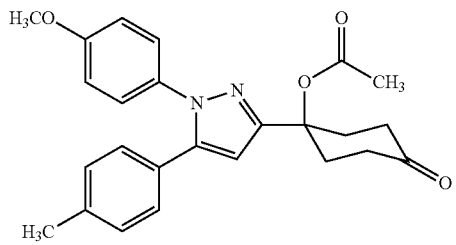 [SMILES: COc1ccc(-n2nc(C3(OC(C)=O)CCC(=O)CC3)cc2-c2ccc(C)cc2)cc1]

was synthesized by the following procedure.

Dess-Martin reagent (172 mg, 0.405 mmol) was added to a solution of c-4-hydroxy-1-(1-(4-methoxyphenyl)-5-(p-tolyl)-1H-pyrazol-3-yl)-cyclohexan-r-1-yl acetate (Intermediate 84) (142 mg, 0.338 mmol) in dichloromethane (3.38 mL), and the resulting mixture was stirred at 0° C. for 2 hours. The reaction solution was filtered through Celite, and the residue was purified by flash chromatography (silica gel, n-hexane/ethyl acetate) to obtain Intermediate 41 (120 mg, 0.287 mmol, 85%) as a white amorphous product.

$^1$H-NMR (400 MHz, CDCl$_3$) δ: 2.13 (3H, s), 2.33 (3H, s), 2.44-2.52 (4H, m), 2.59-2.65 (2H, m), 2.93-2.96 (2H, m), 3.81 (3H, s), 6.45 (1H, s), 6.84 (2H, d, J=8.8 Hz), 7.08 (4H, s), 7.20 (2H, d, J=8.8 Hz).

ESI-MS: m/z=419 (M+H)$^+$ (Intermediate 42)

As Intermediate 42, c-4-hydroxy-4-(1-(4-methoxyphenyl)-5-(p-tolyl)-1H-pyrazol-3-yl)-cis-cyclohexan-r-1-carbaldehyde:

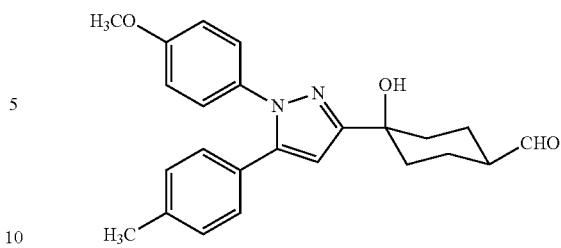

was synthesized by the following procedure.

To a solution of (methoxymethyl)triphenylphosphonium chloride (546.3 mg, 1.59 mmol) in tetrahydrofuran (1.3 mL), potassium tert-butoxide (178.7 mg, 1.59 mmol) was added at −40° C., and the resulting mixture was stirred at the same temperature for 60 minutes. A solution of 4-hydroxy-4-(1-(4-methoxyphenyl)-5-(p-tolyl)-1H-pyrazol-3-yl)cyclohexan-1-one (Compound 4) (200 mg, 0.53 mmol) in tetrahydrofuran (1.35 mL) was added dropwise to the reaction solution at −40° C., and thereafter the resulting mixture was stirred at room temperature for 1.5 hours. To the reaction solution, a 6 M aqueous hydrochloric acid solution was added at 0° C., and the resulting mixture was stirred for 12 hours. Distilled water was added to the reaction solution, and the resulting solution was extracted with ethyl acetate. The organic layer was washed with a saturated aqueous sodium hydrogen carbonate solution and brine, dried over anhydrous sodium sulfate, and concentrated under reduced pressure. The residue was purified by flash chromatography (silica gel, n-hexane/ethyl acetate) to obtain Intermediate 42 (87.5 mg, 0.23 mmol, 42%) as a colorless oily product.

$^1$H-NMR (400 MHz, CDCl$_3$) δ: 1.88-1.96 (6H, m), 2.09-2.11 (2H, m), 2.25-2.36 (5H, m), 3.80 (3H, s), 6.39 (1H, s), 6.84 (2H, d, J=8.8 Hz), 7.09-7.14 (4H, m), 7.20 (2H, d, J=8.8 Hz), 9.66 (1H, d, J=2.0 Hz).

ESI-MS: m/z=391 (M+H)$^+$ (Intermediate 43)

As Intermediate 43, ethyl 1,4-dioxaspiro[4.5]decan-8-carboxylate:

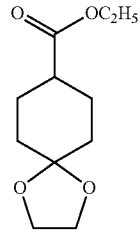 [SMILES: CCOC(=O)C1CCC2(CC1)OCCO2]

was synthesized by the following procedure.

Ethylene glycol (3.6 mL, 64.6 mmol) and p-toluenesulfonic acid monohydrate (1.12 g, 5.88 mmol) were added to a solution of ethyl 4-oxocyclohexanecarboxylate (10.0 g, 58.8 mmol) in toluene (196 mL), and the obtained solution was heated to reflux at 150° C. The resulting solution was stirred for 18 hours. To the reaction solution, a saturated sodium bicarbonate solution was added to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 43 (12.3 g, 57.4 mmol, 98%) as a colorless oily compound.

¹H-NMR (400 MHz, CDCl₃) δ: 1.25 (3H, t, J=7.2 Hz), 1.51-1.61 (2H, m), 1.75-1.86 (4H, m), 1.90-1.98 (2H, m), 2.29-2.38 (1H, s), 3.95 (4H, s), 4.13 (2H, q, J=7.2 Hz).

ESI-MS: m/z=215 (M+H)⁺

(Intermediate 44)

As Intermediate 44, ethyl 8-(benzyloxymethyl)-1,4-dioxaspiro[4.5]decan-8-carboxylate:

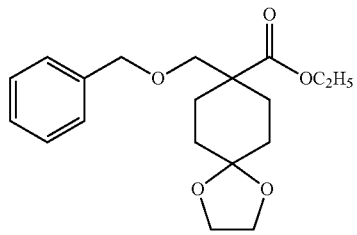 [SMILES: CCOC(=O)C1(COCc2ccccc2)CCC2(CC1)OCCO2]

was synthesized by the following procedure.

To a solution of ethyl 1,4-dioxaspiro[4.5]decan-8-carboxylate (Intermediate 43) (500 mg, 2.33 mmol) in tetrahydrofuran (7.8 mL), 0.5 M potassium bis(trimethylsilyl)amide (a solution in toluene, 4.67 mL, 2.33 mmol) was added at −78° C., and the resulting mixture was stirred for 20 minutes. Thereafter, benzylchloromethyl ether (0.379 mL, 2.45 mmol) was added thereto, and the resulting mixture was stirred at −78° C. for 30 minutes and at room temperature for 1.5 hours. A saturated aqueous ammonium chloride solution was added to the reaction solution, and the resulting solution was extracted with ethyl acetate. The organic layer was dried over anhydrous sodium sulfate, and concentrated under reduced pressure. To the residue, a 3 M aqueous sodium hydroxide solution (1.0 mL) was added, and the resulting mixture was stirred for 4 hours. The reaction solution was extracted with ether, and the organic layer was washed with brine, dried over anhydrous sodium sulfate, and concentrated under reduced pressure. The residue was purified by flash chromatography (silica gel, n-hexane/ethyl acetate) to obtain Intermediate 44 (279 mg, 0.834 mmol, 36%) as a colorless oily compound.

¹H-NMR (400 MHz, CDCl₃) δ: 1.24 (3H, t, J=7.2 Hz), 1.52-1.68 (6H, m), 2.16-2.23 (2H, m), 3.46 (2H, s), 3.88-3.96 (4H, m), 4.17 (2H, q, J=7.2 Hz), 4.49 (2H, s), 7.25-7.39 (5H, m).

ESI-MS: m/z=335 (M+H)⁺

(Intermediate 45)

As Intermediate 45, (8-(benzyloxymethyl)-1,4-dioxaspiro[4.5]decan-8-yl)methanol:

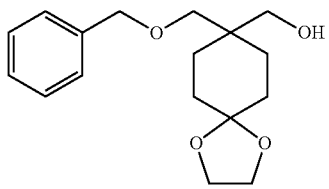 [SMILES: OCC1(COCc2ccccc2)CCC2(CC1)OCCO2]

was synthesized by the following procedure.

To a solution of ethyl 8-(benzyloxymethyl)-1,4-dioxaspiro[4.5]decan-8-carboxylate (Intermediate 44) (279 mg, 0.834 mmol) in tetrahydrofuran (4.2 mL), lithium borohydride (91.0 mg, 4.17 mmol) was added with stirring under ice-cooling, and the resulting mixture was stirred at 70° C. for 4 hours. A saturated aqueous ammonium chloride solution was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 45 (183 mg, 0.625 mmol, 75%) as a colorless oily compound.

¹H-NMR (400 MHz, CDCl₃) δ: 1.48-1.66 (8H, m), 2.76 (1H, t, J=6.0 Hz), 3.43 (2H, s), 3.60 (2H, d, J=6.0 Hz), 3.91-3.95 (4H, m), 4.52 (2H, s), 7.27-7.38 (5H, m).

ESI-MS: m/z=293 (M+H)⁺

(Intermediate 46)

As Intermediate 46, 8-(benzyloxymethyl)-1,4-dioxaspiro[4.5]decan-8-carboaldehyde:

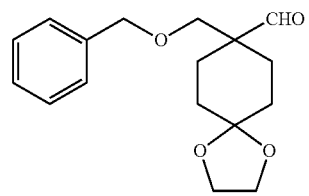 [SMILES: O=CC1(COCc2ccccc2)CCC2(CC1)OCCO2]

was synthesized by the following procedure.

To a solution of (8-(benzyloxymethyl)-1,4-dioxaspiro[4.5]decan-8-yl)methanol (Intermediate 45) (183 mg, 0.625 mmol) in DMSO (2.1 mL), 50% sulfur trioxide-pyridine complex (596 mg, 1.87 mmol) and triethylamine (0.522 mL, 3.75 mmol) were added, and the resulting mixture was stirred at room temperature for 20 minutes. Water was added to the reaction solution to stop the reaction, and the resulting solution was extracted with ethyl acetate. The organic layer was washed sequentially with a 20% aqueous citric acid solution, a saturated sodium bicarbonate solution and brine, dried over anhydrous sodium sulfate, and concentrated under reduced pressure. The residue was purified by flash chromatography (silica gel, n-hexane/ethyl acetate) to obtain Intermediate 46 (172 mg, 0.592 mmol, 95%) as a colorless oily compound.

¹H-NMR (400 MHz, CDCl₃) δ: 1.55-1.67 (6H, m), 2.03-2.11 (2H, m), 3.45 (2H, s), 3.90-3.95 (4H, m), 4.47 (2H, s), 7.25-7.36 (5H, m), 9.60 (1H, s).

ESI-MS: m/z=291 (M+H)⁺

(Intermediate 47)

As Intermediate 47, 8-(benzyloxymethyl)-8-ethinyl-1,4-dioxaspiro[4.5]decane:

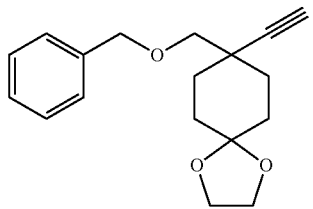 [SMILES: C#CC1(COCc2ccccc2)CCC2(CC1)OCCO2]

was synthesized by the following procedure.

To a solution of 8-(benzyloxymethyl)-1,4-dioxaspiro[4.5]decan-8-carboaldehyde (Intermediate 46) (100 mg, 0.344 mmol) in methanol (5.2 mL), potassium carbonate (143 mg, 1.03 mmol) and dimethyl-1-diazo-2-oxopropylphosphonate (165 mg, 0.861 mmol) were added with stifling under ice-cooling, and the resulting mixture was stirred at room temperature for 1 hour. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 47 (88.9 mg, 0.310 mmol, 90%) as a colorless oily compound.

¹H-NMR (400 MHz, CDCl₃) δ: 1.52-1.71 (4H, m), 1.77-1.85 (2H, m), 1.94-2.04 (2H, m), 2.19 (1H, s), 3.38 (2H, s), 3.89-3.99 (4H, s), 4.61 (2H, s), 7.25-7.37 (5H, m).

ESI-MS: m/z=287 (M+H)⁺

(Intermediate 48)

As Intermediate 48, 3-(8-(benzyloxymethyl)-1,4-dioxaspiro[4.5]decan-8-yl)-1-(p-tolyl)propyn-1-ol:

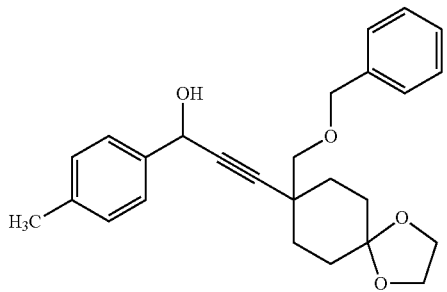 [SMILES: Cc1ccc(C(O)C#CC2(COCc3ccccc3)CCC3(CC2)OCCO3)cc1]

was synthesized by the following procedure.

To a solution of 8-(benzyloxymethyl)-8-ethinyl-1,4-dioxaspiro[4.5]decane (Intermediate 47) (393 mg, 1.37 mmol) in tetrahydrofuran (4.6 mL), 2.6 M n-butyllithium (a solution in hexane, 0.555 mL, 1.44 mmol) was added at −78° C., and the resulting mixture was stirred for 10 minutes. Further, 4-methylbenzaldehyde (0.178 mL, 1.51 mmol) was added thereto, and thereafter the resulting mixture was allowed to warm gradually to room temperature and stirred for 1 hour. A saturated aqueous ammonium chloride solution was added to the reaction solution, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 48 (459 mg, 1.13 mmol, 82%) as a colorless oily compound.

¹H-NMR (400 MHz, CDCl₃) δ: 1.62-1.71 (4H, m), 1.79-1.86 (2H, m), 1.92-2.02 (2H, m), 2.23 (1H, brs), 2.34 (3H, s), 3.41 (2H, s), 3.89-3.98 (4H, m), 4.59 (2H, m), 5.44 (1H, d, J=5.2 Hz), 7.15 (2H, d, J=8.0 Hz), 7.25-7.35 (5H, m), 7.43 (2H, d, J=8.0 Hz).

ESI-MS: m/z=407 (M+H)⁺

(Intermediate 49)

As Intermediate 49, 3-(8-(benzyloxymethyl)-1,4-dioxaspiro[4.5]decan-8-yl)-1-(p-tolyl)propyn-1-one:

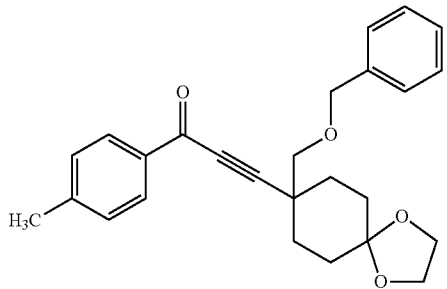 [SMILES: Cc1ccc(C(=O)C#CC2(COCc3ccccc3)CCC3(CC2)OCCO3)cc1]

was synthesized by the following procedure.

Manganese dioxide (625 mg, 7.19 mmol) was added to a solution of 3-(8-(benzyloxymethyl)-1,4-dioxaspiro[4.5]decan-8-yl)-1-(p-tolyl) propyn-1-ol (Intermediate 48) (585 mg, 1.44 mmol) in dichloromethane (7.2 mL), and the resulting mixture was stirred at room temperature for 13 hours. The reaction solution was filtered through Celite, and thereafter the filtrate was concentrated under reduced pressure. The residue was purified by flash chromatography (silica gel, n-hexane/ethyl acetate) to obtain Intermediate 49 (540 mg, 1.33 mmol, 93%) as a colorless oily compound.

¹H-NMR (400 MHz, CDCl₃) δ: 1.71-1.80 (4H, m), 1.97-2.03 (4H, m), 2.41 (3H, s), 3.52 (2H, s), 3.91-4.00 (4H, m), 4.63 (2H, m), 7.21 (2H, d, J=8.0 Hz), 7.25-7.38 (5H, m), 8.03 (2H, d, J=8.0 Hz).

ESI-MS: m/z=405 (M+H)⁺

(Intermediate 50)

As Intermediate 50, 3-(8-(benzyloxymethyl)-1,4-dioxaspiro[4.5]decan-8-yl)-1-(4-methoxyphenyl)-5-(p-tolyl)-1H-pyrazole:

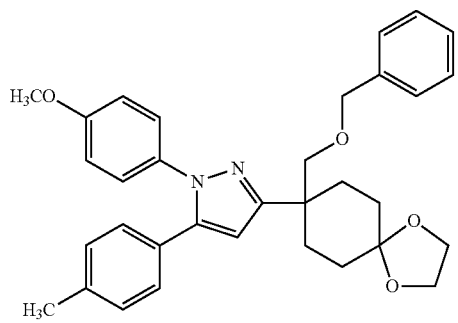 [SMILES: COc1ccc(-n2nc(C3(COCc4ccccc4)CCC4(CC3)OCCO4)cc2-c2ccc(C)cc2)cc1]

was synthesized by the following procedure.

Triethylamine (0.447 mL, 3.20 mmol) was added dropwise to a solution of 4-methoxyphenylhydrazine hydrochloride (280 mg, 1.60 mmol) in ethanol (2.7 mL), and the resulting mixture was stirred at room temperature for 30 minutes. To the reaction solution, a solution of 3-(8-(benzyloxymethyl)-1,4-dioxaspiro[4.5]decan-8-yl)-1-(p-tolyl)propyn-1-one (Intermediate 49) (540 mg, 1.33 mmol) in ethanol (2.7 mL) was added dropwise, and the resulting mixture was stirred at room temperature for 14 hours. Thereafter, the reaction solution was concentrated under reduced pressure. Water was added to the residue, and the resulting solution was extracted with ethyl acetate. The organic layer was washed with 1 M hydrochloric acid, distilled water and brine, and then dried over anhydrous magnesium sulfate, and concentrated under reduced pressure. The residue was purified by flash chromatography (silica gel, n-hexane/ethyl acetate) to obtain Intermediate 50 (458 mg, 0.872 mmol, 65%) as a white amorphous product.

¹H-NMR (400 MHz, CDCl₃) δ: 1.64-1.72 (2H, m), 1.76-1.85 (2H, m), 1.89-1.98 (2H, m), 2.27-2.35 (5H, m), 3.50 (2H, s), 3.80 (3H, s), 3.90-3.99 (4H, m), 4.49 (2H, s), 6.38 (1H, s), 6.80-6.85 (2H, m), 7.06-7.31 (11H, m).

ESI-MS: m/z=525 (M+H)⁺

(Intermediate 51)

As Intermediate 51, 4-(benzyloxymethyl)-4-(1-(4-methoxyphenyl)-5-(p-tolyl)-1H-pyrazol-3-yl)cyclohexan-1-one:

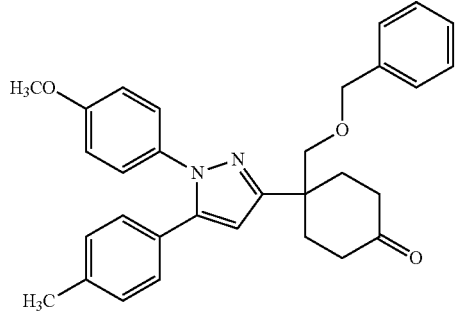 [SMILES: COc1ccc(-n2nc(C3(COCc4ccccc4)CCC(=O)CC3)cc2-c2ccc(C)cc2)cc1]

was synthesized by the following procedure.

To a solution of 3-(8-(benzyloxymethyl)-1,4-dioxaspiro[4.5]decan-8-yl)-1-(4-methoxyphenyl)-5-(p-tolyl)-1H-pyrazole (Intermediate 50) (458 mg, 0.872 mmol) in tetrahydrofuran (2.2 mL), 6 M hydrochloric acid (4.4 mL) was added, and the resulting mixture was stirred at room temperature for 15 hours. The reaction solution was cooled in ice, and a 50% aqueous sodium hydroxide solution was added dropwise thereto at 0° C. until it became basic, followed by extraction of the resulting solution with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 51 (387 mg, 0.804 mmol, 92%) as a white amorphous product.

$^1$H-NMR (400 MHz, CDCl$_3$) δ: 2.11-2.21 (2H, m), 2.31-2.39 (5H, m), 2.52-2.68 (4H, m), 3.57 (2H, s), 3.81 (3H, s), 4.51 (2H, s), 6.44 (1H, s), 6.83-6.88 (2H, m), 7.08-7.34 (11H, m).

ESI-MS: m/z=481 (M+H)$^+$ (Intermediate 52)

As Intermediate 52, 8-(4,5-bis(4-methoxyphenyl)oxazol-2-yl)-1,4-dioxaspiro[4.5]decan-8-ol:

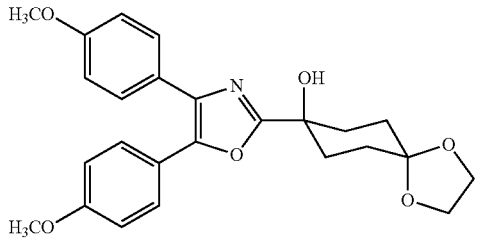 [SMILES: COc1ccc(-c2nc(C3(O)CCC4(CC3)OCCO4)oc2-c2ccc(OC)cc2)cc1]

was synthesized by the following procedure.

To a solution of 2-chloro-1,4-bis(4-methoxyphenyl)oxazole (1.01 g, 3.20 mmol) in tetrahydrofuran (32 mL), which had been synthesized by the known production method (WO 07/111,323), 1.09 M borane-tetrahydrofuran complex (4.0 mL, 4.36 mmol) was added at 0° C., and the resulting mixture was stirred at the same temperature for 1 hour. To the reaction solution, 2.66 M n-butyllithium (1.47 mL, mmol) was added at −78° C., and the resulting mixture was stirred at the same temperature for 1 hour. To the reaction solution, 1,4-cyclohexanedione monoethylene ketal (524 mg, 3.36 mmol) was added, and the obtained solution was allowed to warm gradually to room temperature with stifling. To the reaction solution, 1M hydrochloric acid was added to acidify it, and the resulting solution was extracted with ethyl acetate. The organic layer was dried over anhydrous magnesium sulfate, and concentrated under reduced pressure. The residue was purified by flash chromatography (silica gel, n-hexane/ethyl acetate) to obtain Intermediate 52 (844 mg, 1.92 mmol, 60%) as a pale yellow amorphous product.

$^1$H-NMR (400 MHz, CDCl$_3$) δ: 1.71-1.80 (2H, m), 2.01-2.11 (4H, m), 2.30-2.41 (2H, m), 2.76 (1H, s), 3.83 (3H, s), 3.84 (3H, s), 3.99 (4H, dd, J=Hz), 6.89 (2H, d, J=8.8 Hz), 6.90 (2H, d, J=8.8 Hz), 7.50 (2H, d, J=8.8 Hz), 7.56 (2H, d, J=8.8 Hz).

(Intermediate 53)

As Intermediate 53, 1,4-dioxaspiro[4.5]decan-8-carboxyamide:

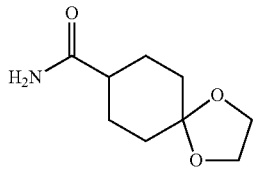 [SMILES: NC(=O)C1CCC2(CC1)OCCO2]

was synthesized by the following procedure.

Triethylamine (5.87 mL, 42.1 mmol) and n-propyl chloroformate were added at 0° C. to a solution of 1,4-dioxaspiro[4.5]decan-8-carboxylic acid (823 mg, 4.42 mmol) in tetrahydrofuran (22 mL), and the resulting mixture was stirred at the same temperature for 1 hour. After adding dropwise, the resulting mixture was stirred at room temperature for 30 minutes. To the reaction solution, 28% aqueous ammonia (1.5 mL) was added, and the resulting mixture was stirred at room temperature for 1 hour. The organic layer was separated from the reaction solution, dried over sodium sulfate and concentrated under reduced pressure. The residue was purified by flash chromatography (silica gel, n-hexane/ethyl acetate) to obtain Intermediate 53 (694 mg, 3.75 mmol, 85%) as a colorless amorphous product.

$^1$H-NMR (400 MHz, CDCl$_3$) δ: 1.53-1.61 (2H, m), 1.72-1.86 (4H, m), 1.91-1.98 (2H, m), 2.17-2.25 (1H, m), 3.95 (4H, s), 5.29 (1H, brs), 5.46 (1H, brs).

ESI-MS: m/z=186 (M+H)$^+$ (Intermediate 54)

As Intermediate 54, 1,4-dioxaspiro[4.5]decan-8-carbothioamide:

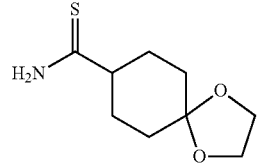 [SMILES: NC(=S)C1CCC2(CC1)OCCO2]

was synthesized by the following procedure.

Lawesson's reagent (337 mg, 0.834 mmol) was added to a solution of 1,4-dioxaspiro[4.5]decan-8-carboxyamide (Intermediate 53) (281 mg, 1.52 mmol) in toluene (5 mL), and the resulting mixture was stirred at 100° C. for 1 hour and then allowed to cool to room temperature. Methanol was added to the reaction solution, and the obtained solution was concentrated under reduced pressure. The residue was purified by flash chromatography (silica gel, n-hexane/ethyl acetate) to obtain Intermediate 54 (147 mg, 0.730 mmol, 48%) as a white solid.

$^1$H-NMR (400 MHz, CDCl$_3$) δ: 1.57-1.66 (2H, m), 1.79-1.90 (4H, m), 1.97-2.03 (2H, m), 2.64-2.72 (1H, m), 3.96 (4H, s), 6.89 (1H, brs), 7.46 (1H, brs).

ESI-MS: m/z=202 (M+H)$^+$ (Intermediate 55)

As Intermediate 55, 8-(4-(4-methoxyphenyl)-5-(p-tolyl)thiazol-2-yl)-1,4-dioxaspiro[4.5]decane:

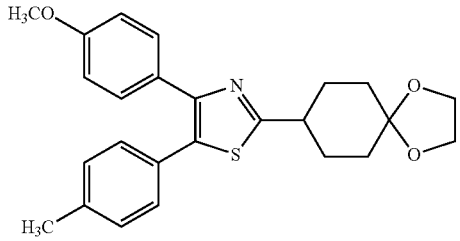 [SMILES: COc1ccc(-c2nc(C3CCC4(CC3)OCCO4)sc2-c2ccc(C)cc2)cc1]

was synthesized by the following procedure.

A solution of 1,4-dioxaspiro[4.5]decan-8-carbothioamide (Intermediate 54) (389 mg, 1.93 mmol) and 2-bromo-1-(4-methoxyphenyl)-2-(p-tolyl)ethanone (588 mg, 1.84 mmol) in acetonitrile (9.2 mL) was stirred at room temperature for 4 hours. A saturated aqueous sodium hydrogen carbonate solution was added to the reaction solution, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 55 (630 mg, 1.49 mmol, 81%) as a colorless amorphous product.

¹H-NMR (400 MHz, CDCl₃) δ: 1.68-1.76 (2H, m), 1.88-1.98 (4H, m), 2.18-2.24 (2H, m), 2.35 (3H, s), 3.05-3.13 (1H, m), 3.80 (3H, s), 3.99 (4H, s), 6.79-6.82 (2H, m), 7.11 (2H, d, J=8.0 Hz), 7.22 (2H, d, J=8.0 Hz), 7.43-7.46 (2H, m).

ESI-MS: m/z=422 (M+H)⁺

(Intermediate 56)

As Intermediate 56, 8-(4-(4-methoxyphenyl)-5-(p-tolyl)thiazol-2-yl)-1,4-dioxaspiro[4.5]decan-8-ol:

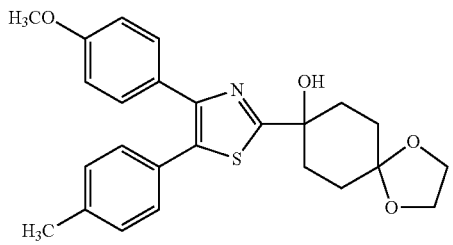 [SMILES: COc1ccc(-c2nc(C3(O)CCC4(CC3)OCCO4)sc2-c2ccc(C)cc2)cc1]

was synthesized by the following procedure.

To a solution of 8-(4-(4-methoxyphenyl)-5-(p-tolyl)thiazol-2-yl)-1,4-dioxaspiro[4.5]decane (Intermediate 55) (734 mg, 1.74 mmol) in tetrahydrofuran (8.7 mL), a 1.63 M n-butyllithium/n-hexane solution (1.17 mL) was added at −78° C., and the resulting mixture was stirred at the same temperature for 1 hour. The reaction solution was added at −78° C. to a solution of 3-phenyl-2-(phenylsulfonyl)-1,2-oxaziridine (546 mg, 2.09 mmol) in tetrahydrofuran (8.7 mL), and the obtained solution was allowed to warm gradually to room temperature with stifling. Distilled water was added to the reaction solution, and the resulting solution was extracted with ethyl acetate. The organic layer was washed with brine, and then dried over sodium sulfate, and concentrated under reduced pressure. The residue was purified by flash chromatography (silica gel, n-hexane/ethyl acetate) to obtain Intermediate 56 (417 mg, 0.954 mmol, 55%) as a colorless amorphous product.

¹H-NMR (400 MHz, CDCl₃) δ: 1.73-1.79 (2H, m), 2.03-2.10 (4H, m), 2.32-2.39 (2H, m), 2.37 (3H, s), 2.78 (1H, s), 3.84 (3H, s), 3.97-4.02 (4H, m), 6.88-6.92 (2H, m), 7.16 (2H, d, J=8.4 Hz), 7.47 (2H, d, J=8.4 Hz), 7.55-7.58 (2H, m).

ESI-MS: m/z=438 (M+H)⁺

(Intermediate 57)

As Intermediate 57, 4-hydroxy-4-(1-(4-methoxyphenyl)-5-(p-tolyl)-1H-pyrazol-3-yl)-cis-cyclohexyl 2-benzyloxycarbonylaminoacetate:

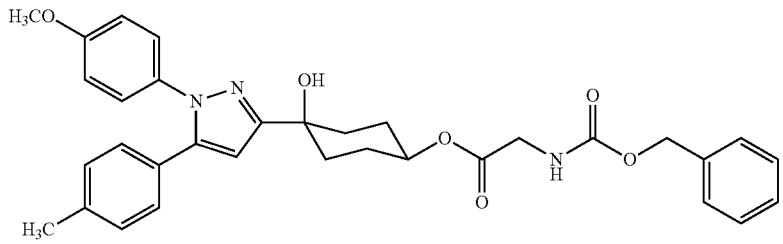 [SMILES: COc1ccc(-n2nc(C3(O)CCC(OC(=O)CNC(=O)OCc4ccccc4)CC3)cc2-c2ccc(C)cc2)cc1]

was synthesized by the following procedure.

Triethylamine (0.084 mL, 0.60 mmol), 2-benzyloxycarbonylamino acetic acid (46.2 mg, 0.241 mmol), 1-ethyl-3-(3-dimethylaminopropyl)carbodiimide hydrochloride (46.2 mg, 0.241 mmol), and 1-hydroxybenzotriazole (15.4 mg, 0.100 mmol) were added at room temperature to a solution of 1-(1-(4-methoxyphenyl)-5-(p-tolyl)-1H-pyrazol-3-yl)-cyclohexan-cis-1,4-diol (Compound 3) (76.0 mg, 0.201 mmol) in dichloromethane (2.00 mL), and the resulting mixture was stirred for 20 hours. Distilled water was added to the reaction solution, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 57 (33.2 mg, 0.058 mmol, 29%) as a colorless amorphous product.

¹H-NMR (400 MHz, CDCl₃) δ: 1.91-2.07 (8H, m), 2.33 (3H, s), 2.75 (1H, s), 3.80 (3H, s), 3.98-3.99 (2H, m), 4.89-4.94 (1H, m), 5.14 (2H, s), 5.33-5.35 (1H, m), 6.36 (1H, s), 6.82-6.86 (2H, m), 7.08-7.10 (4H, m), 7.17-7.21 (2H, m), 7.29-7.38 (5H, m).

ESI-MS: m/z=552 (M−OH)⁺

(Intermediate 58)

As Intermediate 58, (S)-4-hydroxy-4-(1-(4-methoxyphenyl)-5-(p-tolyl)-1H-pyrazol-3-yl)-cis-cyclohexyl 2-(benzyloxycarbonylamino)-3-methylbutanoate was synthesized in the same manner as Intermediate 57.

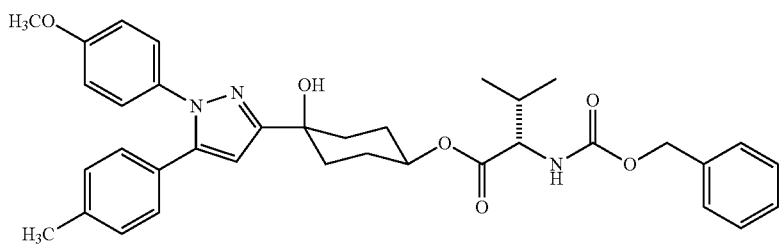 [SMILES: COc1ccc(-n2nc(C3(O)CCC(OC(=O)[C@@H](NC(=O)OCc4ccccc4)C(C)C)CC3)cc2-c2ccc(C)cc2)cc1]

¹H-NMR (400 MHz, CDCl₃) δ: 0.92 (3H, d, J=6.4 Hz), 0.99 (3H, d, J=6.4 Hz), 1.89-2.10 (8H, m), 2.16-2.24 (1H, m), 2.34 (3H, s), 2.63 (1H, s), 3.81 (3H, s), 4.30-4.33 (1H, m), 4.88-4.95 (1H, m), 5.12 (2H, s), 5.28-5.30 (1H, m), 6.36 (1H, s), 6.78-6.82 (2H, m), 7.09-7.10 (4H, m), 7.18-7.24 (2H, m), 7.29-7.38 (5H, m).

ESI-MS: m/z=594 (M−OH)⁺

(Intermediate 59)

As Intermediate 59, (S)-4-hydroxy-4-(1-(4-methoxyphenyl)-5-(p-tolyl)-1H-pyrazol-3-yl)cyclohexyloxy)methyl 2-(benzyloxycarbonylamino)-3-methylbutanoate:

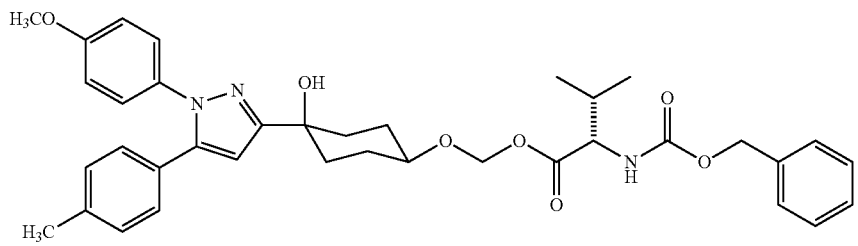 [SMILES: COc1ccc(-n2nc(C3(O)CCC(OCOC(=O)[C@@H](NC(=O)OCc4ccccc4)C(C)C)CC3)cc2-c2ccc(C)cc2)cc1]

was synthesized by the following procedure.

Molecular sieves 4A (300 mg) and diisopropylethylamine (0.210 mL, 1.21 mmol) were added at room temperature to a solution of 1-(1-(4-methoxyphenyl)-5-(p-tolyl)-1H-pyrazol-3-yl)-cyclohexan-cis-1,4-diol (Compound 3) (199 mg, 0.506 mmol) in dichloromethane (3.00 mL), and the obtained mixture was cooled to −50° C. Then, (S)-iodomethyl 2-benzyloxycarbonylamino-3-methylbutanoate (0.187 mL, 1.26 mmol) and silver trifluoromethanesulfonate (232 mg, 0.904 mmol) were added thereto at the same temperature, and the resulting mixture was stirred for 2 hours, followed by stifling the mixture at −30° C. for 14 hours. A saturated sodium bicarbonate solution was added to the reaction solution, and the resulting solution was filtered through Celite. The filtrate was washed with brine, and the organic layer was dried over anhydrous sodium sulfate and concentrated under reduced pressure. The residue was purified by flash chromatography (silica gel, n-hexane/ethyl acetate) to obtain Intermediate 59 (123 mg, 0.192 mmol, 64%) as a colorless amorphous product.

$^1$H-NMR (400 MHz, CDCl$_3$) δ: 0.92 (3H, d, J=6.4 Hz), 1.01 (3H, d, J=6.4 Hz), 1.88-1.99 (6H, m), 2.02-2.09 (2H, m), 2.20-2.26 (1H, m), 2.34 (3H, s), 2.50 (1H, s), 3.66-3.72 (1H, m), 3.81 (3H, s), 4.32-4.36 (1H, m), 5.12 (2H, s), 5.38 (1H, d, J=6.4 Hz), 5.50 (1H, d, J=6.4 Hz), 6.37 (1H, s), 6.83-6.87 (2H, m), 7.08-7.11 (4H, m), 7.18-7.24 (2H, m), 7.29-7.38 (5H, m).

ESI-MS: m/z=624 (M−OH)$^+$ (Intermediate 60)

As Intermediate 60, dibenzyl 4-hydroxy-4-(1-(4-methoxyphenyl)-5-(p-tolyl)-1H-pyrazol-3-yl)-cis-cyclohexyl phosphate:

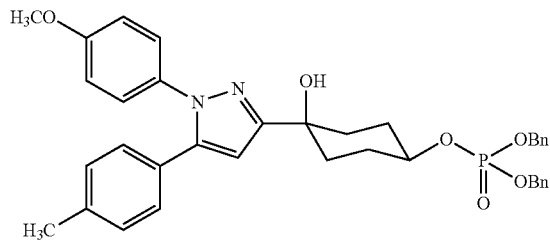 [SMILES: COc1ccc(-n2nc(C3(O)CCC(OP(=O)(OCc4ccccc4)OCc4ccccc4)CC3)cc2-c2ccc(C)cc2)cc1]

was synthesized by the following procedure.

To a solution of 1-(1-(4-methoxyphenyl)-5-(p-tolyl)-1H-pyrazol-3-yl)cyclohexan-cis-1,4-diol (Compound 3) (200 mg, 0.528 mmol) in tetrahydrofuran (2.6 mL), 55% sodium hydride (55.3 mg, 1.27 mmol) and tetrabenzylpyrophosphonate (370 mg, 0.687 mmol) were sequentially added with stirring under ice-cooling, and the resulting mixture was stirred at room temperature for 15 hours. The reaction solution was cooled in ice, and water was added thereto. The resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 60 (251 mg, 0.393 mmol, 74%) as a colorless transparent oily compound.

$^1$H-NMR (400 MHz, CDCl$_3$) δ: 1.87-2.11 (8H, m), 2.33 (3H, s), 3.79 (3H, s), 4.42-4.51 (1H, m), 5.00-5.12 (4H, m), 6.34 (1H, s), 6.81-6.87 (2H, m), 7.09 (4H, s), 7.16-7.23 (2H, m), 7.29-7.37 (10H, m).

ESI-MS: m/z=639 (M+H)$^+$ (Compound 4)

As Compound 4, 4-hydroxy-4-(1-(4-methoxyphenyl)-5-(p-tolyl)-1H-pyrazol-3-yl)cyclohexan-1-one:

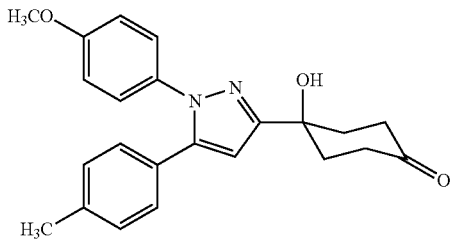 [SMILES: COc1ccc(-n2nc(C3(O)CCC(=O)CC3)cc2-c2ccc(C)cc2)cc1]

was synthesized by the following procedure.

To a solution of 8-(1-(4-methoxyphenyl)-5-(p-tolyl)-1H-pyrazol-3-yl)-1,4-dioxaspiro[4.5]decan-8-ol (Intermediate 18) (14.6 g, 34.7 mmol) in tetrahydrofuran (69.4 mL), 6 M hydrochloric acid (138.9 mL) was added, and the resulting mixture was stirred at room temperature for 15 hours. The reaction solution was cooled in ice, and a 50% aqueous sodium hydroxide solution was added dropwise thereto at 0° C. until it became basic, followed by extraction of the resulting solution with ethyl acetate. The organic layer was washed with brine, dried over anhydrous sodium sulfate, and concentrated under reduced pressure. The residue was purified by recrystallization (n-hexane/ethyl acetate, 70° C.) to obtain Compound 4 (10.5 g, 27.9 mmol, 80%) as a white solid.

$^1$H-NMR (400 MHz, CDCl$_3$) δ: 2.33-2.43 (9H, m), 2.87-2.95 (3H, m), 3.82 (3H, s), 6.39 (1H, s), 6.86 (2H, d, J=8.8 Hz), 7.10 (4H, s), 7.22 (2H, d, J=8.8 Hz).

IR (KBr, cm$^{-1}$): 3321, 2929, 1712, 1518, 1463, 1299, 1249, 1179, 1114, 1027, 961, 821.

ESI-MS: m/z=377 (M+H)$^+$ (Intermediate 62)

As Compound 62, 4-hydroxy-4-(1-(4-methoxyphenyl)-5-(6-methylpyridin-3-yl)-1H-pyrazol-3-yl)-cyclohexan-1-one:

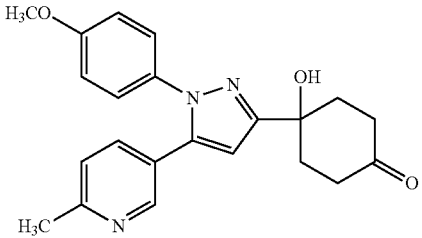 [SMILES: COc1ccc(-n2nc(C3(O)CCC(=O)CC3)cc2-c2ccc(C(F)(F)F)cc2)cc1]

was synthesized by the following procedure.

To a solution of 8-(1-(4-methoxyphenyl)-5-(6-methylpyridin-3-yl)-1H-pyrazol-3-yl)-1,4-dioxaspiro[4.5]decan-8-ol (Intermediate 19) (128.8 mg, 0.30 mmol) in tetrahydrofuran (0.6 mL), 6 M hydrochloric acid (1.2 mL) was added, and the resulting mixture was stirred at room temperature for 3 hours. The reaction solution was cooled in ice, and a 50% aqueous sodium hydroxide solution was added dropwise thereto at 0° C. until it became basic, followed by extraction of the resulting solution with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 62 (109.5 mg, 0.29 mmol, 96%) as an amorphous product.

$^1$H-NMR (400 MHz, CDCl$_3$) δ: 2.34-2.44 (6H, m), 2.55 (3H, s), 2.87-2.95 (2H, m), 3.18 (1H, s), 3.82 (3H, s), 6.49 (1H, s), 6.87 (2H, d, J=8.8 Hz), 7.08 (1H, d, J=8.1 Hz), 7.19 (2H, d, J=8.8 Hz), 7.35 (1H, dd, J=2.2, 8.1 Hz), 8.40 (1H, d, J=2.2 Hz).

ESI-MS: m/z=378 (M+H)$^+$ (Intermediate 63)

As Compound 63, 4-(1,5-bis(4-methoxyphenyl)-1H-pyrazol-3-yl)-4-hydroxy-cyclohexan-1-one:

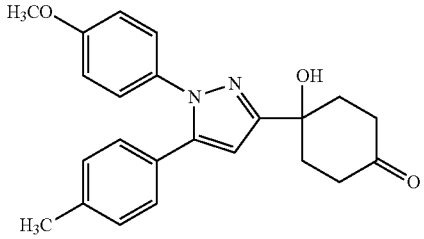

was synthesized by the following procedure.

To a solution of 8-(1,5-bis(4-methoxyphenyl)-1H-pyrazol-3-yl)-1,4-dioxaspiro[4.5]decan-8-ol (Intermediate 20) (658 mg, 1.50 mmol) in tetrahydrofuran (3.75 mL), 6 M hydrochloric acid (7.5 mL) was added at 0° C., and the resulting mixture was stirred at room temperature for 5 hours. The reaction solution was neutralized by pouring it into an ice-cooled 10% aqueous sodium hydroxide solution. The resulting solution was then basified by adding thereto a saturated sodium bicarbonate solution, and extracted with ethyl acetate. The organic layer was dried over anhydrous magnesium sulfate, and concentrated under reduced pressure. The residue was purified by flash chromatography (silica gel, n-hexane/ethyl acetate) to obtain Intermediate 63 (523 mg, 1.33 mmol, 89%) as an amorphous product.

$^1$H-NMR (400 MHz, CDCl$_3$) δ: 2.30-2.45 (6H, m), 2.86-2.96 (2H, m), 2.99 (1H, s), 3.80 (3H, s), 3.82 (3H, s), 6.36 (1H, s), 6.82 (2H, d, J=8.8 Hz), 6.87 (2H, d, J=8.8 Hz), 7.13 (2H, d, J=8.8 Hz), 7.21 (2H, d, J=8.8 Hz).

ESI-MS: m/z=393 (M+H)$^+$ (Intermediate 64)

As Compound 64, 4-(5-(4-chlorophenyl)-1-(4-methoxyphenyl)-1H-pyrazol-3-yl)-4-hydroxy-cyclohexan-1-one:

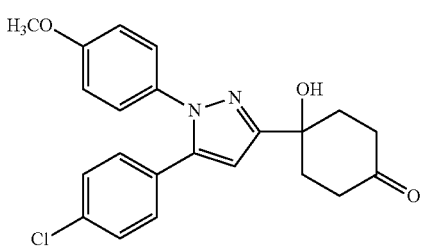 [SMILES: COc1ccc(-n2nc(C3(O)CCC(=O)CC3)cc2-c2ccc(C#N)cc2)cc1]

was synthesized by the following procedure.

To a solution of 8-(5-(4-chlorophenyl)-1-(4-methoxyphenyl)-1H-pyrazol-3-yl)-1,4-dioxaspiro[4.5]decan-8-ol (Intermediate 21) (756 mg, 1.71 mmol) in tetrahydrofuran (4.3 mL), 6 M hydrochloric acid (8.6 mL) was added, and the resulting mixture was stirred at room temperature for 15 hours. The reaction solution was cooled in ice, and a 50% aqueous sodium hydroxide solution was added dropwise thereto at 0° C. until it became basic, followed by extraction of the resulting solution with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 64 (619 mg, 1.56 mmol, 91%) as an amorphous product.

$^1$H-NMR (400 MHz, CDCl$_3$) δ: 2.31-2.45 (6H, m), 2.85-2.98 (3H, m), 3.82 (3H, s), 6.43 (1H, s), 6.86-6.90 (2H, m), 7.14 (2H, d, J=8.8 Hz), 7.19 (2H, d, J=8.8 Hz), 7.26-7.29 (2H, m).

ESI-MS: m/z=397 (M+H)$^+$ (Intermediate 65)

As Compound 65, 4-hydroxy-4-(1-(4-chlorophenyl)-5-(p-tolyl)-1H-pyrazol-3-yl)-cyclohexan-1-one:

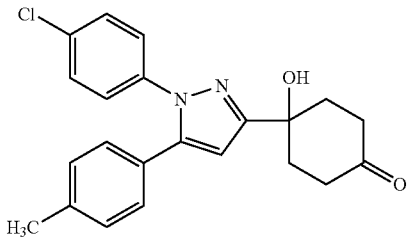

was synthesized by the following procedure.

To a solution of 8-(1-(4-chlorophenyl)-5-(p-tolyl)-1H-pyrazol-3-yl)-1,4-dioxaspiro[4.5]decan-8-ol (Intermediate 22) (931 mg, 2.19 mmol) in tetrahydrofuran (5.5 mL), 6 M hydrochloric acid (11 mL) was added, and the resulting mixture was stirred at room temperature for 15 hours. The reaction solution was basified by pouring it into a saturated aqueous sodium hydrogen carbonate solution, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 65 (513 mg, 1.35 mmol, 61%) as a white solid.

$^1$H-NMR (400 MHz, CDCl$_3$) δ: 2.32-2.36 (4H, m), 2.36 (3H, s), 2.38-2.44 (2H, m), 2.87-2.95 (2H, m), 2.90 (1H, s), 6.41 (1H, s), 7.10 (2H, d, J=8.0 Hz), 7.14 (2H, d, J=8.0 Hz), 7.23 (2H, d, J=8.8 Hz), 7.31 (2H, d, J=8.8 Hz).

ESI-MS: m/z=381 (M+H)$^+$

The following compounds were synthesized in the same manner as in the synthesis of the above-described Intermediates.

TABLE 13

| Intermediate | Structural Formula | Compound Data |
| --- | --- | --- |
| 66 | (4-chlorophenyl, 4-chlorophenyl pyrazole with 4-hydroxy-cyclohexanone) | $^1$H-NMR (400 MHz, CDCl$_3$) δ: 2.31-2.45 (6H, m), 2.86-2.96 (3H, m), 6.45 (1H, s), 7.15 (2H, d, J = 8.8 Hz), 7.22 (2H, d, J = 8.8 Hz), 7.31-7.35 (4H, m).<br>ESI-MS: m/z = 401 (M + H)$^+$ |
| 67 | (phenyl, 4-chlorophenyl pyrazole with 4-hydroxy-cyclohexanone) | $^1$H-NMR (400 MHz, CDCl$_3$) δ: 2.32-2.44 (6H, m), 2.85-2.95 (2H, m), 3.10 (1H, brs), 6.45 (1H, s), 7.13-7.16 (2H, m), 7.26-7.39 (7H, m).<br>ESI-MS: m/z = 367 (M + H)$^+$ |
| 68 | (4-methylphenyl, 4-methylphenyl pyrazole with 4-hydroxy-cyclohexanone) | $^1$H-NMR (400 MHz, CDCl$_3$) δ: 2.32-2.45 (6H, m), 2.34 (3H, s), 2.36 (3H, s), 2.87-2.95 (2H, m), 2.98 (1H, s), 6.37 (1H, s), 7.10-7.19 (8H, m).<br>ESI-MS: m/z = 361 (M + H)$^+$ |
| 69 | (phenyl, 4-methylphenyl pyrazole with 4-hydroxy-cyclohexanone) | $^1$H-NMR (400 MHz, CDCl$_3$) δ: 2.32-2.45 (6H, m), 2.35 (3H, s), 2.87-2.96 (2H, m), 2.97 (1H, s), 6.41 (1H, s), 7.09-7.13 (4H, m), 7.27-7.37 (5H, m).<br>ESI-MS: m/z = 347 (M + H)$^+$ |
| 70 | (4-methoxyphenyl, phenyl pyrazole with 4-hydroxy-cyclohexanone) | $^1$H-NMR (400 MHz, CD$_3$OD) δ: 2.44-2.38 (6H, m), 2.87-2.96 (3H, m), 3.82 (3H, s), 6.43 (1H, s), 6.86 (2H, d, J = 9.0 Hz), 7.19-7.24 (4H, m), 7.29-7.32 (3H, m).<br>ESI-MS: m/z = 363 (M + H)$^+$ |
| 71 | (4-methylphenyl, phenyl pyrazole with 4-hydroxy-cyclohexanone) | $^1$H-NMR (400 MHz, CDCl$_3$) δ: 2.32-2.44 (2H, m), 2.35-2.39 (5H, m), 2.43-2.50 (2H, m), 2.89-2.96 (2H, m), 6.43 (1H, s), 7.13 (2H, d, J = 8.8 Hz), 7.17 (2H, d, J = 8.8 Hz), 7.20-7.24 (2H, m), 7.29-7.32 (3H, m).<br>ESI-MS: m/z = 347 (M + H)$^+$ |

TABLE 13-continued

| Intermediate | Structural Formula | Compound Data |
|---|---|---|
| 72 | | $^1$H-NMR (400 MHz, CDCl3) δ: 2.31-2.34 (2H, m), 2.36 (3H, s), 2.37-2.39 (2H, m), 2.41-2.43 (2H, m), 2.86-2.96 (2H, m), 2.99 (1H, s), 3.80 (3H, s), 6.36 (1H, s), 6.83 (2H, d, J = 8.8 Hz), 7.13-7.19 (6H, m).<br>ESI-MS: m/z = 377 (M + H)$^+$ |
| 73 | | $^1$H-NMR (400 MHz, CDCl3) δ: 2.31-2.35 (4H, m), 2.38-2.43 (2H, m), 2.86-2.96 (3H, m), 3.82 (3H, s), 6.38 (1H, s), 6.84 (2H, d, J = 9.0 Hz), 7.13 (2H, d, J = 11.7 Hz), 7.23 (2H, t, J = 8.9 Hz), 7.31 (2H, d, J = 11.5 Hz).<br>ESI-MS: m/z = 397 (M + H)$^+$ |
| 74 | | $^1$H-NMR (400 MHz, CDCl3) δ: 2.31-2.45 (6H, m), 2.86-2.96 (2H, m), 3.02 (1H, s), 3.80 (3H, s), 6.37 (1H, s), 6.83 (2H, d, J = 8.8 Hz), 7.14 (2H, d, J = 8.8 Hz), 7.28-7.37 (5H, m). |
| 75 | | $^1$H-NMR (400 MHz, CDCl3) δ: 2.33-2.37 (4H, m), 2.39-2.43 (2H, m), 2.87-2.95 (3H, m), 3.83 (3H, s), 6.50 (1H, s), 6.89 (2H, d, J = 8.0 Hz), 7.20 (2H, d, J = 8.0 Hz), 7.33 (2H, d, J = 8.0 Hz), 7.56 (2H, d, J = 8.0 Hz).<br>ESI-MS: m/z = 431 (M + H)$^+$ |
| 76 | | $^1$H-NMR (400 MHz, CDCl3) δ: 1.23 (3H, t, J = 7.6 Hz), 2.31-2.45 (6H, m), 2.64 (2H, q, J = 7.6 Hz), 2.86-2.96 (3H, m), 3.82 (3H, s), 6.39 (1H, s), 6.83-6.89 (2H, m), 7.13 (4H, s), 7.20-7.25 (2H, m).<br>ESI-MS: m/z = 391 (M + H)$^+$ |
| 77 | | $^1$H-NMR (400 MHz, CDCl$_3$) δ: 2.31-2.45 (9H, m), 2.86-2.97 (3H, m), 3.90 (3H, s), 6.39 (1H, s), 6.89 (1H, t, J = 8.8 Hz), 6.98-7.01 (1H, m), 7.08-7.15 (5H, m).<br>ESI-MS: m/z = 395 (M + H)$^+$ |

TABLE 13-continued

| Intermediate | Structural Formula | Compound Data |
| --- | --- | --- |
| 78 | | $^1$H-NMR (400 MHz, CDCl$_3$) δ: 2.26 (3H, d, J = 1.6 Hz), 2.31-2.45 (6H, m), 2.85-2.96 (3H, m), 3.82 (3H, s), 6.41 (1H, s), 6.84-6.90 (4H, m), 7.10 (1H, t, J = 8.0 Hz), 7.18-7.23 (2H, m).<br>ESI-MS: m/z = 395 (M + H)$^+$ |
| 79 | | $^1$H-NMR (400 MHz, CDCl$_3$) δ: 2.30-2.45 (9H, m), 2.83 (1H, s), 2.86-2.97 (2H, m), 6.45 (1H, s), 7.10-7.20 (4H, m), 7.40-7.45 (2H, m), 7.59-7.64 (2H, m).<br>ESI-MS: m/z = 372 (M + H)$^+$ |
| 80 | | $^1$H-NMR (400 MHz, CDCl$_3$) δ: 2.31-2.46 (6H, m), 2.84-2.96 (3H, m), 3.83 (3H, s), 6.53 (1H, s), 6.87-6.92 (2H, m), 7.15-7.21 (2H, m), 7.30-7.34 (2H, m), 7.57-7.61 (2H, m).<br>ESI-MS: m/z = 425 (M + H)$^+$ |

(Intermediate 81)

As Compound 81, 4-(4-chloro-1-(4-methoxyphenyl)-5-(p-tolyl)-1H-pyrazol-3-yl)-c-4-hydroxy-cyclohexan-r-1-yl acetate:

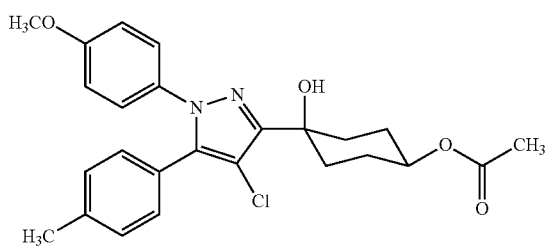 [SMILES: COc1ccc(-n2nc(C3(O)CCC(OC(C)=O)CC3)c(Cl)c2-c2ccc(C)cc2)cc1]

was synthesized by the following procedure.

To a solution of c-4-hydroxy-4-(1-(4-methoxyphenyl)-5-(p-tolyl)-1H-pyrazol-3-yl)-cyclohexan-r-1-yl acetate (Compound 12) (140 mg, 0.333 mmol) in acetonitrile (1.66 mL), N-chlorosuccinimide (49 mg, 0.366 mmol) was added. The resulting mixture was stirred at 80° C. for 15 hours, and allowed to cool to room temperature. Brine was added to the reaction solution, and the resulting solution was extracted with ethyl acetate. The organic layer was dried over anhydrous magnesium sulfate, and concentrated under reduced pressure. The residue was purified by flash chromatography (silica gel, n-hexane/ethyl acetate) to obtain Intermediate 81 (67 mg, 0.147 mmol, 44%) as a white solid.

$^1$H-NMR (400 MHz, CDCl$_3$) δ: 1.92-2.04 (6H, m), 2.28-2.36 (8H, m), 3.10 (1H, s), 3.79 (3H, s), 4.85-4.88 (1H, m), 6.80-6.82 (2H, m), 7.11-7.16 (6H, m).

(Intermediate 82)

As Compound 82, 4-(4,5-bis(4-methoxyphenyl)oxazol-2-yl)-4-hydroxycyclohexan-1-one:

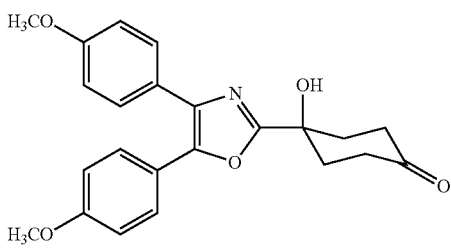 [SMILES: COc1ccc(-c2nc(C3(O)CCC(=O)CC3)oc2-c2ccc(OC)cc2)cc1]

was synthesized by the following procedure.

To a solution of 8-(4,5-bis(4-methoxyphenyl)oxazol-2-yl)-1,4-dioxaspiro[4.5]decan-8-ol (Intermediate 52) (781 mg, 1.78 mmol) in tetrahydrofuran (4.5 mL), 6 M hydrochloric acid (9.0 mL) was added at 0° C., and the resulting mixture was stirred at room temperature for 2 hours. The reaction solution was cooled to 0° C., and alkalified by addition of a 10% aqueous sodium hydroxide solution and a saturated sodium bicarbonate solution. The resulting solution was extracted with ethyl acetate. The organic layer was dried over anhydrous magnesium sulfate, and concentrated under reduced pressure. The residue was purified by recrystallization (ethyl acetate/n-hexane) to obtain Intermediate 82 (445 mg, 1.13 mmol, 63%) as a pale yellow solid.

$^1$H-NMR (400 MHz, CDCl$_3$) δ: 2.32-2.54 (6H, m), 2.81-2.92 (2H, m), 3.17 (1H, m), 3.84 (6H, s), 6.90 (2H, d, J=8.8 Hz), 6.91 (2H, d, J=8.8 Hz), 7.49 (2H, d, J=8.8 Hz), 7.56 (2H, d, J=8.8 Hz).

ESI-MS: m/z=394 (M+H)$^+$ (Intermediate 83)

As Compound 83, 4-hydroxy-4-(4-(4-methoxyphenyl)-5-(p-tolyl)thiazol-2-yl)cyclohexan-1-one:

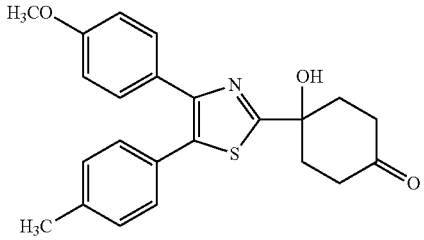

was synthesized by the following procedure.

To a solution of 8-(4-(4-methoxyphenyl)-5-(p-tolyl)thiazol-2-yl)-1,4-dioxaspiro[4.5]decan-8-ol (Intermediate 56) (469 mg, 1.07 mmol) in tetrahydrofuran (5.4 mL), 6 M hydrochloric acid (5.4 mL) was added at 0° C., and the resulting mixture was stirred at room temperature for 14 hours. The reaction solution was basified by pouring it into a saturated aqueous sodium hydrogen carbonate solution, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 83 (352 mg, 0.895 mmol, 83%) as a white solid.

$^1$H-NMR (400 MHz, CDCl$_3$) δ: 2.33-2.51 (6H, m), 2.37 (3H, s), 2.86-2.95 (2H, m), 3.50 (1H, s), 3.81 (3H, s), 6.81-6.84 (2H, m), 7.14 (2H, d, J=8.0 Hz), 7.24 (2H, d, J=8.0 Hz), 7.44-7.48 (2H, m).

ESI-MS: m/z=394 (M+H)$^+$ (Intermediate 84)

As Compound 84, c-4-hydroxy-1-(1-(4-methoxyphenyl)-5-(p-tolyl)-1H-pyrazol-3-yl)-cyclohexan-r-1-yl acetate:

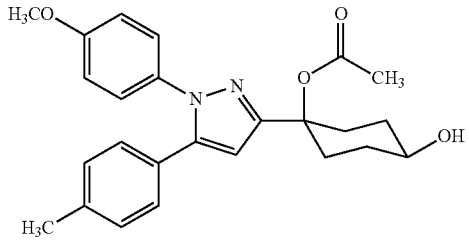 [SMILES: COc1ccc(-n2nc(C3(OC(C)=O)CCC(O)CC3)cc2-c2ccc(C)cc2)cc1]

was synthesized by the following procedure.

Potassium carbonate (89.0 mg, 0.642 mmol) was added to a solution of 1-(1-(4-methoxyphenyl)-5-(p-tolyl)-1H-pyrazol-3-yl)-cyclohexan-cis-1,4-diyl diacetate (Intermediate 38) (297 mg, 0.642 mmol) in methanol (4.3 mL), and the resulting mixture was stirred at room temperature for 4 hours. Water was added to the reaction solution to stop the reaction, and the resulting solution was extracted with ethyl acetate. The organic layer was washed with brine, dried over anhydrous sodium sulfate, and concentrated under reduced pressure. The residue was purified by flash chromatography (silica gel, n-hexane/ethyl acetate) to obtain Intermediate 84 (213 mg, 0.507 mmol, 79%) as a white solid.

$^1$H-NMR (400 MHz, CDCl$_3$) δ: 1.49 (1H, d, J=4.4 Hz), 1.65-1.74 (2H, m), 1.90-1.98 (4H, m), 2.10 (3H, s), 2.32 (3H, s), 2.71-2.78 (2H, m), 3.74-3.81 (4H, m), 6.37 (1H, s), 6.83 (2H, d, J=9.2 Hz), 7.08 (4H, s), 7.20 (2H, d, J=9.2 Hz).

ESI-MS: m/z=421 (M+H)$^+$

Industrial Applicability

Our cyclohexane derivatives or pharmaceutically acceptable salts thereof can be utilized as a pharmaceutical, especially a therapeutic agent or prophylactic agent for a urine storage disorder(s), comprising them as an effective ingredient.

The invention claimed is:

1. A method of treating a urine storage disorder(s) comprising administering a therapeutically effective amount of a cyclohexane derivative represented by Formula (I):

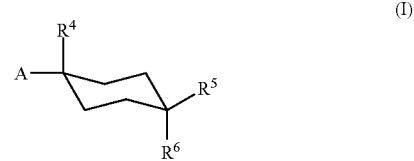

wherein

A is a substituent represented by the Formula (IIa) or (IIb):

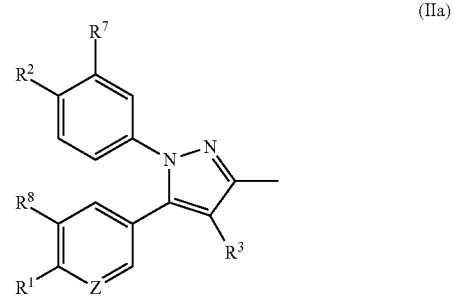

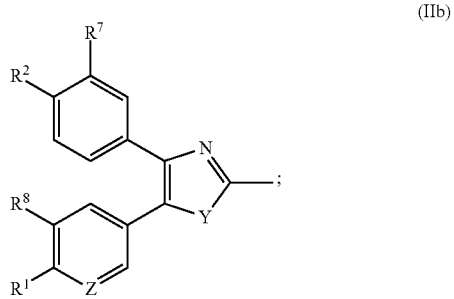

$R^1$ and $R^2$ are each independently a hydrogen atom, chlorine atom, $C_1$-$C_3$ haloalkyl group, $C_1$-$C_4$ alkyl group or a $C_1$-$C_4$ alkoxy group;

$R^3$ is a hydrogen atom or a chlorine atom; $R^4$ is a fluorine atom, hydroxymethyl group or a hydroxyl group;

$R^5$ and $R^6$ are each independently a hydrogen atom, fluorine atom, $C_1$-$C_3$ haloalkyl group, carboxyl group, methoxycarbonyl group, ethoxycarbonyl group, $C_1$-$C_4$ alkoxy group, hydroxyl group or a $C_2$-$C_5$ alkylcarbonyloxy group, or optionally together form an oxo group;

$R^7$ and $R^8$ are each independently a hydrogen atom or a fluorine atom;

Y is an oxygen atom or a sulfur atom;

Z is a nitrogen atom or a methine group, a pharmaceutically acceptable salt thereof, or a prodrug thereof.

2. The method according to claim 1, wherein $R^1$ and $R^2$ are each independently a trifluoromethyl group, methyl group or a methoxy group.

3. The method according to claim 1, wherein $R^3$ is a hydrogen atom.

4. The method according to claim 1, wherein $R^4$ is a hydroxymethyl group or a hydroxyl group.

5. The method according to claim 1, wherein $R^5$ and $R^6$ are each independently a hydrogen atom, fluorine atom, trifluoromethyl group, carboxyl group, methoxy group, hydroxyl group or an acetyloxy group, or optionally together form an oxo group.

6. The method according to claim 1, wherein said urine storage disorder(s) is(are) pollakiuria, urinary incontinence and/or urinary urgency.

7. The method according to claim 2, wherein $R^3$ is a hydrogen atom.

8. The method according to claim 2, wherein $R^4$ is a hydroxymethyl group or a hydroxyl group.

9. The method according to claim 3, wherein $R^4$ is a hydroxymethyl group or a hydroxyl group.

10. The method according to claim 2, wherein $R^5$ and $R^6$ are each independently a hydrogen atom, fluorine atom, trifluoromethyl group, carboxyl group, methoxy group, hydroxyl group or an acetyloxy group, or optionally together form an oxo group.

11. The method according to claim 3, wherein $R^5$ and $R^6$ are each independently a hydrogen atom, fluorine atom, trifluoromethyl group, carboxyl group, methoxy group, hydroxyl group or an acetyloxy group, or optionally together form an oxo group.

12. The method according to claim 4, wherein $R^5$ and $R^6$ are each independently a hydrogen atom, fluorine atom, trifluoromethyl group, carboxyl group, methoxy group, hydroxyl group or an acetyloxy group, or optionally together form an oxo group.

13. The method according to claim 2, wherein said urine storage disorder(s) is(are) pollakiuria, urinary incontinence and/or urinary urgency.

14. The method according to claim 3, wherein said urine storage disorder(s) is(are) pollakiuria, urinary incontinence and/or urinary urgency.

15. The method according to claim 4, wherein said urine storage disorder(s) is(are) pollakiuria, urinary incontinence and/or urinary urgency.

16. The method according to claim 5, wherein said urine storage disorder(s) is(are) pollakiuria, urinary incontinence and/or urinary urgency.

* * * * *

UNITED STATES PATENT AND TRADEMARK OFFICE
CERTIFICATE OF CORRECTION

| | |
|---|---|
| PATENT NO. | : 8,642,625 B2 |
| APPLICATION NO. | : 13/637064 |
| DATED | : February 4, 2014 |
| INVENTOR(S) | : Hareyama et al. |

It is certified that error appears in the above-identified patent and that said Letters Patent is hereby corrected as shown below:

In the Specification

In Column 49, at line 31, please change "double0" to --double--.

Signed and Sealed this
Thirtieth Day of September, 2014

Michelle K. Lee
*Deputy Director of the United States Patent and Trademark Office*